(12) United States Patent
Yarravarapu et al.

(10) Patent No.: US 10,793,544 B2
(45) Date of Patent: Oct. 6, 2020

(54) DISUBSTITUTED AND TRISUBSTITUTED 1,2,3-TRIAZOLES AS WNT INHIBITORS

(71) Applicant: The Board of Regents of the University of Texas System, Austin, TX (US)

(72) Inventors: Nageswari Yarravarapu, Dallas, TX (US); Chuo Chen, Dallas, TX (US); Lawrence Lum, Dallas, TX (US); Lin You, Dallas, TX (US); Chengwei Zhang, Dallas, TX (US); Xiaolei Wang, Dallas, TX (US); Lishu Zhang, Dallas, TX (US)

( * ) Notice: Subject to any disclaimer, the term of this patent is extended or adjusted under 35 U.S.C. 154(b) by 0 days.

(21) Appl. No.: 16/330,050

(22) PCT Filed: Aug. 31, 2017

(86) PCT No.: PCT/US2017/049634
§ 371 (c)(1),
(2) Date: Mar. 1, 2019

(87) PCT Pub. No.: WO2018/045182
PCT Pub. Date: Mar. 8, 2018

(65) Prior Publication Data
US 2019/0202804 A1    Jul. 4, 2019

Related U.S. Application Data

(60) Provisional application No. 62/382,485, filed on Sep. 1, 2016.

(51) Int. Cl.
| | |
|---|---|
| *C07D 401/12* | (2006.01) |
| *C07D 401/14* | (2006.01) |
| *C07D 409/14* | (2006.01) |
| *A61K 31/4192* | (2006.01) |
| *C07D 405/14* | (2006.01) |
| *A61K 31/506* | (2006.01) |
| *A61K 31/4439* | (2006.01) |
| *A61K 31/444* | (2006.01) |
| *A61K 45/06* | (2006.01) |
| *C07D 255/02* | (2006.01) |

(52) U.S. Cl.
CPC ........ *C07D 401/12* (2013.01); *A61K 31/4192* (2013.01); *A61K 31/444* (2013.01); *A61K 31/4439* (2013.01); *A61K 31/506* (2013.01); *A61K 45/06* (2013.01); *C07D 255/02* (2013.01); *C07D 401/14* (2013.01); *C07D 405/14* (2013.01); *C07D 409/14* (2013.01)

(58) Field of Classification Search
CPC ............ A61K 31/4192; A61K 31/4439; A61K 31/444; A61K 31/506; A61K 45/06; C07D 255/02; C07D 401/14; C07D 405/14; C07D 409/14
USPC ...................................................... 548/255
See application file for complete search history.

(56) References Cited

U.S. PATENT DOCUMENTS

| | | | |
|---|---|---|---|
| 2010/0207068 A1 | 8/2010 | Schlueter | |
| 2013/0079328 A1* | 3/2013 | Cheng ................ | C07D 213/56 514/210.18 |
| 2015/0038483 A1* | 2/2015 | Yukimasa ............ | C07D 417/04 514/210.18 |
| 2015/0157633 A1* | 6/2015 | Lum ..................... | A61K 45/06 514/255.01 |

FOREIGN PATENT DOCUMENTS

| | | | | |
|---|---|---|---|---|
| CN | 104945339 | | 9/2015 | |
| WO | WO 2016/055786 | | 4/1916 | |
| WO | WO-2009049098 A2 * | | 4/2009 | ........... C07D 403/04 |
| WO | WO-2014181287 A1 * | | 11/2014 | ........... C07D 413/02 |

OTHER PUBLICATIONS

Emmadi; Bioorg. Med. Chem. Lett. 2015, 25, 2918-2922. (Year: 2015).*
Furuya; Bioorganic & Medicinal Chemistry Letters 2017, 27, 1233-1236. (Year: 2017).*
Mungalpara; Chem. Sci., 2017, 8, 6005-6013. (Year: 2017).*
You; Bioorganic & Medicinal Chemistry Letters 2016, 26, 5891-5895. (Year: 2016).*
Zheng; Future Med. Chem. 2015, 7, 2485-2505. (Year: 2015).*
Chemical Abstracts STN Registry Database, record for RN 1827558-52-0, Entered into STN on Dec. 11, 2015. (Year: 2015).*
Chemical Abstracts STN Registry Database, Record for RN 919435-36-2, entered on Feb. 6, 2007. (Year: 2007).*

(Continued)

*Primary Examiner* — Daniel R Carcanague
(74) *Attorney, Agent, or Firm* — Parker Highlander PLLC

(57) ABSTRACT

The present disclosure provides compounds that may be useful for inhibiting Wnt pathway comprising compounds of the formula: (Ia) or (Ib) wherein the variables are as defined herein. In some aspects, the compounds may be used to inhibit the Wnt pathway and used to treat cancer, myocardial infarction, osteopetrosis, or used in the maturation of a precursor cell to a mature cell. Also provided herein in are pharmaceutical compositions of the compounds described herein.

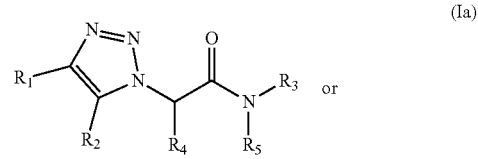

(Ia)

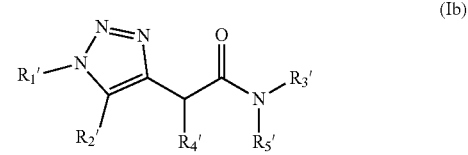

(Ib)

19 Claims, 1 Drawing Sheet

(56) References Cited

OTHER PUBLICATIONS

Chen et al., "Small molecule-mediated disruption of Wnt-dependent signaling in tissue regeneration and cancer," *Nat. Chem. Biol.*, 5(2):100-107, 2009.

Cheng et al., "Discovery of Pyridinyl Acetamide Derivatives as Potent, Selective, and Orally Bioavailable Porcupine Inhibitors," *ACS Med. Chem. Lett.*, 7(7):676-680, 2016.

Clevers and Nusse, "Wnt/β-catenin signaling and disease," *Cell*, 149(6):1192-1205, 2012.

Dodge et al., "Diverse chemical scaffolds support direct inhibition of the membrane-bound O-acyltransferase porcupine," *J. Biol. Chem.*, 287(27):23246-23254, 2012.

Dong et al., "Exploration of the linkage elements of porcupine antagonists led to potent Wnt signaling pathway inhibitors," *Bioorg. Med. Chem.*, 23:6855-6868, 2015.

Duraiswamy et al., "Discovery and Optimization of a Porcupine Inhibitor," *J. Med. Chem.*, 58(15):5889-5899, 2015.

Liu et al., "Targeting Wnt-driven cancer through the inhibition of Porcupine by LGK974," *Proc. Natl. Acad. Sci. USA*, 110(50):20224-20229, 2013.

Lum & Chen, "Chemical Disruption of Wnt-dependent Cell Fate Decision-making Mechanisms in Cancer and Regenerative Medicine," *Curr. Med. Chem.*, 22(35):4091-4103, 2015.

Madan et al., "Wnt addiction of genetically defined cancers reversed by PORCN inhibition," *Oncogene*, 35(17):2197-2207, 2016.

PCT International Preliminary Report on Patentability issued in International Application No. PCT/US2017/049634, dated Mar. 14, 2019.

PCT International Search Report and Written Opinion issued in International Application No. PCT/US2017/049634, dated Dec. 22, 2017.

Poulsen et al., "Pharmacophore Model for Wnt/Porcupine Inhibitors and Its Use in Drug Design," *J. Chem. Inf. Model*, 55(7):1435-1448, 2015.

PubChem SID 10276020, created Mar. 14, 2006, retrieved Oct. 2, 2017.

Wang et al., "The development of highly potent inhibitors for porcupine," *J. Med. Chem.*, 56:2700-2704, 2013.

Zimmerman et al., "Targeting Wnt pathways in disease," *Cold Spring Harb. Perspect. Biol.*, 4(11):a008086, 2012.

\* cited by examiner

DISUBSTITUTED AND TRISUBSTITUTED 1,2,3-TRIAZOLES AS WNT INHIBITORS

This application is a national phase application under 35 U.S.C. § 371 of International Application No. PCT/US2017/049634, filed Aug. 31, 2017, which claims the benefit of priority to U.S. Provisional Application No. 62/382,485, filed on Sep. 1, 2016, the entire contents of which are hereby incorporated by reference.

This invention was made with government support under grant number 1R01CA168761, awarded by the National Institutes of Health. The government has certain rights in the invention.

BACKGROUND

1. Field

The present disclosure generally relates to the fields of molecular biology and medicine. More particularly, the present disclosure provides compounds useful as inhibitors of the Wnt protein pathway.

2. Description of Related Art

Secreted Wnt proteins play essential roles in embryonic development and adult tissue homeostasis (Lum & Chen, 2015; Clevers & Nusse, 2012 and Zimmerman et al., 2012). Although aberrant Wnt signaling is frequently associated with the formation and metastasis of tumors, there is no drug targeting this cellular signaling pathway approved for clinical use. The Wnt acyltransferase Porcupine (Porcn) has been previously identified and supports Wnt secretion (Hofmann 2000) to be highly druggable (Chen et al., 2009 and Dodge et al., 2012). Previously, several new classes of small-molecule Porcn inhibitors have been developed by the inventors and others (Chen et al., 2009; Dodge et al., 2012; Wang et al., 2013; Liu et al., 2013; Cheng et al., 2016; Duraiswamy et al., 2015; Madan et al., 2016; Poulsen et al., 2015; Dong et al., 2015 and WO 2016/055786). Four classes of small-molecule Porcn inhibitors (e.g., 1-4) were identified from a high-throughput screen (HTS) (FIG. 1) (Chen et al., 2009 and Dodge et al., 2012). While these compounds provide initial starting points for further development, the development of compounds with improved activity and pharmacokinetic properties remains an important question.

SUMMARY

The present disclosure generally provides compounds of the formula:

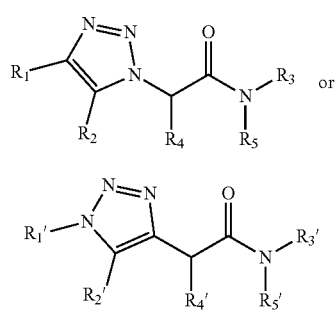

wherein:
- $R_1$ and $R_1'$ are each independently $aryl_{(C \leq 18)}$, $heteroaryl_{(C \leq 18)}$, or a substituted version of either group;
- $R_2$ and $R_2'$ are each independently hydrogen, $aryl_{(C \leq 18)}$, substituted $aryl_{(C \leq 18)}$, $heteroaryl_{(C \leq 18)}$, or substituted $heteroaryl_{(C \leq 18)}$;
- $R_3$ and $R_3'$ are each independently —X—Y;
wherein:
  - X is $arenediyl_{(C \leq 18)}$, substituted $arenediyl_{(C \leq 18)}$, $heteroarenediyl_{(C \leq 18)}$, or substituted $heteroarenediyl_{(C \leq 18)}$;
  - Y is $aryl_{(C \leq 12)}$, $heteroaryl_{(C \leq 12)}$, $heterocycloalkyl_{(C \leq 12)}$, or a substituted version of these three groups;
- $R_4$ and $R_4'$ are each independently hydrogen, $alkyl_{(C \leq 12)}$, or substituted $alkyl_{(C \leq 12)}$; and
- $R_5$ and $R_5'$ are each independently hydrogen, $alkyl_{(C \leq 12)}$, or substituted $alkyl_{(C \leq 12)}$;

or a pharmaceutically acceptable salt thereof. In some embodiments, the compound is a compound of formula Ia. In other embodiments, the compound is a compound of formula Ib. In other embodiments, the compounds are further defined as a compound of formula Ib, wherein:
- $R_4'$ is hydrogen, $alkyl_{(C \leq 8)}$, or substituted $alkyl_{(C \leq 8)}$; and
- $R_5'$ is hydrogen, $alkyl_{(C \leq 8)}$, or substituted $alkyl_{(C \leq 8)}$;

or a pharmaceutically acceptable salt thereof. The compounds may be further defined as:

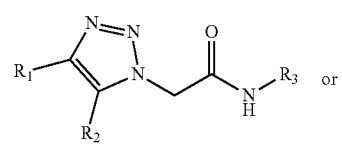

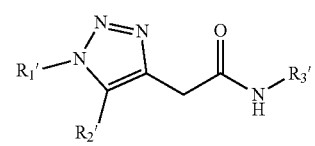

wherein:
- $R_1$ and $R_1'$ are each independently $aryl_{(C \leq 18)}$, $heteroaryl_{(C \leq 18)}$, or a substituted version of either group;
- $R_2$ and $R_2'$ are each independently hydrogen, $aryl_{(C \leq 18)}$, substituted $aryl_{(C \leq 18)}$, $heteroaryl_{(C \leq 18)}$, or substituted $heteroaryl_{(C \leq 18)}$; and
- $R_3$ and $R_3'$ are each independently —X—Y;
wherein:
  - X is $arenediyl_{(C \leq 18)}$, substituted $arenediyl_{(C \leq 18)}$, $heteroarenediyl_{(C \leq 18)}$, or substituted $heteroarenediyl_{(C \leq 18)}$;
  - Y is $aryl_{(C \leq 12)}$, $heteroaryl_{(C \leq 12)}$, $heterocycloalkyl_{(C \leq 12)}$, or a substituted version of these three groups;

or a pharmaceutically acceptable salt thereof. In some embodiments, the compounds are further defined as a compound of formula IIa. In other embodiments, the compounds are further defined as a compound of formula IIb. The compounds may be further defined as a compound of formula IIa, wherein:
- $R_1$ is $heteroaryl_{(C \leq 18)}$ or substituted $heteroaryl_{(C \leq 18)}$;

or a pharmaceutically acceptable salt thereof. The compound may be further defined as a compound of formula IIb, wherein:

$R_1'$ is heteroaryl$_{(C≤18)}$ or substituted heteroaryl$_{(C≤18)}$;
or a pharmaceutically acceptable salt thereof. In some embodiments, the compounds are further defined as a compound of formula IIa, wherein:

$R_2$ is aryl$_{(C≤18)}$ or substituted aryl$_{(C≤18)}$; and or a pharmaceutically acceptable salt thereof. In other embodiments, the compounds are further defined as a compound of formula IIb, wherein:

$R_2'$ is aryl$_{(C≤18)}$ or substituted aryl$_{(C≤18)}$; and or a pharmaceutically acceptable salt thereof.

In some embodiments, $R_1$ or $R_1'$ is heteroaryl$_{(C≤12)}$ or substituted heteroaryl$_{(C≤12)}$. $R_1$ or $R_1'$ may be heteroaryl$_{(C≤12)}$ such as 2-pyridyl, 3-pyridyl, 4-pyridyl, or 3-methyl-4-pyridyl. In some embodiments, $R_1$ or $R_1'$ is 4-pyridyl. Alternatively, $R_1$ or $R_1'$ may be substituted heteroaryl$_{(C≤12)}$ such as 3-trifluoromethyl-4-pyridyl. In other embodiments, $R_1$ or $R_1'$ is aryl$_{(C≤12)}$ or substituted aryl$_{(C≤12)}$. $R_1$ or $R_1'$ may be aryl$_{(C≤12)}$ such as phenyl. Alternatively, $R_1$ or $R_1'$ is substituted aryl$_{(C≤12)}$ such as 4-methoxyphenyl or 2-trifluoromethylphenyl.

In some embodiments, $R_2$ or $R_2'$ is aryl$_{(C≤12)}$ or substituted aryl$_{(C≤12)}$. $R_2$ or $R_2'$ may be aryl$_{(C≤12)}$ such as phenyl, 2-methylphenyl, 3-methylphenyl, or 1-naphthyl. Alternatively, $R_2$ or $R_2'$ may be substituted aryl$_{(C≤12)}$ such as 4-methoxyphenyl, 4-(ethyl carboxy)phenyl, 4-cyanophenyl, 4-trifluoromethylphenyl, 4-fluorophenyl, or 2-methoxyphenyl.

In some embodiments, X is arenediyl$_{(C≤18)}$ or substituted arenediyl$_{(C≤18)}$. X is arenediyl$_{(C≤18)}$ such as benzenediyl. In one embodiment, X is benzene-1,4-diyl. In other embodiments, X is heteroarenediyl$_{(C≤18)}$ or substituted heteroarenediyl$_{(C≤18)}$ such as thiazol-2,5-diyl, pyrid-2,5-diyl, or pyrimid-2,5-diyl. In some embodiments, Y is aryl$_{(C≤12)}$ or substituted aryl$_{(C≤12)}$. Y may be aryl$_{(C≤12)}$ such as phenyl. In other embodiments, Y is heteroaryl$_{(C≤12)}$ or substituted heteroaryl$_{(C≤12)}$. Y may be heteroaryl$_{(C≤12)}$ such as 5-pyrimidyl, 2-pyridinyl, 3-pyridinyl, 4-pyridinyl, 2-furanyl, 3-furanyl, 2-thienyl, or 3-thienyl. In other embodiments, Y is heterocycloalkyl$_{(C≤12)}$ or substituted heterocycloalkyl$_{(C≤12)}$. Y may be heterocycloalkyl$_{(C≤12)}$ such as N-piperidinyl.

In some embodiments, the compounds are further defined as:

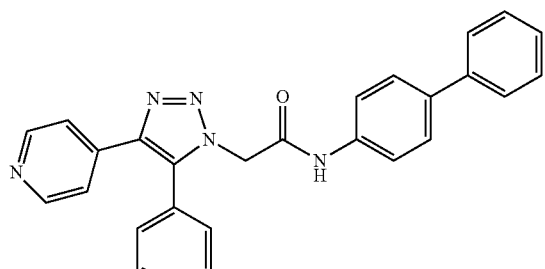

,

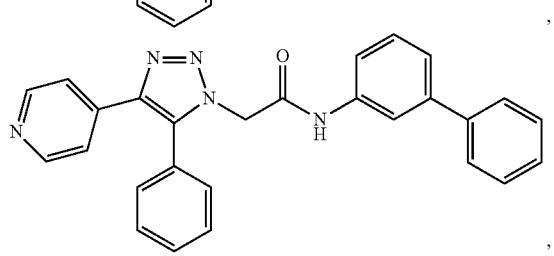

,

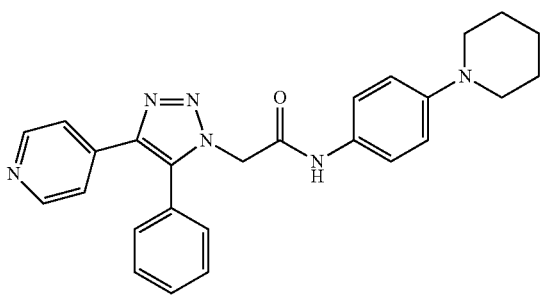

,

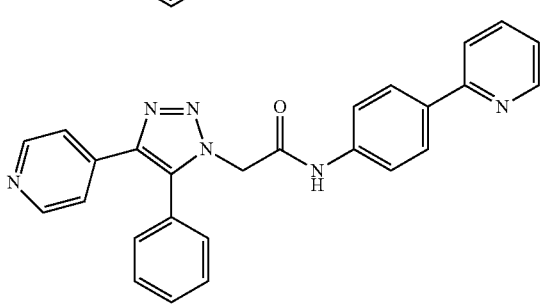

,

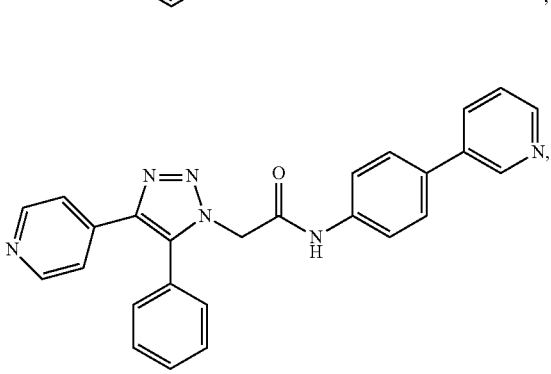

,

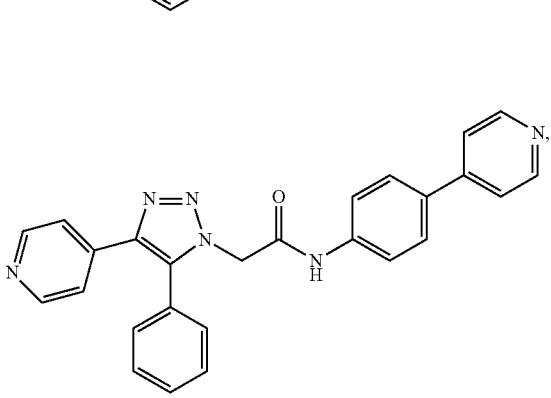

,

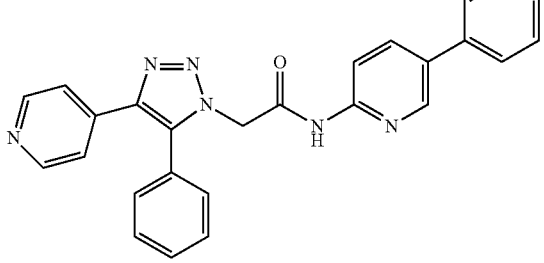

,

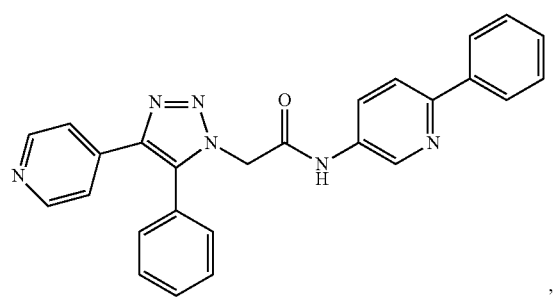
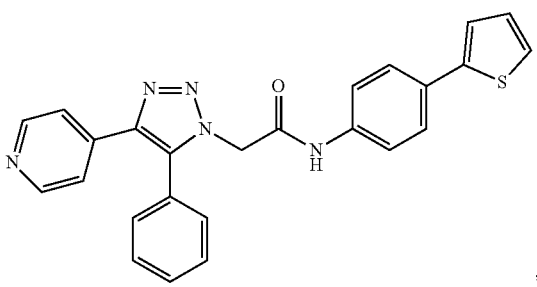

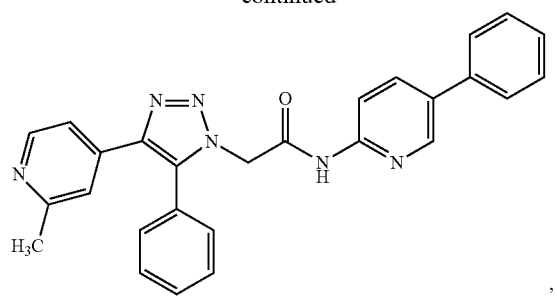
,
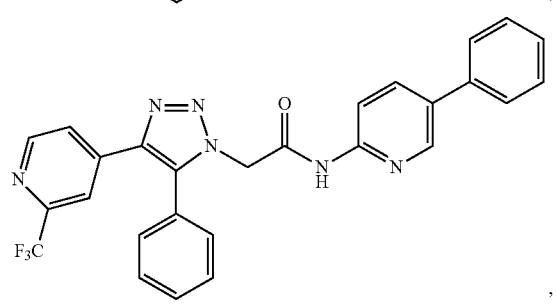
,
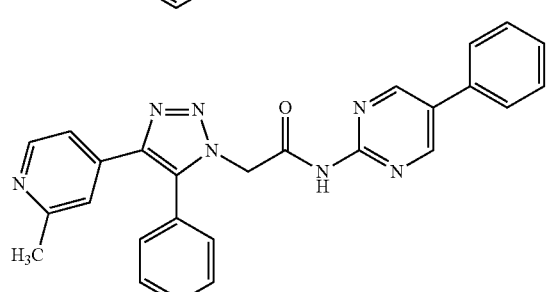
,
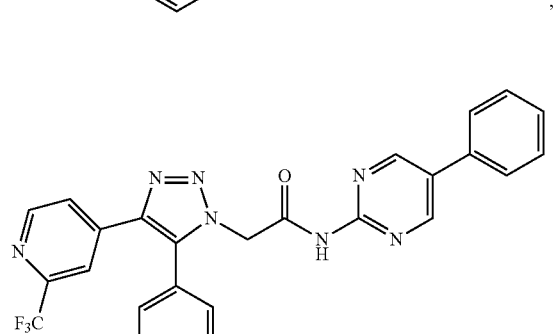
,
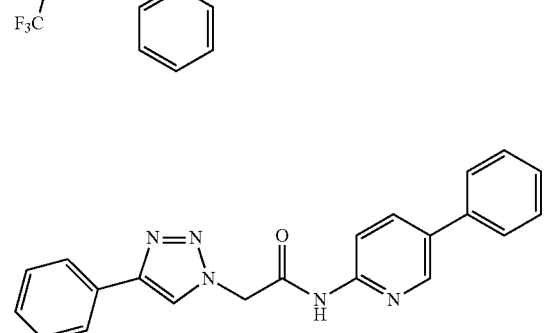
,
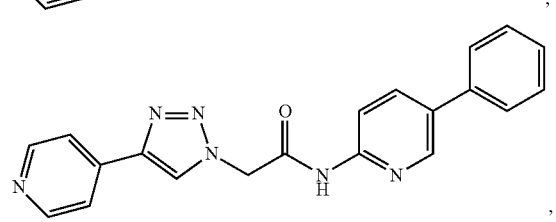
,
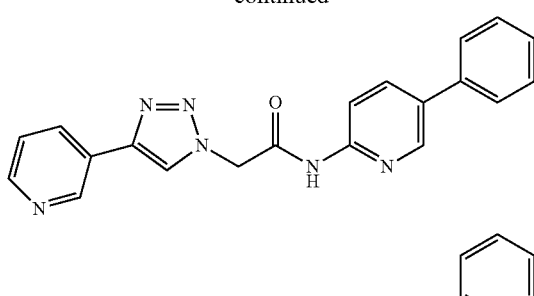
,
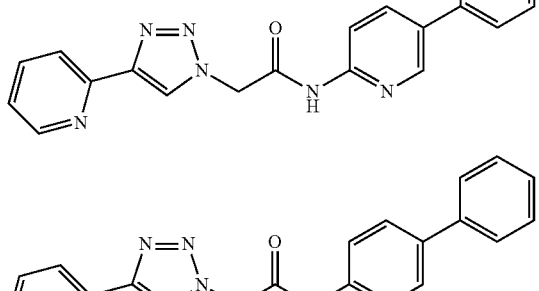
,
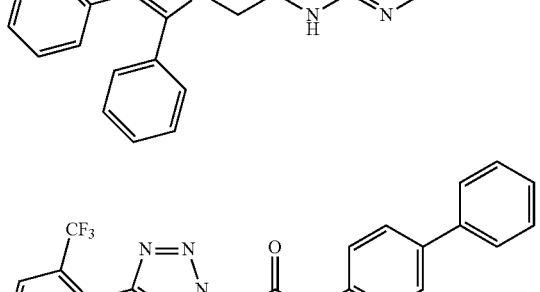
,
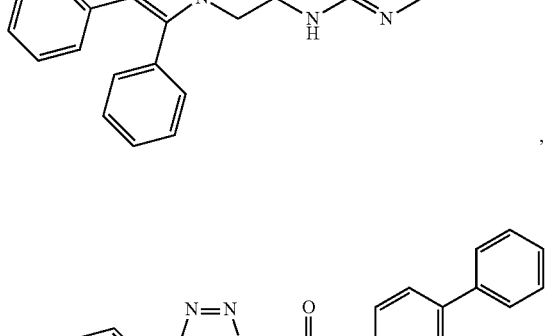
,
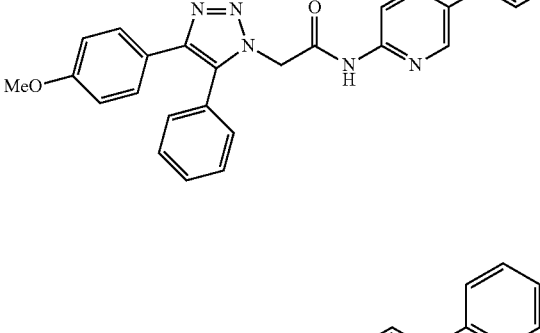
,
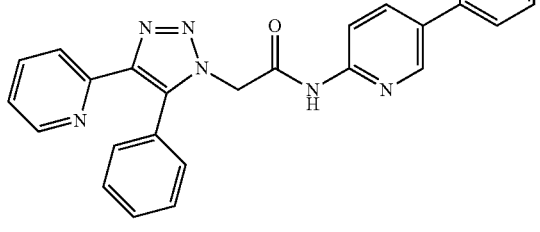
,

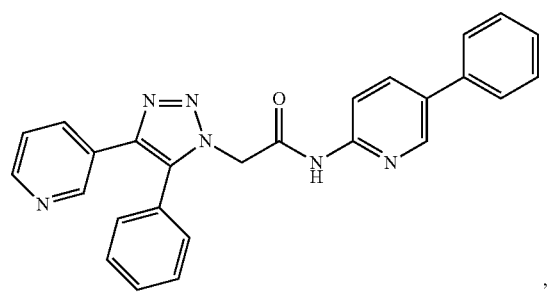
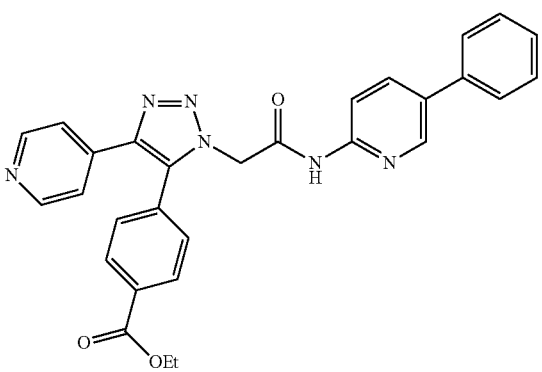
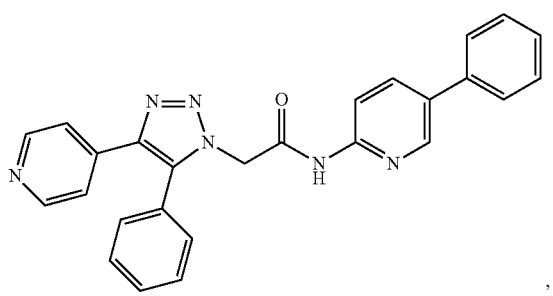 [SMILES: CC(C(=O)Nc1ccc(-c2ccccc2)cn1)n1nnc(-c2ccncc2)c1-c1ccccc1]
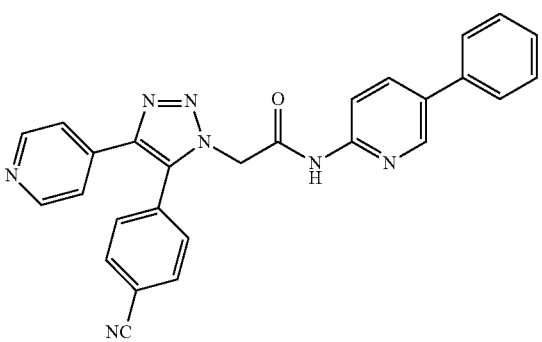
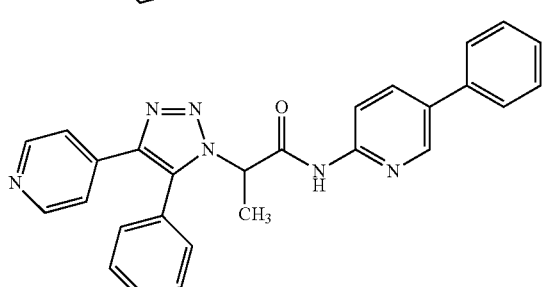
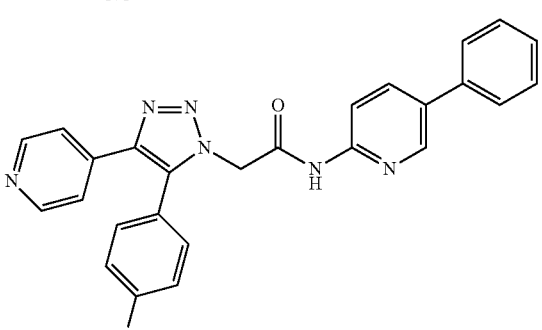
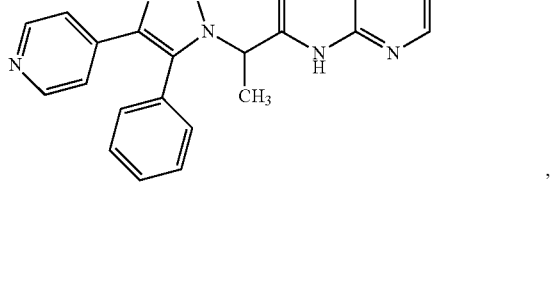
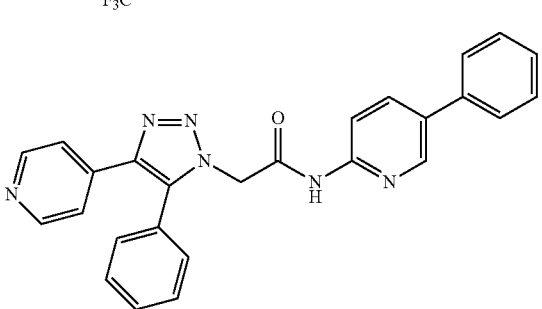
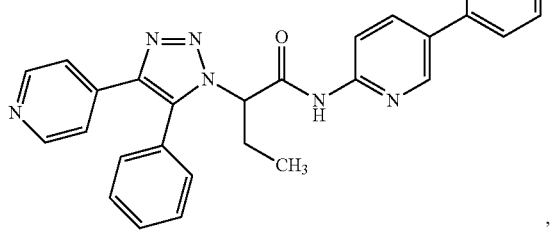
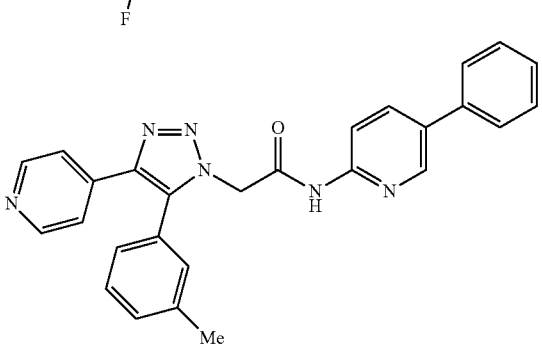
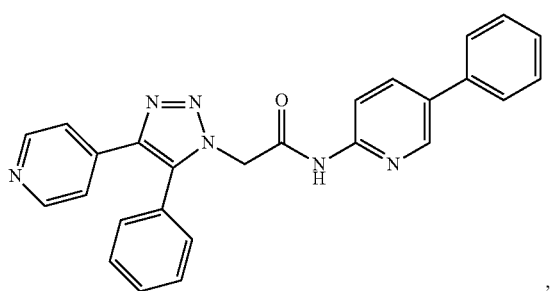

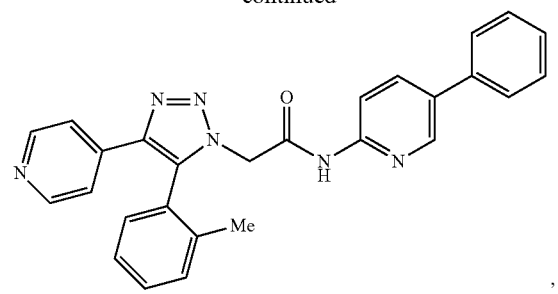
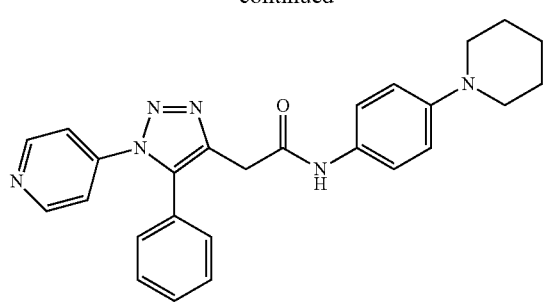
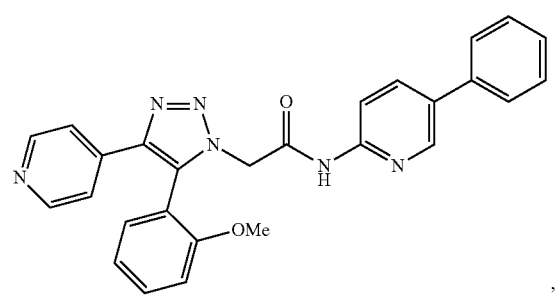
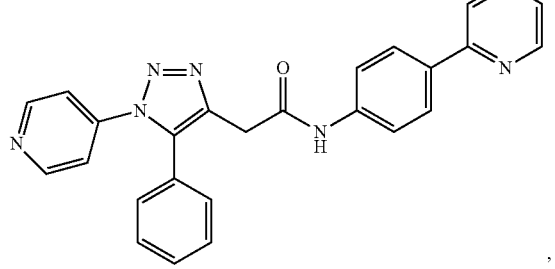
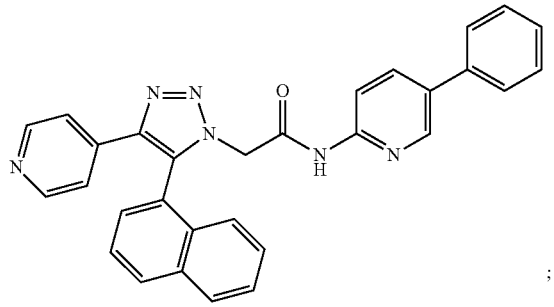
or a pharmaceutically acceptable salt thereof. In other embodiments, the compounds are further defined as:
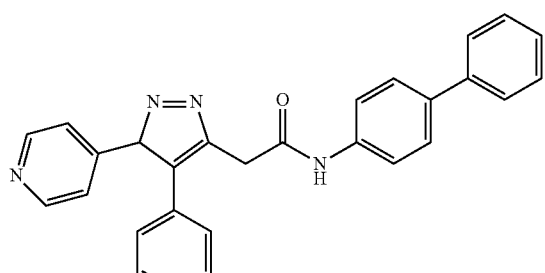
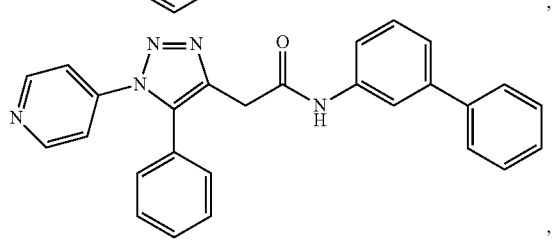

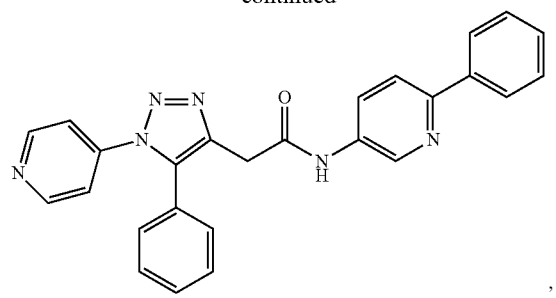
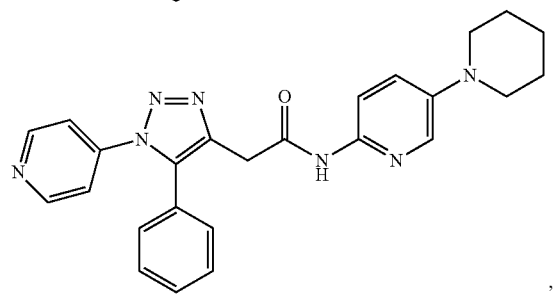
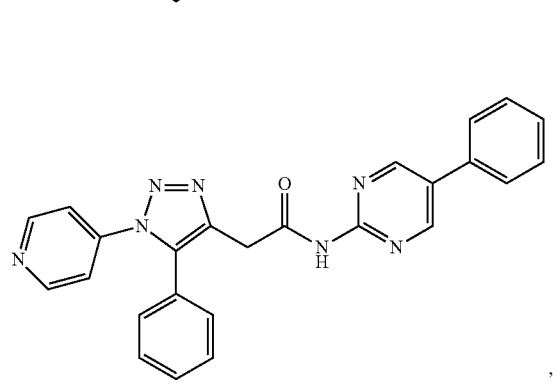
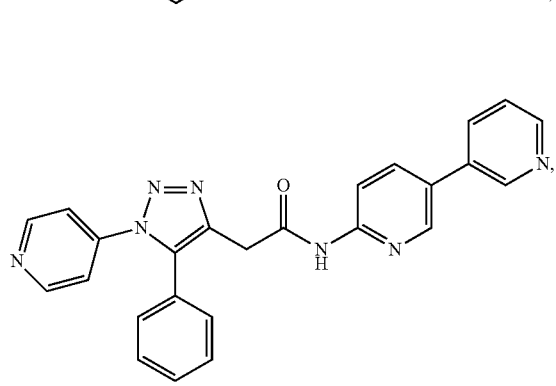
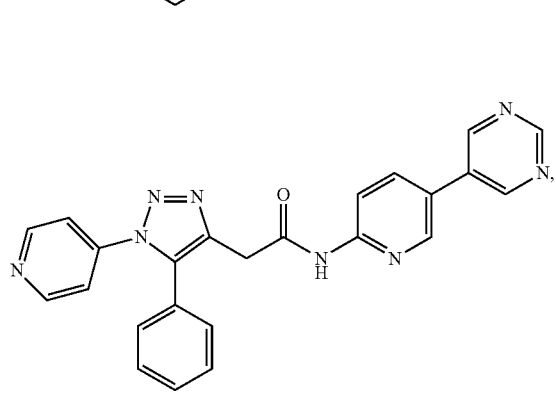
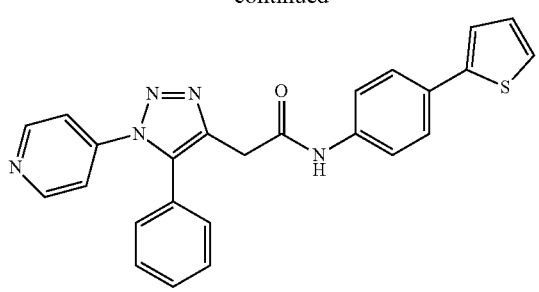
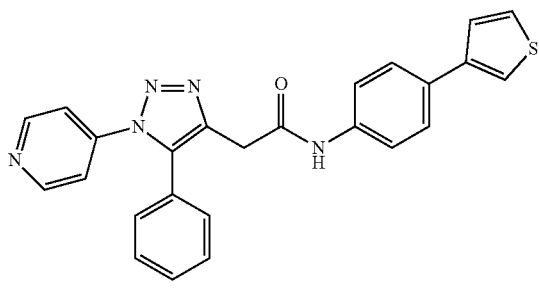
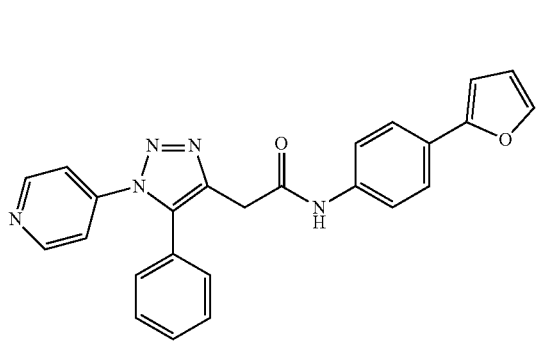
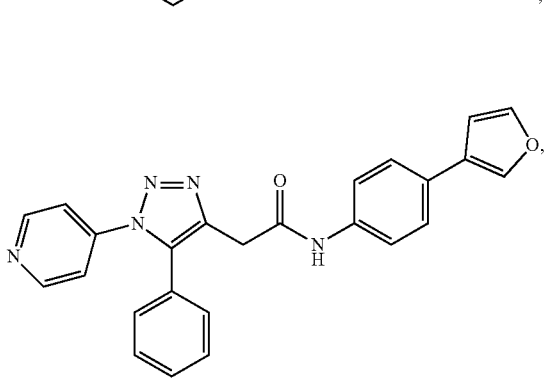
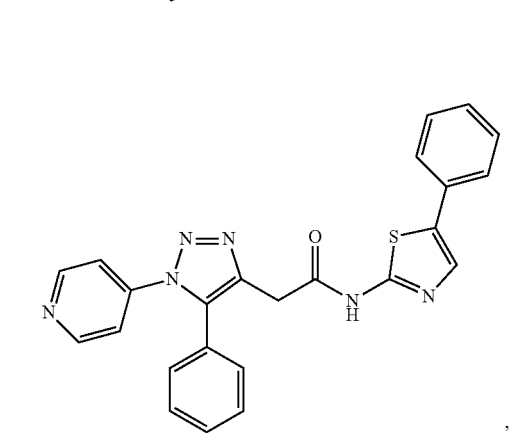

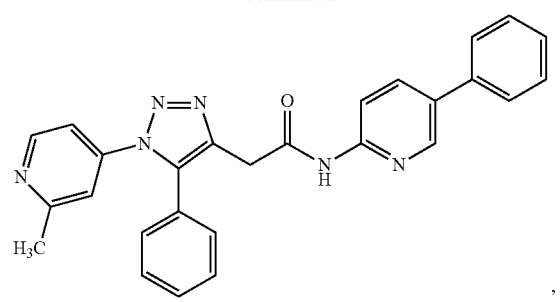
,
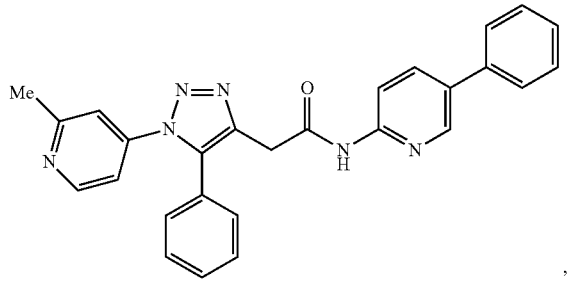 [SMILES: Cc1cc(-n2nnc(CC(=O)Nc3ccc(-c4ccccc4)cn3)c2-c2ccccc2)ccn1]
,
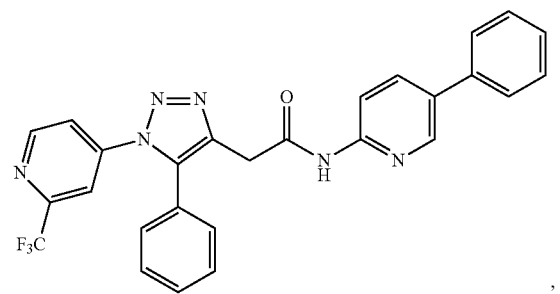
,
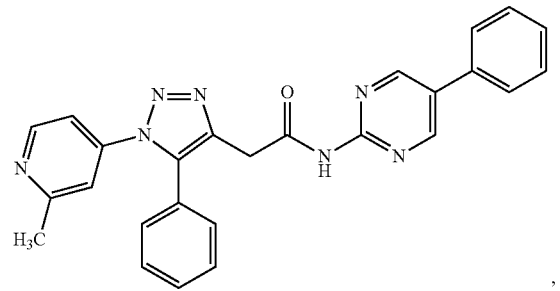
,
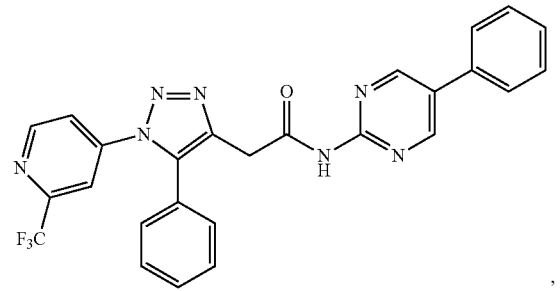
,
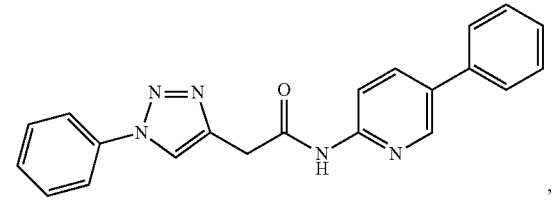
,
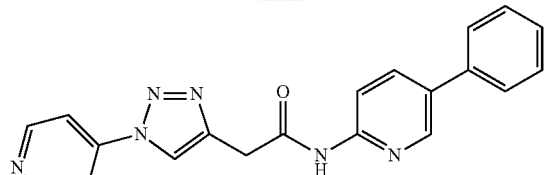
,
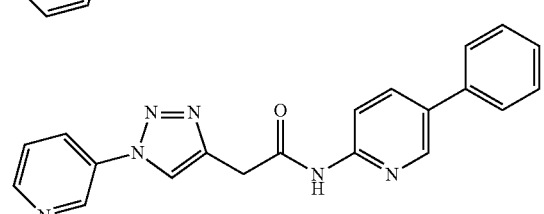
,
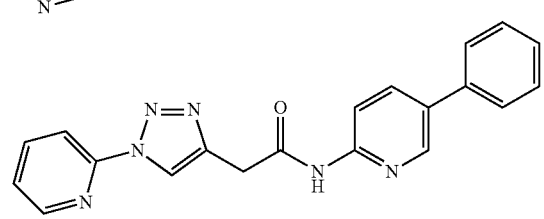
,
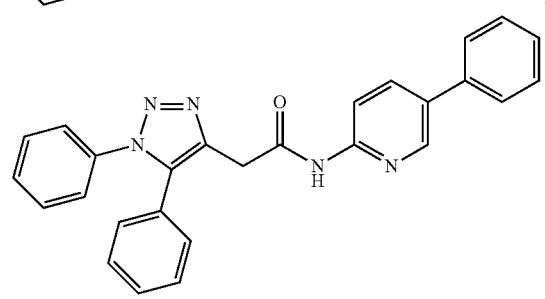
,
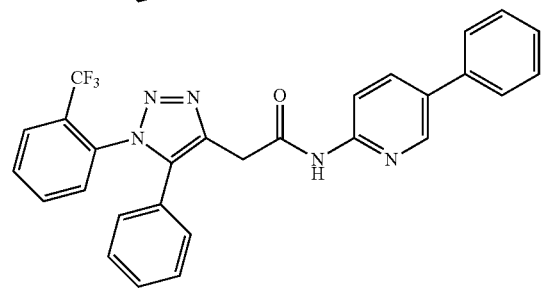
,
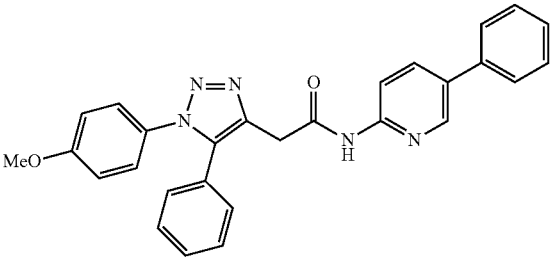
,
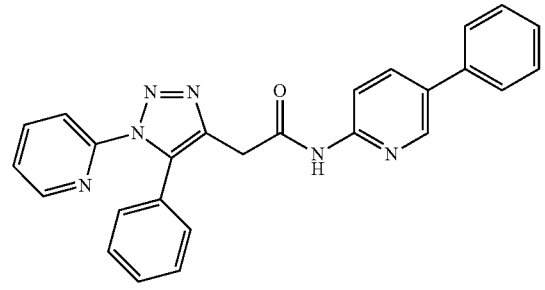
,

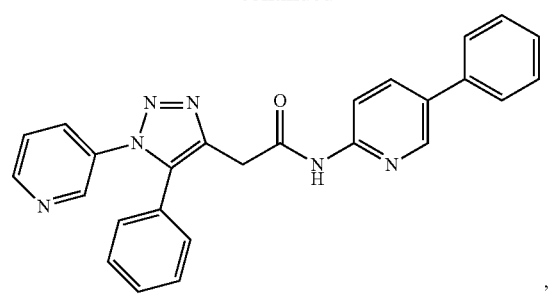
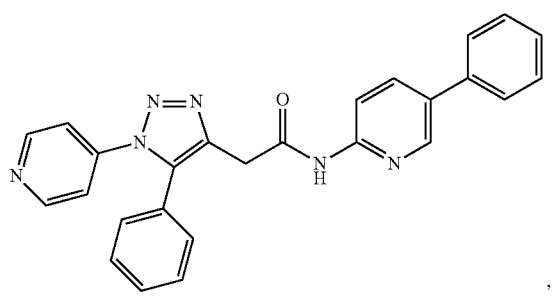
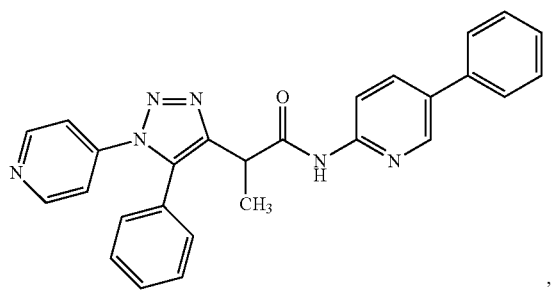 [SMILES: CC(C(=O)Nc1ccc(-c2ccccc2)cn1)c1nnn(-c2ccncc2)c1-c1ccccc1]
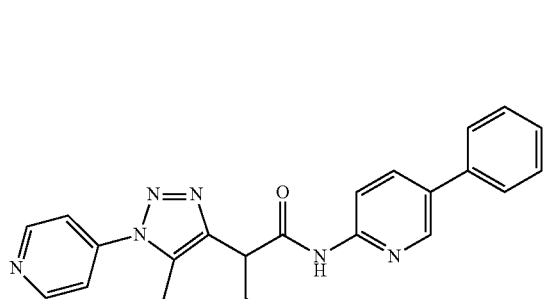
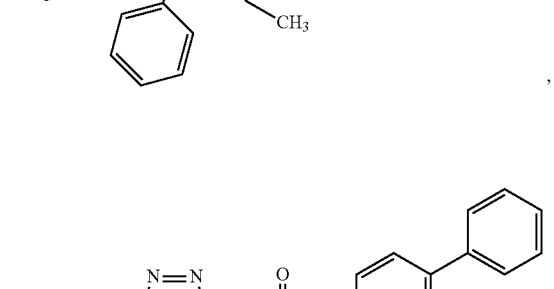
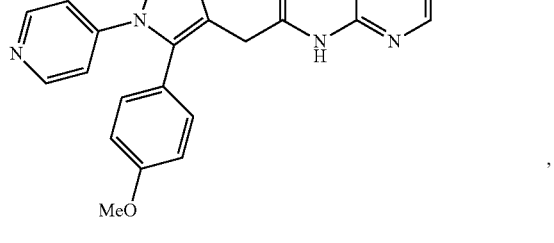
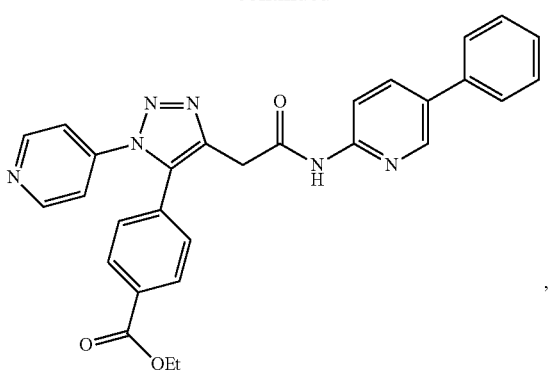
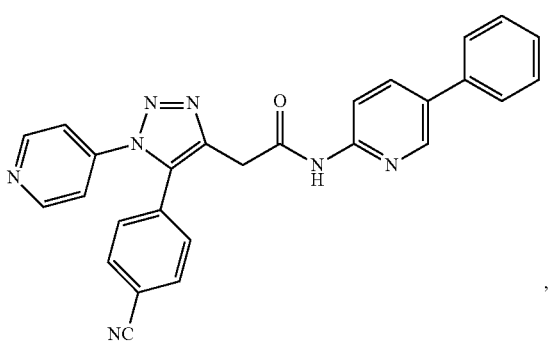
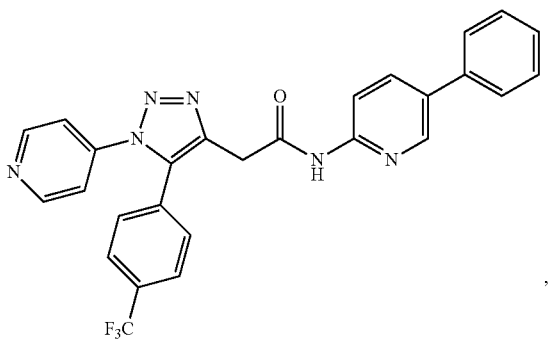
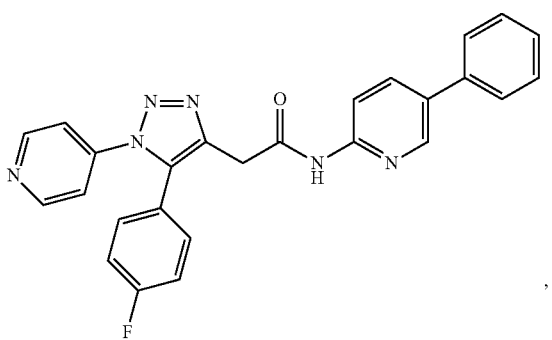
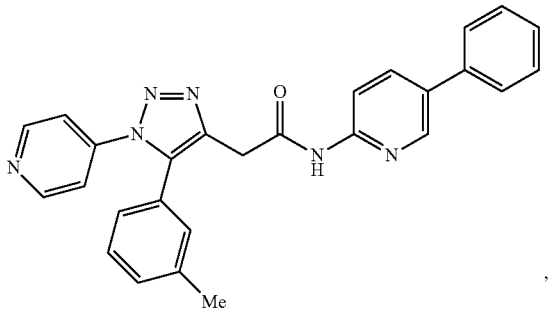

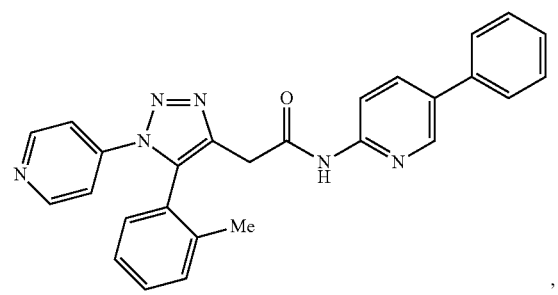
,
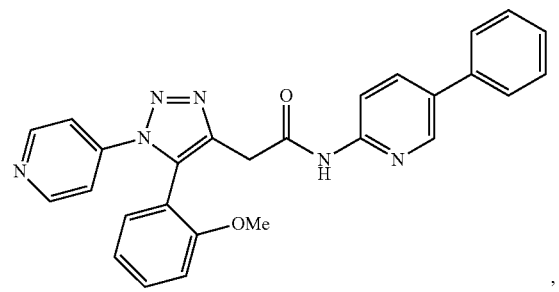
, or
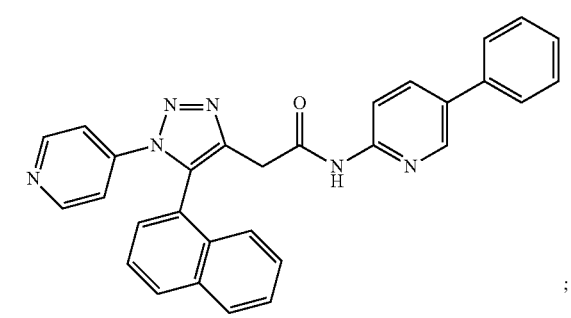
;
or a pharmaceutically acceptable salt thereof.
In some embodiments, the compounds are further defined as:
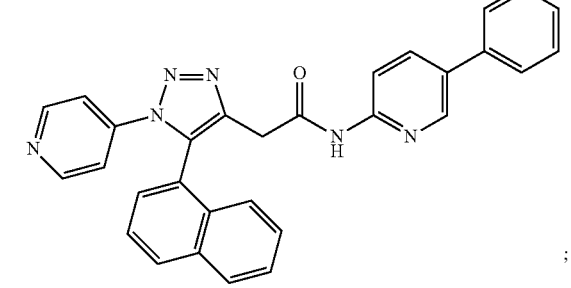
,
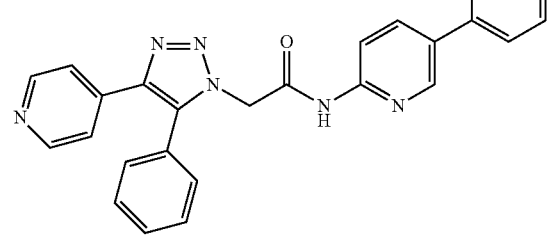
,
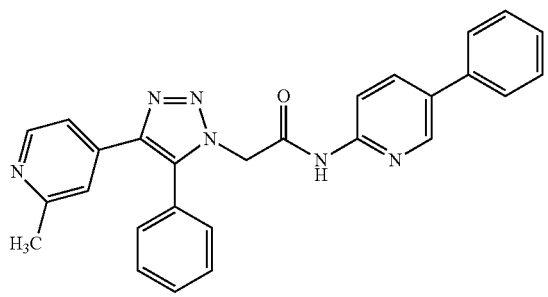
,
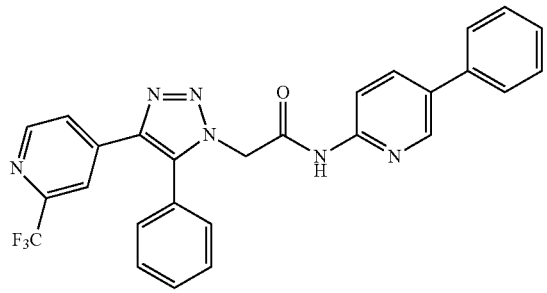
,
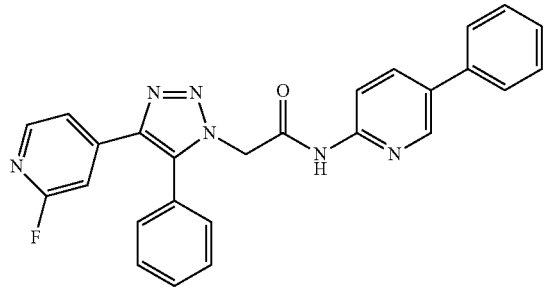
,
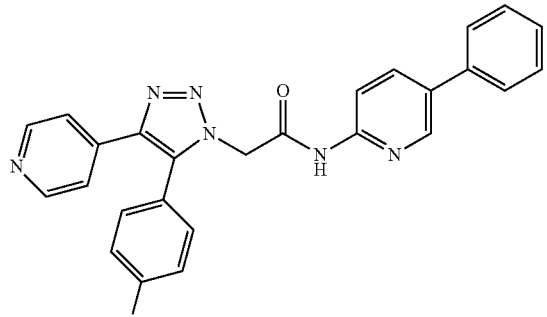
,
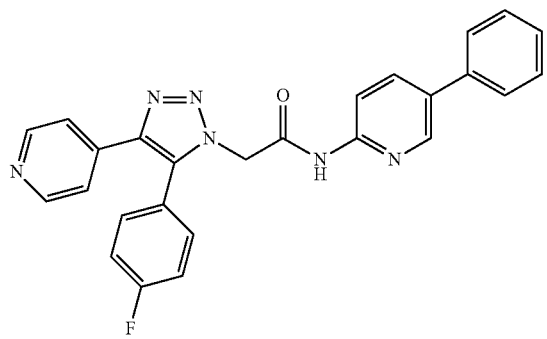
,

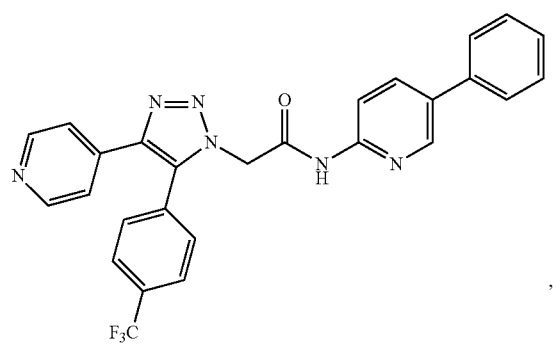
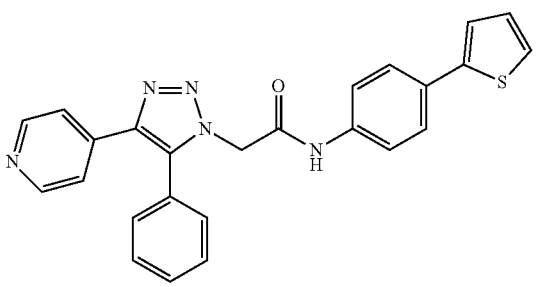
or a pharmaceutically acceptable salt thereof. In some embodiments, the compounds are further defined as:

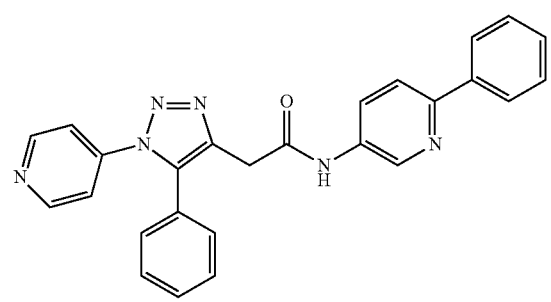
,
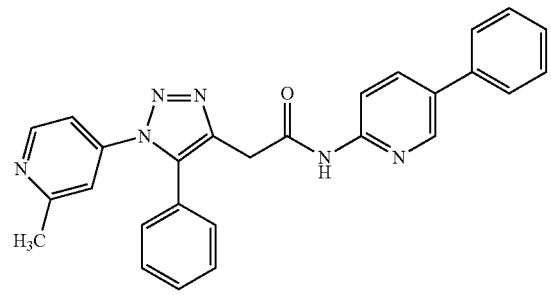
,
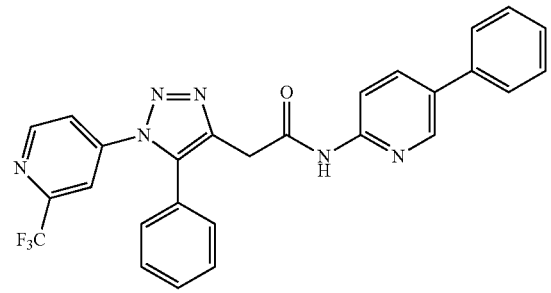
,
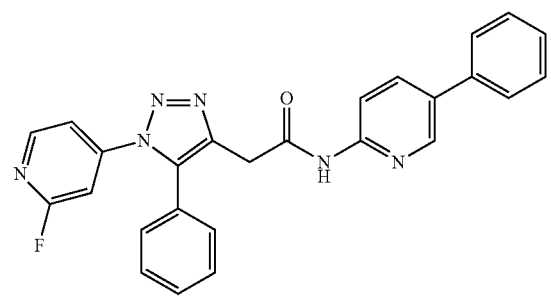
,
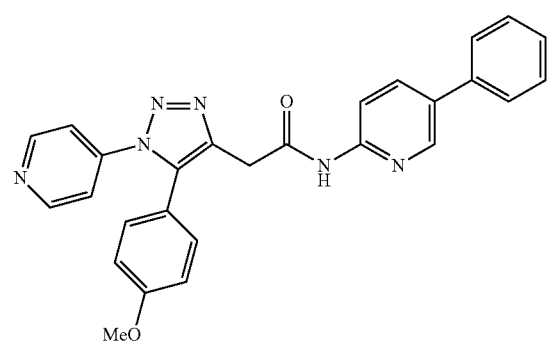
,
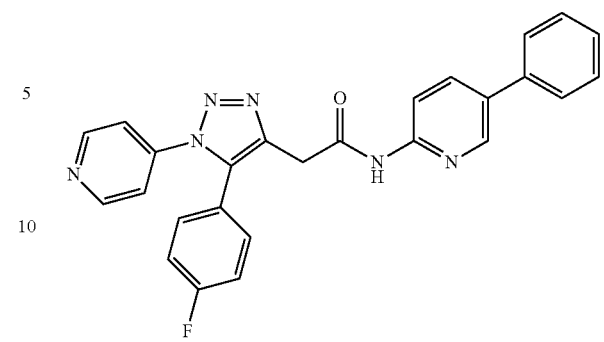
,
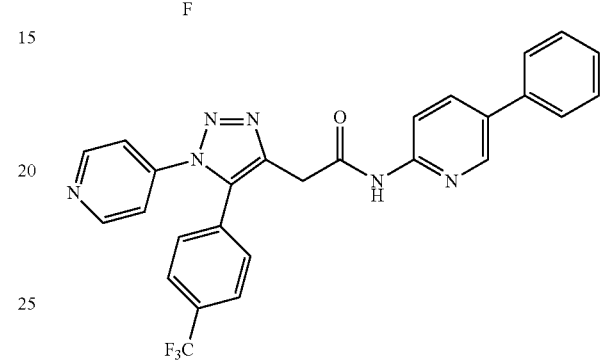
,
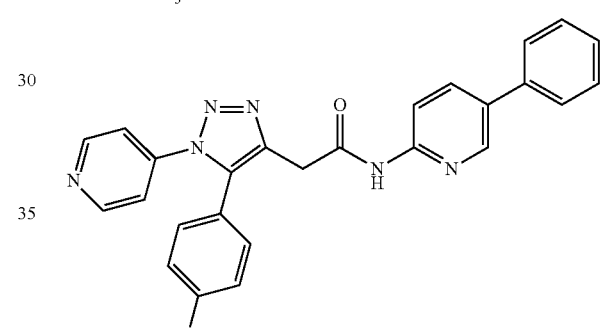
,
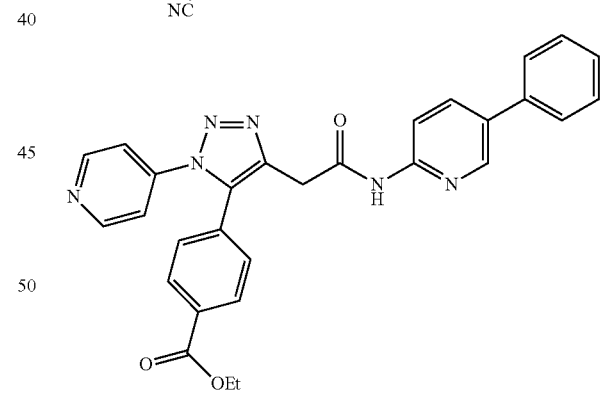
,
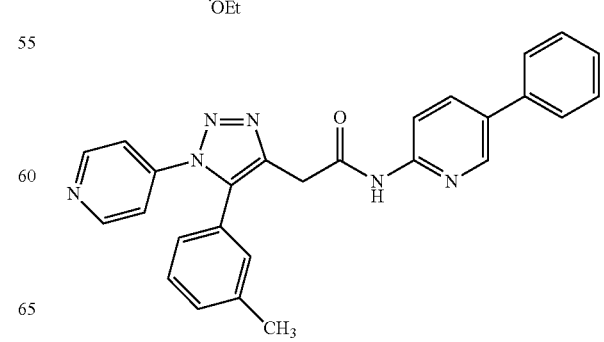
, -continued
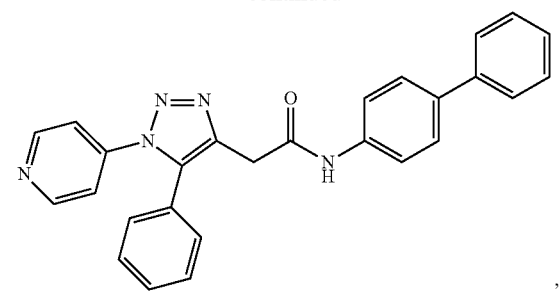
,
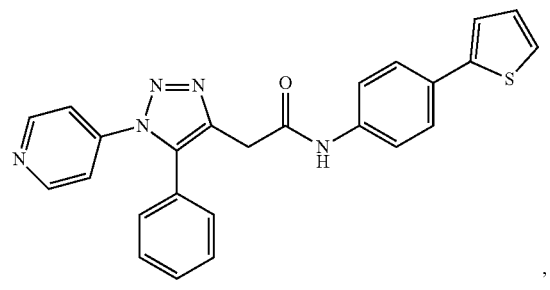
,
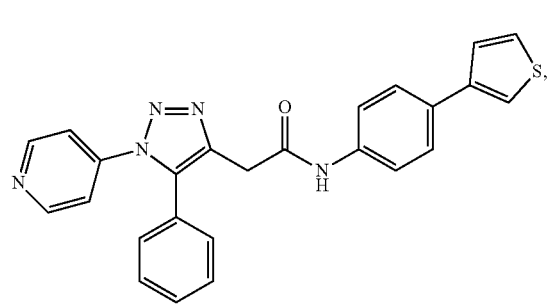
,
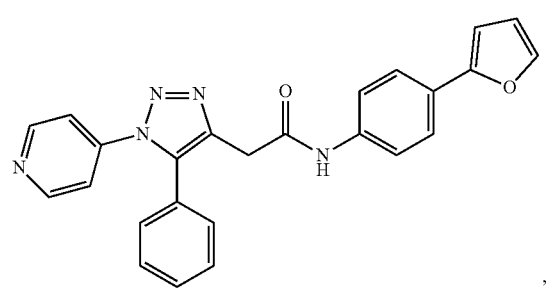
, or
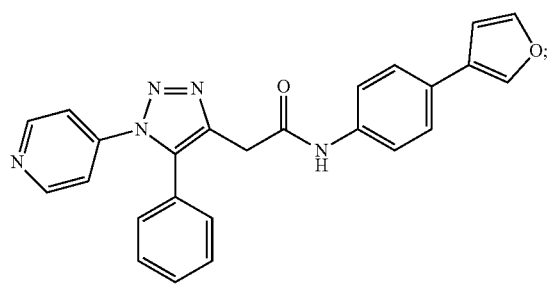
or a pharmaceutically acceptable salt thereof. In some embodiments, the compounds are further defined as:
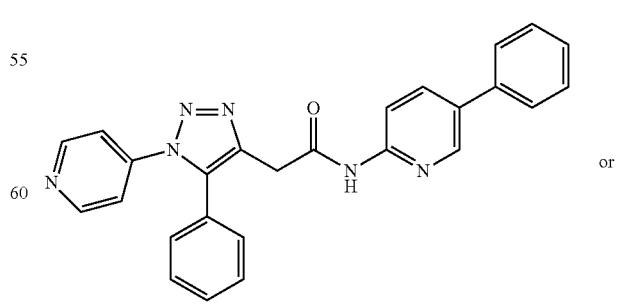
or a pharmaceutically acceptable salt thereof. In some embodiments, the compounds are further defined as:

-continued

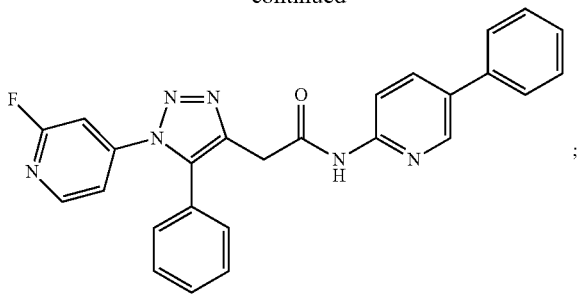

or a pharmaceutically acceptable salt thereof. The compound may be further defined as:

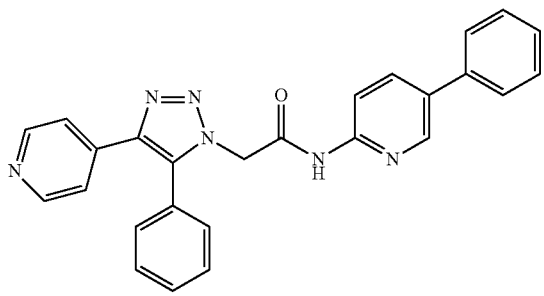 [SMILES: O=C(Cn1nnc(-c2ccncc2)c1-c1ccccc1)Nc1ccc(-c2ccccc2)cn1]

or a pharmaceutically acceptable salt thereof.

In another embodiment, the present disclosure provides pharmaceutical compositions comprising:
(A) a compound described herein; and
(B) an excipient.

In some embodiments, the pharmaceutical compositions are formulated for administration: orally, intraadiposally, intraarterially, intraarticularly, intracranially, intradermally, intralesionally, intramuscularly, intracardially, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctivally, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion. The pharmaceutical compositions may be formulated for oral administration, topical administration, intraarterial administration, intracardiac administration, intramuscular administration, intrapericardial administration, intraperitoneal administration, intratumoral administration, or intravenous administration. The pharmaceutical composition may be formulated as a unit dose.

In yet another aspect, the present disclosure provides methods of treating a disease or disorder in a patient comprising administering to the patient in need thereof a therapeutically effective amount of a compound or composition described herein. The disease or disorder may be cancer. In some embodiments, the cancer is associated with Wnt signaling. The cancer may be colorectal cancer, chronic lymphocytic leukemia, melanoma, glioma, breast cancer, liver cancer, lung cancer, prostate cancer, pancreatic cancer, bladder cancer, head and neck cancer, or acute myeloid leukemia. In some embodiments, the methods may further comprise administering the compound with one or more additional cancer therapy such as another chemotherapeutic compound, radiation therapy, immunotherapy, hormone therapy, toxin therapy, or gene therapy.

In other embodiments, the disease or disorder is a myocardial infarction. The compound may be administered after a myocardial infarction. Alternatively, the disease or disorder may be fibrosis related to aging, non-congenital forms of idiopathic pulmonary fibrosis, or post-injury response to skeletal muscle damage, liver damage, lung damage, nerve damage, or kidney dialysis or damage. In other embodiments, the disease or disorder is degenerative disorder such as osteopetrosis or other disorders associated with increased bone mass, proliferative retinopathy, macular degeneration, arthritis, corneal dystrophies, and Parkinson's disease or other neurodegenerative diseases. The degenerative disorder may be osteopetrosis.

The methods may comprise administering the compound in vivo. Alternatively, the methods comprise administering the compound ex vivo. In some embodiments, the methods comprise administering the compound once. The methods may comprise administering the compound two or more times.

In still yet another aspect, the present disclosure provides methods of inducing differentiation of a precursor cell into a mature cell comprising administering to the precursor cell an effective amount of a compound or composition described herein. The precursor cell may be a stem cell, may be an embryonic stem cell, or may be an induced pluripotent stem cell. The mature cell may be a cardiomyocyte, a dopamine producing neuron, a cortical neuron, an retinal ganglion cell, a chondrocyte, a corneal epithelial cell, pneumocyte, or an aveolar epithelial lung cell. In some embodiments, the mature cell is a cardiomyocyte. In other embodiments, the mature cell is a dopaminergic neuron. Alternatively, the mature cell may be a pneumocyte. In some embodiments, the mature cell is a retinal pigment epithelium cell. The mature cells may be form a tissue such as from a cardiac tissue, a neuronal tissue, a lung tissue, cartilage, or an ocular tissue. The method may be performed in vitro. In some embodiments, the cells are incubated with the compound.

In yet another aspect, the present disclosure provides methods of inhibiting a Wnt protein comprising contacting the Wnt protein with an effective amount of a compound or composition described herein. The Wnt protein may be porcupine. In some embodiments, the contacting is performed in vitro or ex vivo. In other embodiments, the contacting is performed in vivo. The methods of inhibiting Wnt protein may be further defined as a method of inhibiting Wnt response. The methods of inhibiting Wnt protein may be further defined as a method of inhibiting Wnt protein production. The methods of inhibiting Wnt protein may be further defined as a method of inhibiting Wnt protein signaling.

It is specifically contemplated that any limitation discussed with respect to one embodiment of the disclosure may apply to any other embodiment of the disclosure. Furthermore, any composition of the disclosure may be used in any method of the disclosure, and any method of the disclosure may be used to produce or to utilize any composition of the disclosure.

Other objects, features and advantages of the present disclosure will become apparent from the following detailed description. It should be understood, however, that the detailed description and the specific examples, while indicating preferred embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

DESCRIPTION OF ILLUSTRATIVE EMBODIMENTS

Figure 1:
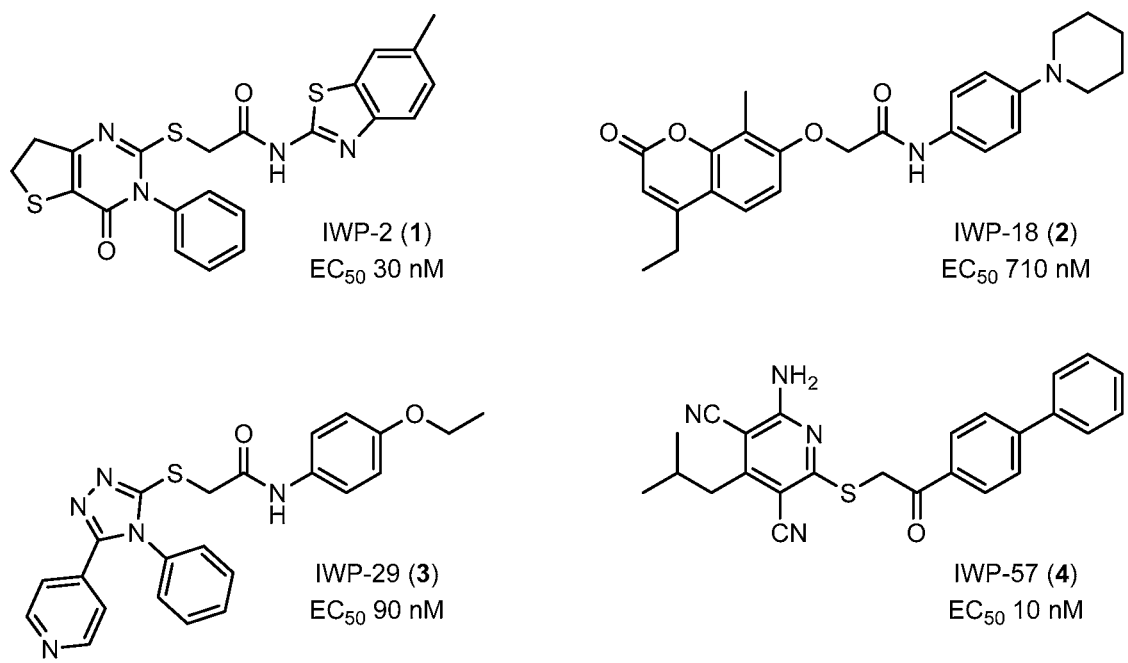
FIG. 1 shows representative structures of the four classes of IWPs (1-4) inhibitors identified from a high throughput screening.

The present disclosure provides compounds that may be used to inhibit the porcupine enzyme and Wnt signaling pathway. The compounds described herein may contain a 1,2,3-triazole core with a bicyclic amide and two aromatic rings attached to the triazole core. These compounds may show improved activity or pharmacokinetic properties. In some aspects, these compounds may be used to treat diseases or disorders or in methods to inhibit the activity of the Wnt signaling pathway. Also provided herein are pharmaceutical compositions of these compounds.

I. THE WNT SIGNAL TRANSDUCTION PATHWAYS

The Wnt gene family encodes secreted ligand proteins that serve key roles in differentiation and development. This family comprises at least 15 vertebrate and invertebrate genes including the *Drosophila* segment polarity gene wingless and one of its vertebrate se homologues, integrated from which the Wnt name derives. As noted above, the Wnt proteins appear to facilitate a number of developmental and homeostatic processes.

The Wnt signalling pathways comprises a number of proteins involved in the transduction of cellular responses to secreted Wnt/wingless signalling proteins. Wnt proteins that control "non-canonical" pathways, such as the Wnt/calcium and planar cell polarity pathways, induce cellular responses that are not dependent upon β-catenin. In the Wnt/β-catenin pathway, the Frizzled receptor then activates Disheveled protein, which blocks the inhibiting action of Zeste-white-3 kinase (or GSK3β in vertebrates, Glycogen Synthase Kinase-3β) upon the Armadillo protein (a β-catenin protein). The β-catenin protein transduces the Wnt signal from the cytoplasm to the nucleus. In the absence of Wnt signalling, β-catenin is constitutively degraded by the proteasome and can be found in a multimeric complex with conductin (or axin), APC (Adenomatous Polyposis *Coli*) and GSK3β. APC mediates the binding of β-catenin to conductin and serves to activate the conductin protein. Conductin acts as a scaffold to assemble the components of the degradation pathway of β-catenin. GSK3β, a serine/threonine kinase, phosphorylates β-catenin, thus stimulating its degradation by the proteasome.

Upon Wnt signalling, GSK3β kinase is inactivated, leading to stabilization of the β-catenin protein. β-Catenin is then released from the multimeric complex and translocates into the nucleus. Once in the nucleus, β-catenin interacts with the LEF/TCF (Lymphoid Enhancer Factor/T-Cell Factor) family of HMG (High Mobility Group) box transcription factors. The LEF/TCF factors are stimulated through interaction with β-catenin to become potent transactivators of a number of genes including c-myc and cyclin D1.

It has recently been found that β-catenin degradation can be promoted by stablising Axin through the inhibition of the poly-ADP-ribose polymerase (PARP) enzymes tankyrase 1 and tankyrase 2, as described in WO 2009/059994 and Huang et al. (2009). Both tankyraseisoforms interact with a highly conserved domain of Axin and stimulate its degradation through the ubiquitin-proteasome pathway. This previously unknown mechanism for stabilising Axin protein, thereby enhancing β-catenin degradation, can be exploited for treating Wnt signaling-related disorders. Axin proteins are essential regulators of a spectrum of physiological processes, including brain oligodendrocyte progenitor cell differentiation for remyelination (Fancy, 2011), and epithelial-to-mesenchymal transition during pulmonary fibrosis (Ulsamer, 2012). Thus, by way of stabilizing Axin proteins, Tankyrase inhibitors may be used as a therapy for remyelination post brain injury and pulmonary fibrosis.

Tankyrase has several binding protein partners, including TRF1, a double-stranded telomeric repeat binding protein (Smith, 1998); NuMA, an essential protein in mitotic spindle assembly (Chang, 2005); IRAP, an integral membrane protein involved in glucose uptake in response to insulin (Chi, 2000); and Mcl-1, a pro-apoptotic protein (Bae, 2003).

By way of its various interacting proteins, tankyrase proteins have been implicated in different biological functions. Tankyrase poly (ADP-ribosyl)ates TRF1, releasing it from telomeres and enhancing telomere access to telomerase. Thus, tankyrase functions as a positive regulator for telomere elongation by telomerase, supported by the findings that long-term overexpression of tankyrase leads to telomere elongation (Cook, 2002). Telomere maintenance by telomerase has been attributed to the uncontrolled proliferation of cancer cells (Hahn, 1999). Tankyrase may be useful as a therapeutic target for cancer therapy by inhibiting the telomere accessibility for telomerase. Tankyrase inhibition could be used as an effective cancer therapy to treat patients with a wide spectrum of cancers, including leukemia, lymphoma, multiple myeloma, lung, and breast cancer.

Tankyrase also plays a role in cell mitosis by: 1) poly (ADP-ribosyl)ating NuMA during mitosis and regulating its functions at spindle poles (Chang, 2005); 2) by regulating spindle assembly and structure (Chang, 2004); and 3) by maintaining sister chromatid resolution at telomeres (Dynek, 2004). Inhibition of tankyrase leads to cell mitotic arrest or senescence, and thus could be exploited for treating diseases that have abnormal mitotic division, such as cancer. Examples include breast, colon, lung, ovarian, leukemia, lymphoma, and melanoma. In addition, tankyrase 1 was identified as a gene required for centrosome clustering, a mechanism that cancer cells with supernumerary centrosomes employs to suppress multipolar mitosis and enable bipolar mitosis (Kwon, 2008). Thus inhibition of tankyrase may be used to treat cancers through centrosome amplification, including both solid and haematological cancers, examples include breast, bladder, lung, colon, and leukemia.

Moreover, one of the cellular localizations of tankyrase is at the Golgi apparatus co-localizing with the glucose transporter GLUT4 vesicles where tankyrase is associated with IRAP, and tankyrase is implicated in the regulation of GLUT4 trafficking in adipocytes (Chi, 2000). Tankyrase-deficient mice exhibit reduced adiposity and increased energy expenditure by increases in both fatty acid oxidation and insulin-stimulated glucose utilization (Yeh, 2009). This supports tankyrase involvement in energy homeostasis in mammals and inhibiting tankyrase can be exploited for treating metabolic diseases, such as obesity.

II. THERAPEUTIC IMPLICATIONS OF WNT-CONTROLLED SIGNAL TRANSDUCTION PATHWAYS

A. Tumors

As noted above, evidence suggests that targeting the Wnt-mediated signal transduction pathways would be therapeutically useful in a broad range of diseases (Barker and Clevers, 2006) (Veeman et al., 2003). Aged mice or mice that exhibit premature stem cell senescence that are treated with extracellular protein inhibitors of Wnt pathways exhibit improved regenerative capacity in various tissues (Brack et al., 2007; Liu et al., 2007). Mutations leading to constitutive activation of the Wnt pathway are critical events in a variety of human cancers including colon cancer, melanoma, hepatocellular carcinoma and others. The end result of constitutive activation of the Wnt/β-catenin pathway is a dramatic increase in the level of β-catenin protein in the cytoplasm. Inappropriate stabilization of β-catenin, leading to increased levels of the protein, can be caused by mutations in a variety of proteins in the Wnt signalling pathway. Blockade of the Wnt/β-catenin pathway in a variety of cancers using either genetic or chemical approaches been shown to abrogate aberrant cell growth (Barker and Clevers, 2006). Furthermore, inhibition of this pathway may directly influence the cells that sustain cancer cell growth and enable metastasis, and that are thought to be resistant to traditional chemotherapeutic agents (Ailles and Weissman, 2007).

Aberrant Wnt-mediated pathway responses, sustained by genetic changes that result either in altered Wnt ligand activity or in altered functioning of pathway regulators, have been associated with a broad range of cancers. See Clevers (2006) and Polakis (2007), both of which are incorporated herein by reference. Notably, more than 90% of colorectal cancer (CRC) tumors harbor a loss-of-function mutation in APC, a suppressor of the Wnt/b-catenin pathway. See Sjoblom et al., 2006, which is incorporated herein by reference. The ability of IWR compounds to stabilize Axin proteins and induce β-catenin destruction even in the absence of normal APC protein function suggests that they may block aberrant cell growth supported by hyperactivation of Wnt/β-catenin responses.

Indeed, IWR compounds are able to inhibit aberrant Wnt/β-catenin activity as a consequence of Apc loss in both mouse L cells (using Apc small interfering RNAs) and DLD-1 colorectal cancer cells (that harbor a loss-of-function mutation in APC). The ability of IWR-3 to mimic the cell growth effects of β-catenin siRNAs in several cancer cell lines that exhibit differences in growth dependency on Wnt/β-catenin pathway activity was also tested. Notably, IWR-3 mimicked the effects of β-catenin siRNAs on the growth of cells derived from cancers of the colon (DLD-1) and prostate (DU145) but not lung (H460), which suggests that IWR-3 successfully targeted the Wnt/β-catenin pathway in these cells. Indeed, overexpression of β-catenin can overcome the effects of IWR-3 on DLD-1 cell growth.

Aberrant transcriptional induction of Wnt/β-catenin target genes is typically observed in CRC cells that harbor loss-of-function mutations in the APC tumor suppressor. Consistent with the ability of IWR compounds to inhibit cancerous Wnt/β-catenin pathway responses, a decrease in the expression of Axin2 in DLD-1 cells after exposure to IWR-1 for 2 h was observed. Thus, Axin protein stability can be chemically controlled in order to suppress cancerous Wnt/β-catenin activity, as demonstrated by IWR compounds. See Chen et al. (2007), which is incorporated herein by reference.

The reliance of certain cancer types on Wnt pathways for sustaining growth likely represents an exploitation of normal tissue maintenance cues provided by Wnt proteins. For example, loss in activity of the tumor suppressor and β-catenin inhibitor Apc heightens Wnt signaling in a tissue that is well established to rely on Wnt signals for homeostatic renewal. Similarly, β-catenin mutations are frequently found in cancers of the liver, a tissue that relies on Wnt signaling for regeneration (The Cancer Genome Network, 2012). Given the frequency of mutations that give rise to a truncated Apc protein observed in colorectal cancer (~90%), the discussion and development of agents targeting Wnt signaling have largely focused on disabling pathway components that regulate the b-catenin transcriptional apparatus. The prevalence of APC mutations suggests that these lesions arise early in the course of disease progression (Fearon and Vogelson, 1990; Barker et al., 2009). At the same time, deregulated growth control in the gut epithelium is observed when APC is mutated in putative stem cells but not in differentiated cells thus providing compelling evidence that the cell of origin in gut cancers are likely stem cells (Cadigan and Waterman, 2012). Thus, cancer cells of origin must exhibit greater sensitivity than gut stem cells to loss of Wnt signaling in order for anti-Wnt agents to be viable disease management tools for this disease.

Whereas cancer genome sequencing has assigned Wnt signaling to various cancers based on the prevalence of mutations in Wnt pathway components, other cancers such as acute myeloid leukemia (AML) that have shown sensitivity to Wnt pathway modulation in animal models are devoid of such mutations (Lian et al., 2013). Given our understanding of Wnt signaling in cancer has been predominantly informed by studies in the gut, the existence of these other cancers either reflects our partial inventory of Wnt signaling components in other cell types or the limitations of genomic sequencing for revealing epigenetic changes in Wnt signaling such as altered RNA splicing or histone methylation. Either Porcn or b-catenin targeting agents or both could be useful in these disease contexts.

B. Regeneration

In addition to the applications of Wnt inhibitors as anti-cancer agents, these molecules may also be used for influencing cell differentiation programs in vitro. Indeed, two classes of Porcn and Tnks inhibitors have been widely adopted for use in the production of medically useful cell types from various precursor cells including induced pluripotent stem cells (iPSCs). When used in combination with other small molecules that influence cell fate outcome and in different cell culture conditions, nearly homogenous cell products can be achieved in some cases with these Wnt pathway antagonists (Narytnyk, et al., 2014; Ren, et al., 2011). For example, a chemically based strategy for cardiomyocyte production from iPSCs entails the use of two chemicals—one compound to activate Wnt signaling (GSK3β inhibitor) under embryoid body formation conditions and a Porcn inhibitor (IWP-2 and IWP-4) to inactivate Wnt signaling under monolayer growth conditions (Narytnyk, et al., 2014). In another example, a Tnks inhibitor could substitute for a Porcn inhibitor thus demonstrating the necessity of on-target effects of these Wnt inhibitors for robust cardiomyocyte induction (Nakano, et al., 2012).

The production of cardiomyocytes from iPSCs using only chemical reagents targeting the Wnt/β-catenin pathway has not only confirmed the well-recognized prowess of Wnt signaling in cell fate determination processes but also galvanized efforts to deploy Wnt pathway modulators in other tissue engineering agendas. Other successes include the production of dopaminergic neurons and retinal pigmented epithelial cells which could be used for in vitro screening for molecules with biological activity in these cell types or for the replacement of prematurely degenerated cells (Ren, et al., 2011; Distler, et al., 2013). The availability of these agents and the ease with which they can be applied to cultured cells has helped fuel the rapid growth in their use for tissue engineering. With the successful production of therapeutically relevant cell types, a challenge in the future will be to improve the integration of these cells into the host, a process that could be facilitated by stemming fibrotic responses in injured or aged tissues with the use of Wnt inhibitors with favorable pharmacokinetic properties (Henderson et al., 2010; Wang et al., 2014; Rouleau et al., 2010).

In some embodiments of the present disclosure, pluripotent stem cells and neural stem cells are exposed in vitro or in vivo to a compound described herein, resulting in the differentiation of the stem cells into neural precursor cells, neurons, or another type of cell such as a cardiac cell, a lung cell, a bone cell, or a cell from the eye. A neural precursor cell is a cell that can generate neuronal cells neurons or neuronal precursors) and glial cells (i.e., astrocytes, oligodendrocytes, or glial cell precursors), but cannot give rise to a pluripotent or neural stem cell.

The pervasive influence of the Wnt proteins in tissue homeostasis and tumorigenesis suggests areas such as regenerative medicine and anti-cancer therapy may benefit from therapies that target this pathway. Achieving transient repression of pathological Wnt response without incurring permanent damage to normal stem cell function is a key anticancer therapeutic goal. The inventors tested for the ability of zebrafish to resume regenerative processes following a chemically induced blockade of fin regrowth. Fish with resected caudal fins that were bred in water containing IWR-1 for 7 d were able to regenerate tissue to nearly normal levels after chemical removal, which suggests that transient inhibition of Wnt/β-catenin response does not permanently alter the ability of stem cells to self-renew.

In some aspects of the present disclosure, Wnt signals can promote cell proliferation and tissue expansion but also control fate determination or terminal differentiation of postmitotic cells. Sometimes, these disparate events, proliferation and terminal differentiation, can be activated by Wnt in different cell types within the same structure, such as the hair follicle or the intestinal crypt (Reya and Clevers, 2005). Numerous Tcf target genes have been identified in diverse biological systems. These studies tend to focus on target genes involved in cancer, as exemplified by the wide interest in the Wnt target genes cMyc and Cyclin D1.

Patterning of the embryo and cell specification events are activated by a few evolutionarily conserved pathways, one of which is the Wnt/β-catenin pathway. These signaling proteins are used repeatedly during development and in diverse regions. The canonical Wnt pathway has been shown to regulate cell fate decisions, cell proliferation, and cell migration in the embryo. Canonical Wnt signaling is important for neural development, neural crest specification and differentiation, and cardiac development. The signals are transduced in a cell-context dependent manner to result in rapid changes in gene transcription. Thus, in some aspects, the present disclosure provides compounds which can modulate the Wnt signaling pathway and particularly inhibit PARP enzymes such as Tankyrase. These compounds thus may be used to promote neural development and stem cell differentiation.

Reported evidence indicates that canonical Wnt signaling during narrow windows has differential effects during cardiac specification and heart development. Wnt signaling has been shown to be a major regulator of cardiogenesis (Cleutjens et al., 1999; Foley and Mercola, 2005; Salloway, 2003). Prior to gastrulation, Wnt/β-catenin signaling promotes cardiac differentiation whereas signaling during gastrulation inhibits heart formation (Cleutjens et al., 1999; Foley and Mercola, 2005; Salloway, 2003). Consistent with these studies, early treatment of mouse embryonic stem cells with Wnt3a stimulates mesoderm induction whereas late Wnt3a stimulation inhibits cardiac differentiation. Furthermore, the Wnt inhibitors Dickkopf-1 (Dkk-1) and secreted frizzled-related proteins (sFRPs) have been shown to induce cardiac differentiation of stem cells (Cleutjens et al., 1999; Salloway, 2003; Pandur et al., 2002)). Although these studies clearly demonstrate the importance of Wnt signaling in cardiac development, less is known about its role in adult cardiac repair. A recent study using Wnt (axin2-LacZ) reporter mice demonstrated that Wnt signaling is increased post-MI in cardiomyocytes of the border zone and remote area between 7-21 days whereas infiltrating $CD45^+$ inflammatory cells showed Wnt activation between 3-7 days (Oerlemans et al., 2009). Hence, endogenous activation of the Wnt pathway occurs in the heart in cardiomyocytes and other heart cells and is evident just prior to the initiation of the remodeling phase (day 10-26) of murine infarct repair. The inventors hypothesize that infarct-induced Wnt activation contributes to adverse cardiac remodeling, a process that may be averted by Wnt inhibition. Several recent studies support this hypothesis. Transgenic mice in which β-catenin was downregulated in an alpha-MHC-restricted manner (i.e., resulting in lower cardiac Wnt signaling) demonstrated favorable ischemic remodeling (Zelarayàn et al., 2008). Other groups reported functional deterioration after injury in mice expressing a stabilized β-catenin (i.e., activated Wnt signaling) in cardiomyocytes (Malekar et al., 2010; Baurand et al., 2007). Finally, it has been shown that mesenchymal stem cells overexpressing sFRP2, a Wnt inhibitor, reduced cardiomyocyte apoptosis (Mirotsou et al., 2007; Alfaro et al., 2008).

Thus, in one aspect of the present disclosure, there is provided a method inhibiting pathologic cardiac remodeling with the compounds disclosed herein. The cardiac remodeling may be associated with various aspects of cardiac disease, such as cardiac hypertrophy, dilated cardiomyopathy and heart failure. The treatment would comprise provision of the antibody in any of the aforementioed routes when formulated appropriately for that delivery mode. In particular, intravenous injection (systemic or into the cardiac vasculature) and intracardiac (muscular) injection are envisioned. Repeated treatments (2, 3, 4, 5, 6, 7, 8, 9, 10, 15, 20, 25, 50 or more) over extended periods (24 hrs, 48 hrs, 72 hrs, 1 wk, 2 wk, 3 wk, 4 wk, 1 month, 2 months, 3 months, 4 months, 5 months, 6 months, 1 year or longer) are contemplated.

III. WNT PROTEIN SIGNALLING INHIBITORS

The compounds provided by the present disclosure are shown, for example, above in the summary section and in the claims below. They may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Compounds of the disclosure may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present disclosure can have the S or the R configuration.

Chemical formulas used to represent compounds of the disclosure will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Compounds of the disclosure may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

Compounds of the present disclosure may also exist in prodrug form. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the disclosure contemplates prodrugs of compounds of the present disclosure as well as methods of delivering prodrugs. Prodrugs of the compounds employed in the disclosure may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in Handbook of Pharmaceutical Salts: Properties, and Use (2002), which is incorporated herein by reference.

It will appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present disclosure.

Persons of ordinary skill in the art will be familiar with methods of purifying compounds of the present disclosure. One of ordinary skill in the art will understand that compounds of the present disclosure can generally be purified at any step, including the purification of intermediates as well as purification of the final products. In preferred embodiments, purification is performed via silica gel column chromatography or HPLC.

IV. DEFINITIONS

As used herein, "Wnt protein signaling pathway" refers to the pathways by which binding of the Wnt protein to extracellular receptors is either translated into the nucleus and results in transcriptional activation of a variety of genes, or otherwise results in biochemical changes that influence cell behavior. The Wnt protein signaling pathways involve a variety of proteins including Frizzled, Disheveled, Axin, APC, GSK3β, β-catenin, LEF/TCF transcription factors, etc. Cells from many different species express homologs of the proteins involved in Wnt protein signalling pathways and accordingly have functionally equivalent Wnt protein signalling pathways. In some embodiments, the compounds may inhibit Wnt protein signaling by inhibiting porcupine.

As used herein, a "label" is any composition or moiety detectable by spectroscopic, photochemical, biochemical, immunochemical, or chemical means. Labels that may be employed in the present disclosure include radioactive labels (e.g., $^{32}P$, $^{125}I$, $^{14}C$, $^{3}H$, and $^{35}S$) and fluorescent dyes (e.g., Cy3). An example of a label that is not directly detected but is detected through the use of indirect methods is biotin.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

As used herein, the term "$IC_{50}$" refers to an inhibitory dose which is 50% of the maximum response obtained.

An "isomer" of a first compound is a separate compound in which each molecule contains the same constituent atoms as the first compound, but where the configuration of those atoms in three dimensions differs.

A "neural stem cell" is an undifferentiated cell from neural tissue that is capable of giving rise to more neural stem cells (i.e., exhibits self renewal) and to progeny cells that will terminally differentiate into neural cells. The neural stem cell can be an adult or embryonic neural stem cell.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present disclosure which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002), The term "pluripotent stem cell" refers to a cell capable of giving rise to cells of all three germinal layers, that is, endoderm, mesoderm and ectoderm. Although in theory pluripotent cell can differentiate into any cell of the body, the experimental determination of pluripotency is typically based on differentiation of a pluripotent cell into several cell types of each germinal layer. In some embodiments of the present disclosure, a pluripotent stem cell is an embryonic stem (ES) cell derived from the inner cell mass of a blastocyst. In other embodiments, the pluripotent stem cell is an induced pluripotent stem cell derived by reprogramming differentiated cells. In some embodiments, the pluripotent stem cell is an embryonic stem cell derived by somatic cell nuclear transfer.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Therapeutically effective amount" or "pharmaceutically effective amount" means that amount which, when administered to a subject or patient for treating a disease, is sufficient to effect such treatment for the disease.

The term "therapeutic benefit" or "therapeutically effective" as used throughout this application refers to anything that promotes or enhances the well-being of the subject with respect to the medical treatment of a condition. This includes, but is not limited to, a reduction in the onset, frequency, duration, or severity of the signs or symptoms of a disease. For example, a therapeutically effective amount of a compound of the present disclosure (that is, a Wnt protein signalling inhibitor) may be an amount sufficient to treat or prevent osteopetrosis.

The terms "inhibiting," or "reducing" or any variation of these terms, when used in the claims and/or the specification, includes any measurable decrease or complete inhibition to achieve a desired result. For example, there may be a decrease of 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity compared to normal. In a further example, following administering of a Wnt protein signalling inhibitor, a cancer patient may experience a reduction in tumor size.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The terms "contacted" and "exposed," when applied to a cell, are used herein to describe the process by which a compound of the present disclosure is administered or delivered to a target cell, or are placed in direct juxtaposition with the target cell. The terms "administered" and "delivered" are used interchangeably with "contacted" and "exposed."

As used herein, the term "water soluble" means that the compound dissolves in water at least to the extent of 0.010 mole/liter or is classified as soluble according to literature precedence.

Modifications or derivatives of the compounds, agents, and active ingredients disclosed throughout this specification are contemplated as being useful with the methods and compositions of the present disclosure. Derivatives may be prepared and the properties of such derivatives may be assayed for their desired properties by any method known to those of skill in the art, such as methods described herein.

Prodrugs and solvates of the compounds of the present disclosure are also contemplated herein. The term "prodrug," as used herein, is understood as being a compound which, upon administration to a subject, such as a mammal, undergoes chemical conversion by metabolic or chemical processes to yield a compound any of the formulas herein, or a salt and/or solvate thereof. Solvates of the compounds of the present disclosure are preferably hydrates.

As used herein, "protecting group" refers to a moiety attached to a functional group to prevent an otherwise unwanted reaction of that functional group. The term "functional group" generally refers to how persons of skill in the art classify chemically reactive groups. Examples of functional groups include hydroxyl, amine, sulfhydryl, amide, carboxyl, carbonyl, etc. Protecting groups are well-known to those of skill in the art. Non-limiting exemplary protecting groups fall into categories such as hydroxy protecting groups, amino protecting groups, sulfhydryl protecting groups and carbonyl protecting groups. Such protecting groups may be found in Greene and Wuts, 1999, incorporated herein by reference in its entirety. The Wnt protein signalling inhibitors described herein are also contemplated as protected by one or more protecting groups—that is, the inhibitors are contemplated in their "protected form."

In view of the above definitions, other chemical terms used throughout this application can be easily understood by those of skill in the art. Terms may be used alone or in any combination thereof.

The above definitions supersede any conflicting definition in any of the reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

V. PHARMACEUTICAL FORMULATIONS AND ROUTES FOR ADMINISTRATION

Pharmaceutical compositions of the present disclosure comprise an effective amount of one or more candidate substances (e.g., a Wnt protein signalling inhibitor) or additional agents dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one candidate substance or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, pp 1289-1329, 1990). Except insofar as any conventional carrier is incompatible with the active ingredient, its use in the therapeutic or pharmaceutical compositions is contemplated.

The candidate substance may comprise different types of carriers depending on whether it is to be administered in solid, liquid or aerosol form, and whether it needs to be sterile for such routes of administration as injection. Compounds of the present disclosure may be administered orally, intraadiposally, intraarterially, intraarticularly, intracranially, intradermally, intralesionally, intramuscularly, intranasally, intraocularally, intrapericardially, intraperitoneally, intrapleurally, intraprostaticaly, intrarectally, intrathecally, intratracheally, intratumorally, intraumbilically, intravaginally, intravenously, intravesicularlly, intravitreally, liposomally, locally, mucosally, orally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, via localized perfusion, bathing target cells directly, or by other method or any combination of the foregoing as would be known to one of ordinary skill in the art (see, for example, Remington's Pharmaceutical Sciences, 1990). In particular embodiments, the composition may be formulated for oral delivery. Pharmaceutical compositions comprising a compound of the present disclosure are also contemplated, and such compositions may be adapted for administration via any method known to those of skill in the art, such as the methods described above.

In particular embodiments, the composition is administered to a subject using a drug delivery device. Any drug delivery device is contemplated for use in delivering a pharmaceutically effective amount of a Wnt protein signalling inhibitor.

The actual dosage amount of a composition of the present disclosure administered to an animal patient can be determined by physical and physiological factors such as body weight, severity of condition, the type of disease being treated, previous or concurrent therapeutic interventions, idiopathy of the patient and on the route of administration. The practitioner responsible for administration will typically determine the concentration of active ingredient(s) in a composition and appropriate dose(s) for the individual subject.

The dose can be repeated as needed as determined by those of ordinary skill in the art. Thus, in some embodiments of the methods set forth herein, a single dose is contemplated. In other embodiments, two or more doses are contemplated. Where more than one dose is administered to a subject, the time interval between doses can be any time interval as determined by those of ordinary skill in the art. For example, the time interval between doses may be about 1 hour to about 2 hours, about 2 hours to about 6 hours, about 6 hours to about 10 hours, about 10 hours to about 24 hours, about 1 day to about 2 days, about 1 week to about 2 weeks, or longer, or any time interval derivable within any of these recited ranges.

In certain embodiments, it may be desirable to provide a continuous supply of a pharmaceutical composition to the patient. This could be accomplished by catheterization, followed by continuous administration of the therapeutic agent, for example. The administration could be intra-operative or post-operative.

In certain embodiments, pharmaceutical compositions may comprise, for example, at least about 0.1% of a Wnt protein signalling inhibitor. In other embodiments, the Wnt protein signalling inhibitor may comprise between about 2% to about 75% of the weight of the unit, or between about 25% to about 60%, for example, and any range derivable therein. In other non-limiting examples, a dose may also comprise from about 1 µg/kg/body weight, about 5 µg/kg/body weight, about 10 µg/kg/body weight, about 50 µg/kg/body weight, about 100 µg/kg/body weight, about 200 µg/kg/body weight, about 350 µg/kg/body weight, about 500 µg/kg/body weight, about 1 mg/kg/body weight, about 5 mg/kg/body weight, about 10 mg/kg/body weight, about 50 mg/kg/body weight, about 100 mg/kg/body weight, about 200 mg/kg/body weight, about 350 mg/kg/body weight, about 500 mg/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 µg/kg/body weight to about 500 mg/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal, or combinations thereof.

The Wnt protein signalling inhibitor may be formulated into a composition, such as a pharmaceutical composition, in a free base, neutral, or salt form. Pharmaceutically acceptable salts are described herein.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. It may be preferable to include isotonic agents, such as, for example, sugars, sodium chloride, or combinations thereof.

In other embodiments, one may use eye drops, nasal solutions or sprays, aerosols or inhalants in the present disclosure. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in certain embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the candidate substance is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. In certain embodiments, carriers for oral administration comprise inert diluents (e.g., glucose, lactose, or mannitol), assimilable edible carriers or combinations thereof. In other aspects of the disclosure, the oral composition may be prepared as a syrup or elixir. A syrup or elixir, and may comprise, for example, at least one active agent, a sweetening agent, a preservative, a flavoring agent, a dye, a preservative, or combinations thereof.

In certain embodiments an oral composition may comprise one or more binders, excipients, disintegration agents, lubricants, flavoring agents, or combinations thereof. In certain embodiments, a composition may comprise one or more of the following: a binder, such as, for example, gum tragacanth, acacia, cornstarch, gelatin or combinations thereof an excipient, such as, for example, dicalcium phosphate, mannitol, lactose, starch, magnesium stearate, sodium saccharine, cellulose, magnesium carbonate or combinations thereof a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar, or both.

Sterile injectable solutions may be prepared by incorporating a compound of the present disclosure in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, certain methods of preparation may include vacuum-drying or freeze-drying techniques which yield a powder of the active ingredient plus any additional desired ingredient from a previously sterile-filtered liquid medium thereof. The liquid medium should be suitably buffered if necessary and the liquid diluent (e.g., water) first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition should be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin, or combinations thereof.

VI. COMBINATION THERAPY

In order to enhance or increase the effectiveness of a Wnt protein signalling inhibitor of the present disclosure, the inhibitor may be combined with another therapy, such as another agent that combats and/or prevents cancer, myocardial infarction, osteopetrosis, a degenerative disease, or type II diabetes. For example, Wnt protein signalling inhibitors of the present disclosure may be provided in a combined amount with an effective amount another agent that is known to reduce tumor size.

It is contemplated that combination therapy of the present disclosure may be used in vitro or in vivo. These processes may involve administering the agents at the same time or within a period of time wherein separate administration of the substances produces a desired therapeutic benefit. This may be achieved by contacting the cell, tissue, or organism with a single composition or pharmacological formulation that includes two or more agents, or by contacting the cell with two or more distinct compositions or formulations, wherein one composition includes one agent and the other includes another.

The compounds of the present disclosure may precede, be co-current with and/or follow the other agents by intervals ranging from minutes to weeks. In embodiments where the agents are applied separately to a cell, tissue or organism, one would generally ensure that a significant period of time did not expire between the time of each delivery, such that the agents would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the candidate substance. In other aspects, one or more agents may be administered about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 1 week, about 2 weeks, about 3 weeks, about 4 weeks, about 5 weeks, about 6 weeks, about 7 weeks, or about 8 weeks or more, and any range derivable therein, prior to and/or after administering the candidate substance.

Various combination regimens of the agents may be employed. Non-limiting examples of such combinations are shown below, wherein a compound which inhibits the Wnt signaling pathway is "A" and a second agent, such as an anti-cancer agent, is "B":

| A/B/A | B/A/B | B/B/A | A/A/B | A/B/B | B/A/A |
|-------|-------|-------|-------|-------|-------|
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

A. Anti-Cancer Therapy

An anti-cancer agent may be used in combination therapy with Wnt protein signalling inhibitors of the present disclosure. As used herein, an "anti-cancer" agent is capable of negatively affecting cancer in a subject, for example, by killing one or more cancer cells, inducing apoptosis in one or more cancer cells, reducing the growth rate of one or more cancer cells, reducing the incidence or number of metastases, reducing tumor size, inhibiting tumor growth, reducing the blood supply to a tumor or one or more cancer cells, promoting an immune response against one or more cancer cells or a tumor, preventing or inhibiting the progression of a cancer, or increasing the lifespan of a subject with a cancer. Anti-cancer agents are well-known in the art and include, for example, chemotherapy agents (chemotherapy), radiotherapy agents (radiotherapy), a surgical procedure, immune therapy agents (immunotherapy), genetic therapy agents (gene therapy), reoviral therapy, hormonal therapy, other biological agents (biotherapy), and/or alternative therapies. In some embodiments, the present disclosure provides a combination therapy of a compound provided herein with 5-fluorouracil, leucovorin, and oxaliplatin or a compound provided herein with capecitabine and oxaliplatin. These combination therapies may be used in the treatment with colorectal cancer. Also, in some embodiments, the present disclosure provides a combination therapy comprising administering a compound provided herein and is co-administered with cytarabine and an anthracycline drug, such as daunorubicin and idarubicin. In some embodiments, these combination therapies may be administered for the treatment or prevention of acute myeloid leukemia (AML).

B. Osteopetrosis Therapy

Osteopetrosis, also known as marble bone disease and Albers-Schonberg disease, is an extremely rare inherited disorder whereby the bones harden, becoming denser, in contrast to the more prevalent osteomalacia, in which the bones soften. Bone marrow transplant therapy may be combined with administration of Wnt protein signalling inhibitors of the present disclosure to treat or prevent osteopetrosis. Other treatments targeting osteopetrosis that may be combined with Wnt protein signalling inhibitors described herein include those disclosed in the following documents, each of which is incorporated herein by reference: U.S. Pat. Nos. 7,241,732; 7,186,683; 6,943,151; 6,833,354; 6,699,873; 6,686,148; 5,806,529; 5,777,193; RE35,694; 5,641,747; and 4,843,063.

C. Degenerative Disease Therapy

As discussed herein, degenerative diseases may be treated using Wnt protein signalling inhibitors of the present disclosure. Accordingly, other treatments that target degenerative diseases may be combined with administration of the Wnt protein signalling inhibitors. Non-limiting examples of degenerative diseases include type II diabetes and age-related impairment of tissue repair.

1. Type II Diabetes Therapy

Type II diabetes is a chronic, progressive disease that has no clearly established cure. It is a metabolic disorder that is primarily characterized by insulin resistance, relative insulin deficiency and hyperglycemia. Treatment options that may be combined with Wnt protein signalling inhibitor administration include exercise, diet management to control the intake of glucose, and use of anti-diabetic drugs (e.g., metformin, phenformin, repaglinide, nateglinide, rosiglitazone, pioglitazone or miglitol).

2. Age-Related Impairment of Tissue Repair Therapy

A variety of tissues degenerate over time as one ages, such as skeletal muscle and organ tissues (e.g., heart, kidney, lung and liver). Wnt protein signalling inhibition has been implicated in, for example, muscle regeneration (Brack et al., 2007). Therapies pertaining to age-related impairment of tissue repair that may be combined with Wnt protein signalling inhibitor administration include, for example, gene therapy, such as described by Barton-Davis et al. (1998; incorporated herein by reference) and drugs described by Lynch (2004; incorporated herein by reference).

D. Myocardial Infarction

Myocardial infarctions (commonly known as a heart attack) is a condition in which blood flow to the heart muscle is interrupted or cut off and causes damage to the heart muscle. In particular, Wnt protein signaling inhibition has been shown to improve heart function after a myocardial infarction (Bastakoty and Young, 2016). The Porcn inhibitors described herein may be administered along with another therapy commonly administered after a myocardial infarction. Some non-limiting examples of additional therapies include changes in lifestyle or a medicine such as aspirin, a cholesterol lowering drug such as a statin, a beta blocker, an aldosterone antagonist, hormone replacement therapy, a nitrate compound, or an ACE inhibitor. The ACE inhibitor may be a sulfhydryl-containing agent such as a captopril or zofenopril, a dicarboxylate-containing agent such as enalapril, ramipril, quinapril, perindopril, lisinopril, benazepril, imidapril, trandolapril, cilazapril, a phosphonate-containing agent such as fosinopril, or a naturally occurring agent such as a casokinins, lactokinins, lactotripeptides, or arfalasin. Some examples of nitrates include isosorbide dinitrate, isosorbide mononitrate, nitroglycerin or any other pharmaceutically active compound which generates a nitrate in vivo. Additionally, beta blockers may be administered in conjunction with the Porcn inhibitors include propranolol, bucindolol, carteolol, carvedilol, labetalol, nadolol, oxprenolol, penbutolol, pindolol, sotalol, timolol, acebutolol, atenolol, betaxolol, bisoprolol, celiprolol, esmolol, metoprolol, or nebivolol. Furthermore, aldosterone antagonist may be spironolactone, eplerenone, canrenone, potassium canrenoate, or finerenone. Changes in lifestyle which may be used in conjunction with a Porcn inhibitor described herein include reducing weight to obtain a healthy weight or maintaining a healthy weight, an improved diet, increased physical activity, reduction of alcohol consumption, smoking cessation, or any combination thereof. It is also contemplated that the Porcn inhibitor may be administered during or before a myocardial infarction.

VII. EXAMPLES

The following examples are included to demonstrate certain preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Chemical synthesis is described below in Example 3. L-Wnt-STF cells (Chen, et al., 2009) were seeded into each well of a white opaque 96-well plate and compounds added immediately thereafter. Luciferase activities (Firefly luciferase for Wnt/b-catenin pathway activity and *Renilla* luciferase activity as an irrelevant cell signal) were measured using a previously reported protocol (Wang, et al., 2013). The $EC_{50}$ values of IWPs have been normalized to that of LGK974 control (Liu et al., 2013 and Cheng et al., 2016).

Example 2—Screening of Compounds for Suppression of Wnt Signaling

Additional IWPs to suppress Wnt signaling in L-Wnt-STF cells were synthesized and tested for their ability to suppress Wnt signaling as described above. The relevant data for some of the compounds are shown below in Table 1.

TABLE 1

Triazole Substituent Screening$^a$

10

| Entry | Ar$^1$ | Ar$^2$ | R | EC$_{50}$ |
|---|---|---|---|---|
| 1 | phenyl | H | H | >5 μM |
| 2 | 2-pyridyl | H | H | >5 μM |
| 3 | 3-pyridyl | H | H | 100 nM |
| 4 | 4-pyridyl | H | H | 9 nM |
| 5 | phenyl | phenyl | H | 400 nM |
| 6 | 2-F$_3$C-phenyl | phenyl | H | 500 nM |
| 7 | 4-MeO-phenyl | phenyl | H | 18 nM |
| 8 | 2-pyridyl | phenyl | H | 2500 nM |
| 9 | 3-pyridyl | phenyl | H | 5 nM |
| 10 | 4-pyridyl | phenyl | H | 0.08 nM |
| 11 | 4-pyridyl | phenyl | Me | 3 nM |
| 12 | 4-pyridyl | phenyl | Et | 12 nM |
| 13 | 4-pyridyl | 4-MeO-phenyl | H | 0.18 nM |
| 14 | 4-pyridyl | 4-EtO$_2$C-phenyl | H | 0.7 nM |
| 15 | 4-pyridyl | 4-NC-phenyl | H | 0.48 nM |
| 16 | 4-pyridyl | 4-F$_3$C-phenyl | H | 0.3 nM |
| 17 | 4-pyridyl | 4-F-phenyl | H | 0.2 nM |
| 18 | 4-pyridyl | 3-Me-phenyl | H | 0.4 nM |
| 19 | 4-pyridyl | 2-Me-phenyl | H | 40 nM |
| 20 | 4-pyridyl | 2-MeO-phenyl | H | 9 nM |
| 21 | 4-pyridyl | 1-naphthyl | H | 6.5 nM |

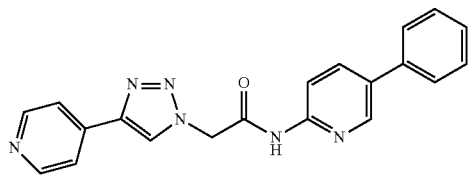

IWP-N3 (11)
EC$_{50}$ 9 nM

TABLE 1-continued

Triazole Substituent Screening[a]

[Structure: Ar¹, Ar² substituted triazole with R group, linked via CH(R)-C(=O)-NH to 5-phenylpyridin-2-yl]

| Entry | Ar¹ | Ar² | R | EC$_{50}$ |
|-------|-----|-----|---|-----------|

[Structure of IWP-O1 (12): 4-pyridyl and phenyl substituted triazole with CH₂-C(=O)-NH-(5-phenylpyridin-2-yl)]

IWP-O1 (12)
EC$_{50}$ 80 pM

[a] The EC$_{50}$ value of LGK974 is 0.2 nM in this assay.

Based upon these data, additional aryl groups were prepared off the amide group and the data are shown in Table 2.

TABLE 2

Aromatic Amide Group Screening

[Structure 13: 4-(pyridin-4-yl)-5-phenyl-1H-1,2,3-triazole linked via CH₂-C(=O)-NH-Ar]

| Entry | Ar | EC$_{50}$ |
|-------|----|-----------|
| 1 | 4-biphenyl | 0.43 nM |
| 2 | 3-biphenyl | 0.27 μM |
| 3 | 4-(piperidin-1-yl)phenyl | 8 nM |
| 4 | 4-(pyridin-2-yl)phenyl | 1.8 nM |
| 5 | 4-(pyridin-3-yl)phenyl | 0.2 μM |
| 6 | 4-(pyridin-4-yl)phenyl | 7 nM |
| 7 | 5-phenylpyridin-2-yl | 0.08 nM |
| 8 | 6-phenylpyridin-3-yl | 0.2 nM |

TABLE 2-continued

Aromatic Amide Group Screening

Structure 13: 4-(pyridin-4-yl)-5-phenyl-1H-1,2,3-triazole with N-CH₂-C(=O)-NH-Ar substituent on N1.

| Entry | Ar | EC₅₀ |
|---|---|---|
| 9 | 5-(piperidin-1-yl)pyridin-2-yl | >1 µM |
| 10 | 5-phenylpyrimidin-2-yl | 8 nM |
| 11 | 5-(pyridin-3-yl)pyridin-2-yl | >1 µM |
| 12 | 5-(pyrimidin-5-yl)pyridin-2-yl | 1.8 nM |
| 13 | 5-(thiophen-2-yl)pyridin-2-yl | 0.26 nM |
| 14 | 5-(thiophen-3-yl)pyridin-2-yl | 0.65 nM |
| 15 | 5-(furan-2-yl)pyridin-2-yl | 0.4 nM |
| 16 | 5-(furan-3-yl)pyridin-2-yl | 0.6 nM |
| 17 | 5-phenylthiazol-2-yl | 80 µM |

Finally, the aryl and heteroaryl groups on the triazole were modified and activity data for these compounds are shown in Table 3.

TABLE 3

Modification of Heteroaryl Group in the 4 Position Screening

Structure 14: 4-(6-R-pyridin-4-yl)-5-phenyl-1H-1,2,3-triazole with N-CH₂-C(=O)-NH-Ar substituent on N1.

| Entry | R | Ar | EC₅₀ |
|---|---|---|---|
| 1 | CH₃ | 5-phenylpyridin-2-yl | 0.14 nM |

TABLE 3-continued

Modification of Heteroaryl Group in the 4 Position Screening

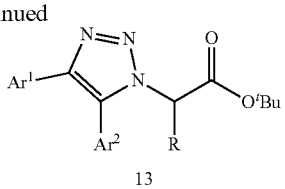

| Entry | R | Ar | EC$_{50}$ |
|---|---|---|---|
| 2 | CF$_3$ | 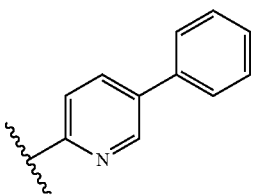 [SMILES: *c1ccc(-c2ccccc2)cn1] | 0.6 nM |
| 3 | CH$_3$ | 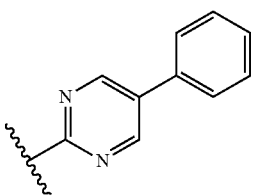 | 4 nM |
| 4 | CF$_3$ | 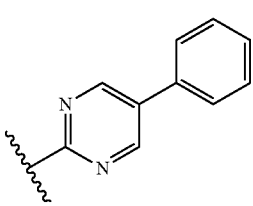 [SMILES: *c1ncc(-c2ccccc2)cn1] | 3 nM |

Figure 2:
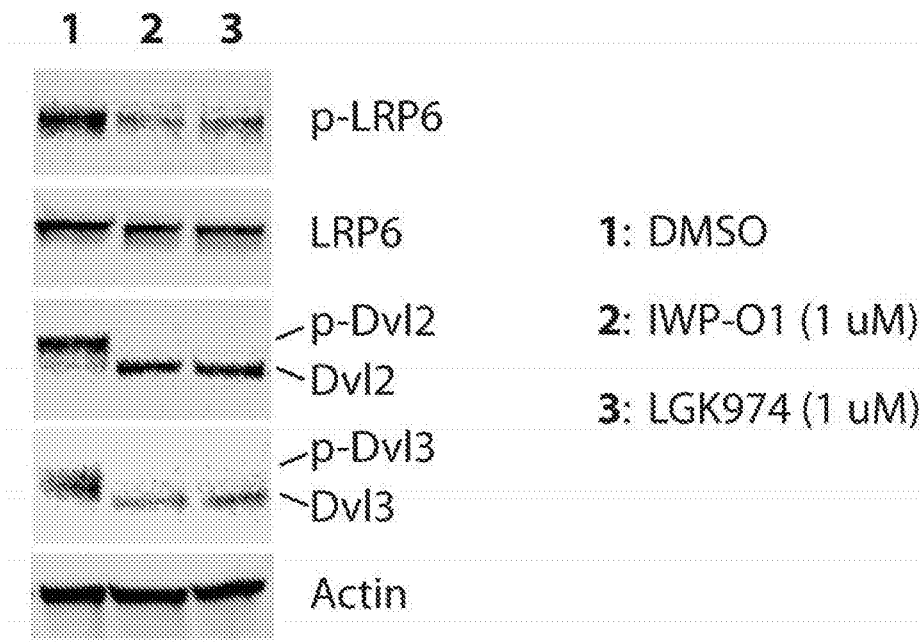
FIG. 2 shows the biochemical characterization of IWP-O1 (12). Hela cells, which exhibit high levels of cell autonomous Wnt signaling, were incubated for 24 h with DMSO, IWP-O1 (12), or LGK974. Cell lysates were then subjected to Western blot analysis for biochemical markers of Wnt signaling (LRP6 and Dvl2/3 phosphorylation).

The compound, IWP-O1 (12), has been biochemically evaluated to function by preventing the secretion of Wnt proteins. Dishevelled (Dvl) phosphorylation is associated with both canonical and non-canonical Wnt signaling pathways. IWP-O1 (12) effectively suppressed the phosphorylation of Dvl2/3 in Hela cells (FIG. 2). Consistently, the phosphorylation of low density lipoprotein receptor-related protein 6 (LPR6), a hallmark of the canonical β-catenin pathway activity, was also suppressed by the chemical treatment.

Example 3—Experimental Procedures and Compound Characterization

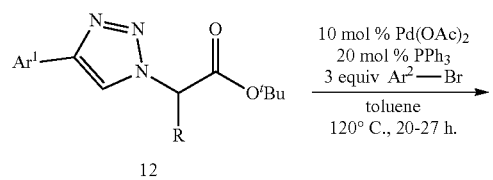

General Procedure for C—H Arylation

To a solution of triazole 12 (1.0 equiv) in toluene was added palladium(II) acetate (10 mol %), triphenylphosphine (20 mol %), potassium carbonate (2.0 equiv) and aryl bromide (3.0 equiv). After stirring for 24 h at 120° C., the mixture was quenched with saturated ammonium chloride and extracted with ethyl acetate. The combined organic layers were washed with brine and dried over sodium sulfate. The solvent was removed under vacuum, and the residue was purified by a flash column chromatography on silica gel to provide 13.

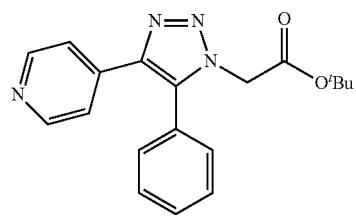 [SMILES: CC(C)(C)OC(=O)Cn1nnc(-c2ccncc2)c1-c1ccccc1]

tert-Butyl 2-(5-phenyl-4-(pyridin-4-yl)-1H-1,2,3-triazol-1-yl)acetate (11)

White solid; $^1$H NMR (400 MHz, CDCl$_3$): δ 8.52 (brs, 2H), 7.59-7.55 (m, 5H), 7.37-7.34 (m, 2H), 4.90 (s, 2H), 1.39 (s, 9H); ESI-MS m/z: 337.2 [M+H]$^+$.

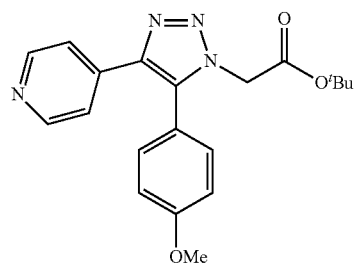 [SMILES: COc1ccc(-c2c(-c3ccncc3)nnn2CC(=O)OC(C)(C)C)cc1]

tert-Butyl 2-(5-(4-methoxyphenyl)-4-(pyridin-4-yl)-1H-1,2,3-triazol-1-yl)acetate White solid; $^1$H NMR (400 MHz, CDCl$_3$): δ 8.49 (brs, 2H), 7.50 (d, J=5.2 Hz, 2H), 7.25 (d, J=8.4 Hz, 2H), 7.03 (d, J=8.4 Hz, 2H), 4.87 (s, 2H), 3.88 (s, 3H), 1.40 (s, 9H); ESI-MS m/z: 367.2 [M+H]$^+$.

53

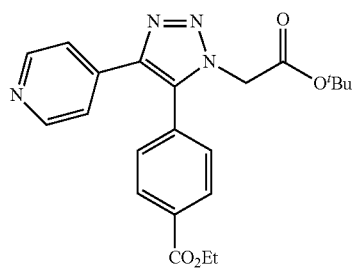 [SMILES: CCOC(=O)c1ccc(-c2c(-c3ccncc3)nnn2CC(=O)OC(C)(C)C)cc1]

tert-Butyl 2-(5-(4-ethoxycarbonylphenyl)-4-(pyridin-4-yl)-1H-1,2,3-triazol-1-yl)acetate White solid; $^1$H NMR (400 MHz, CDCl$_3$): δ 8.51 (brs, 2H), 8.20 (d, J=8.0 Hz, 2H), 7.49 (d, J=4.8 Hz, 2H), 7.45 (d, J=8.4 Hz, 2H), 4.90 (s, 2H), 4.44 (q, J=7.2 Hz, 2H), 1.44-1.39 (m, 12H); ESI-MS m/z: 409.2 [M+H]$^+$.

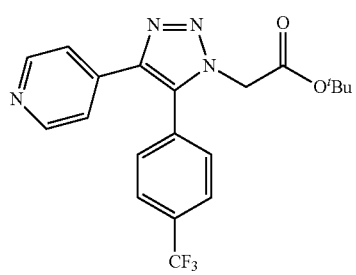 [SMILES: CC(C)(C)OC(=O)Cn1nnc(-c2ccncc2)c1-c1ccc(C(F)(F)F)cc1]

tert-Butyl 2-(4-(pyridin-4-yl)-5-(4-(trifluoromethyl)phenyl)-1H-1,2,3-triazol-1-yl)acetate White solid; $^1$H NMR (400 MHz, CDCl$_3$): δ 8.52 (brs, 2H), 7.79 (d, J=8.0 Hz, 2H), 7.51 (d, J=8.0 Hz, 2H), 7.41 (d, J=4.8 Hz, 2H), 4.90 (s, 2H), 1.38 (s, 9H); ESI-MS m/z: 405.2 [M+H]$^+$.

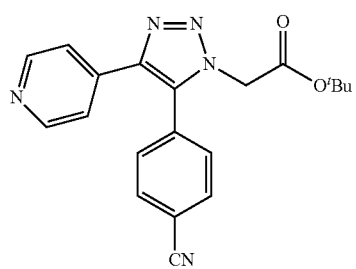 [SMILES: CC(C)(C)OC(=O)Cn1nnc(-c2ccncc2)c1-c1ccc(C#N)cc1]

tert-Butyl 2-(5-(4-cyanophenyl)-4-(pyridin-4-yl)-1H-1,2,3-triazol-1-yl)acetate

White solid; $^1$H NMR (400 MHz, CDCl$_3$): δ 8.55 (brs, 2H), 7.84 (d, J=8.0 Hz, 2H), 7.53 (d, J=8.4 Hz, 2H), 7.45 (d, J=4.4 Hz, 2H), 4.91 (s, 2H), 1.40 (s, 9H); ESI-MS m/z: 362.2 [M+H]$^+$.

54

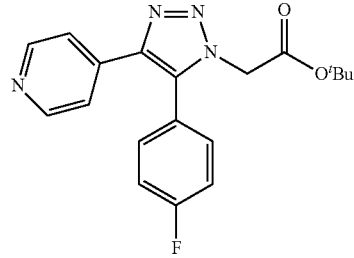 [SMILES: CC(C)(C)OC(=O)Cn1nnc(-c2ccncc2)c1-c1ccc(F)cc1]

tert-Butyl 2-(5-(4-fluorophenyl)-4-(pyridin-4-yl)-1H-1,2,3-triazol-1-yl)acetate

White solid; $^1$H NMR (400 MHz, CDCl$_3$): δ 8.51 (brs, 2H), 7.49 (d, J=4.8 Hz, 2H), 7.37-7.34 (m, 2H), 7.26-7.22 (m, 2H), 4.88 (s, 2H), 1.40 (s, 9H); ESI-MS m/z: 355.2 [M+H]$^+$.

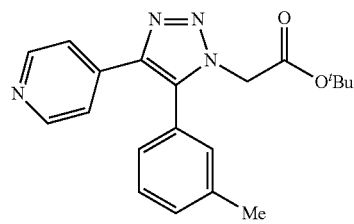 [SMILES: Cc1cccc(-c2c(-c3ccncc3)nnn2CC(=O)OC(C)(C)C)c1]

tert-Butyl 2-(5-(3-methylphenyl)-4-(pyridin-4-yl)-1H-1,2,3-triazol-1-yl)acetate

White solid; $^1$H NMR (400 MHz, CDCl$_3$): δ 8.51 (brs, 2H), 7.49 (brs, 2H), 7.42-7.34 (m, 2H), 7.14 (s, 1H), 7.12 (d, J=9.2 Hz, 1H), 4.86 (s, 2H), 2.38 (s, 3H), 1.39 (s, 9H); ESI-MS m/z: 351.2 [M+H]$^+$.

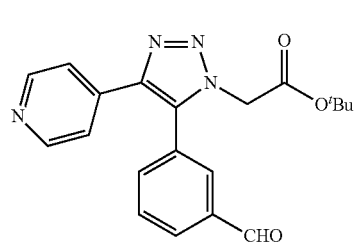 [SMILES: CC(C)(C)OC(=O)Cn1nnc(-c2ccncc2)c1-c1cccc(C=O)c1]

tert-Butyl 2-(5-(3-formylphenyl)-4-(pyridin-4-yl)-1H-1,2,3-triazol-1-yl)acetate

White solid; $^1$H NMR (400 MHz, CDCl$_3$): δ 10.06 (s, 1H), 8.10 (d, J=8.0 Hz, 1H), 7.92 (s, 1H), 7.75 (t, J=7.6 Hz, 1H), 7.68-7.62 (m, 2H), 7.54-7.52 (m, 2H), 7.47-7.45 (m, 1H), 4.91 (s, 2H), 1.39 (s, 9H); ESI-MS m/z: 365.2 [M+H]$^+$.

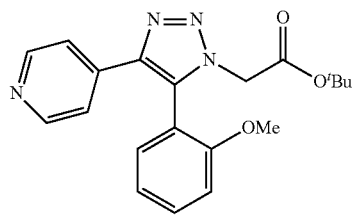 [SMILES: COc1ccccc1-c1c(-c2ccncc2)nnn1CC(=O)OC(C)(C)C]

tert-Butyl 2-(5-(2-methoxyphenyl)-4-(pyridin-4-yl)-1H-1,2,3-triazol-1-yl)acetate White solid; $^1$H NMR (400 MHz, CDCl$_3$): δ 8.50 (brs, 2H), 7.57-7.54 (m, 3H), 7.22 (dd, J=8.0, 1.6 Hz, 1H), 7.10-7.06 (m, 2H), 4.89 (dd, J=170.4, 14.8 Hz, 2H), 3.74 (s, 3H), 1.34 (s, 9H); ESI-MS m/z: 367.2 [M+H]$^+$.

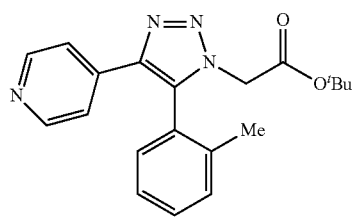 [SMILES: Cc1ccccc1-c1c(-c2ccncc2)nnn1CC(=O)OC(C)(C)C]

tert-Butyl 2-(5-(2-methylphenyl)-4-(pyridin-4-yl)-1H-1,2,3-triazol-1-yl)acetate

White solid; $^1$H NMR (400 MHz, CDCl$_3$): δ 8.50 (brs, 2H), 7.50-7.47 (m, 3H), 7.39-7.34 (m, 2H), 7.25 (d, J=6.8 Hz, 1H), 4.81 (dd, J=103.6, 17.2 Hz, 2H), 2.00 (s, 3H), 1.36 (s, 9H); ESI-MS m/z: 351.2 [M+H]$^+$.

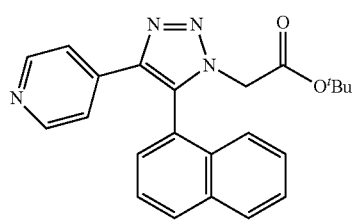 [SMILES: CC(C)(C)OC(=O)Cn1nnc(-c2ccncc2)c1-c1cccc2ccccc12]

tert-Butyl 2-(5-(naphthalen-1-yl)-4-(pyridin-4-yl)-1H-1,2,3-triazol-1-yl)acetate White solid; $^1$H NMR (400 MHz, CDCl$_3$): δ 8.40 (brs, 2H), 8.09 (d, J=8.0 Hz, 1H), 7.98 (d, J=8.4 Hz, 1H), 7.62-7.50 (m, 3H), 7.43-7.40 (m, 3H), 7.33 (d, J=8.4 Hz, 1H), 4.76 (dd, J=159.6, 17.2 Hz, 2H), 1.28 (s, 9H); ESI-MS m/z: 387.2 [M+H]$^+$.

tert-Butyl 2-(5-phenyl-4-(pyridin-3-yl)-1H-1,2,3-triazol-1-yl)acetate

White solid; $^1$H NMR (400 MHz, CDCl$_3$): δ 8.70 (d, J=2.2 Hz, 1H), 8.49 (dd, J=4.9, 1.7 Hz, 1H), 8.04 (dt, J=8.0, 1.9 Hz, 1H), 7.57-7.48 (m, 3H), 7.37-7.32 (m, 2H), 7.29 (dd, J=7.9, 5.0 Hz, 1H), 4.91 (s, 2H), 1.40 (s, 9H); ESI-MS m/z: 337.2 [M+H]$^+$.

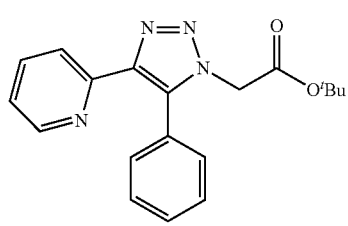 [SMILES: CC(C)(C)OC(=O)Cn1nnc(-c2ccccn2)c1-c1ccccc1]

tert-Butyl 2-(5-phenyl-4-(pyridin-2-yl)-1H-1,2,3-triazol-1-yl)acetate

White solid; $^1$H NMR (400 MHz, CDCl$_3$): δ 8.48 (d, J=4.6 Hz, 1H), 7.80 (d, J=7.9 Hz, 1H), 7.67 (t, J=7.8 Hz, 1H), 7.51-7.44 (m, 3H), 7.42-7.37 (m, 2H), 7.19-7.11 (m, 1H), 4.93 (s, 2H), 1.39 (s, 9H); ESI-MS m/z: 337.2 [M+H]$^+$.

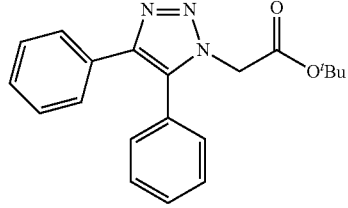 [SMILES: CC(C)(C)OC(=O)Cn1nnc(-c2ccccc2)c1-c1ccccc1]

tert-Butyl 2-(4,5-diphenyl-1H-1,2,3-triazol-1-yl)acetate

White solid; $^1$H NMR (400 MHz, CDCl$_3$): δ 7.57 (d, J=7.4 Hz, 2H), 7.54-7.44 (m, 3H), 7.35 (d, J=7.1 Hz, 2H), 7.29-7.27 (m, 2H), 4.90 (s, 2H), 1.40 (s, 9H); ESI-MS m/z: 336.2 [M+H]$^+$.

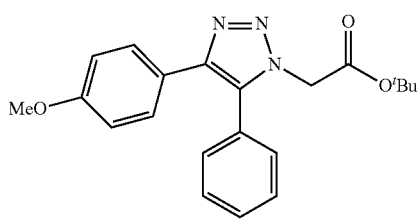 [SMILES: COc1ccc(-c2nnn(CC(=O)OC(C)(C)C)c2-c2ccccc2)cc1]

tert-Butyl 2-(4-(4-methoxyphenyl)-5-phenyl-1H-1,2,3-triazol-1-yl)acetate

Orange solid; ¹H NMR (400 MHz, CDCl₃): δ 7.55-7.44 (m, 5H), 7.34 (dd, J=7.4, 2.1 Hz, 2H), 6.81 (d, J=8.7 Hz, 2H), 4.89 (s, 2H), 3.78 (s, 3H), 1.39 (s, 9H); ESI-MS m/z: 366.2 [M+H]⁺.

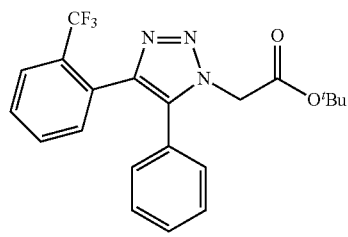 [SMILES: CC(C)(C)OC(=O)Cn1nnc(-c2ccccc2C(F)(F)F)c1-c1ccccc1]

tert-Butyl 2-(5-phenyl-4-(2-(trifluoromethyl)phenyl)-1H-1,2,3-triazol-1-yl)acetate Red solid; ¹H NMR (400 MHz, CDCl₃): δ 7.72 (dd, J=6.2, 3.0 Hz, 1H), 7.52-7.42 (m, 2H), 7.40-7.28 (m, 4H), 7.24-7.16 (m, 2H), 5.02 (s, 2H), 1.40 (s, 9H); ESI-MS m/z: 404.2 [M+H]⁺.

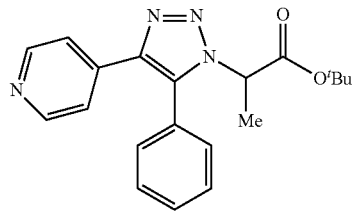 [SMILES: CC(C(=O)OC(C)(C)C)n1nnc(-c2ccncc2)c1-c1ccccc1]

tert-Butyl 2-(5-phenyl-4-(pyridin-4-yl)-1H-1,2,3-triazol-1-yl)propanoate

Yellow solid; ¹H NMR (400 MHz, CDCl₃): δ 8.52 (s, 2H), 7.82 (s, 2H), 7.72-7.61 (m, 2H), 7.58-7.47 (m, 1H), 7.36 (d, J=6.8 Hz, 1H), 4.83 (q, J=7.3 Hz, 1H), 1.91 (d, J=7.3 Hz, 3H), 1.41 (s, 9H); ESI-MS m/z: 351.2 [M+H]⁺.

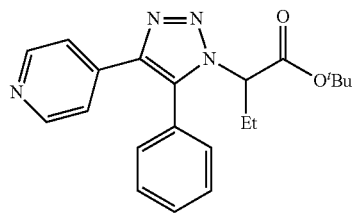 [SMILES: CCC(C(=O)OC(C)(C)C)n1nnc(-c2ccncc2)c1-c1ccccc1]

tert-Butyl 2-(5-phenyl-4-(pyridin-4-yl)-1H-1,2,3-triazol-1-yl)butanoate

White solid; ¹H NMR (400 MHz, CDCl₃): δ 8.52 (s, 2H), 7.89 (s, 2H), 7.77-7.61 (m, 3H), 7.40-7.31 (m, 2H), 4.58 (dd, J=10.7, 4.7 Hz, 1H), 2.51 (ddq, J=14.5, 10.6, 7.3 Hz, 1H), 2.34 (dqd, J=14.7, 7.4, 4.6 Hz, 1H), 1.42 (s, 9H), 0.91 (t, J=7.4 Hz, 3H); ESI-MS m/z: 365.2 [M+H]⁺.

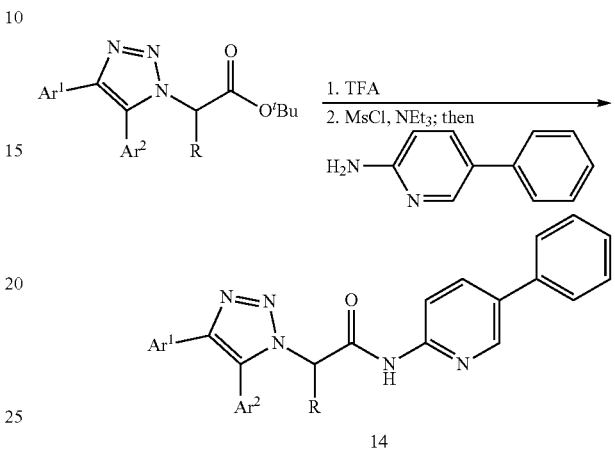

General Procedure for Amidation.

The solution of triazole 13 (1.0 equiv) in a mixture of trifluoroacetic acid and methylene chloride (1:2) was stirred at 35° C. for 3 h. The solvent was then removed by vacuum and the residue was dissolved in tetrahydrofuran. Triethylamine (1.1 equiv) and methanesulfonyl chloride (1.1 equiv) were subsequently added. After stirring at 23° C. for 3 h, a solution of 5-phenylpyridin-2-amine (1.2 equiv) and Hünig's base (5.0 equiv) in a mixture of tetrahydrofuran and benzene (1:4) was added. After stirring at 50° C. for 16 h, the mixture was quenched with saturated ammonium chloride and extracted with ethyl acetate. The combined organic layers were washed with brine and dried over sodium sulfate. The solvent was then removed under vacuum and the residue was purified by a flash column chromatography on silica gel to give 14.

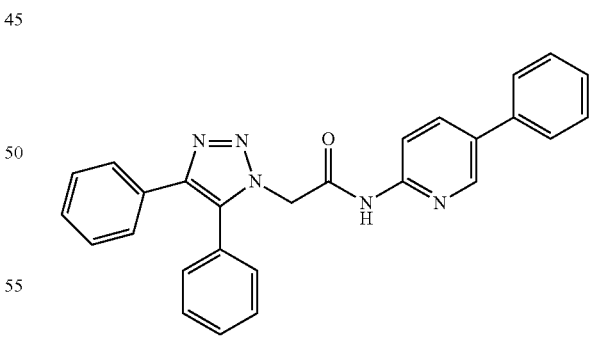

2-(4,5-Diphenyl-1H-1,2,3-triazol-1-yl)-N-(5-phenylpyridin-2-yl)acetamide

White solid; ¹H NMR (400 MHz, CDCl₃): δ 8.52 (d, J=2.3 Hz, 1H), 8.32 (d, J=8.8 Hz, 1H), 8.08 (dd, J=8.9, 2.4 Hz, 1H), 7.58-7.53 (m, 3H), 7.52 (s, 1H), 7.51-7.42 (m, 6H), 7.36 (dd, J=7.6, 2.0 Hz, 2H), 7.28-7.25 (m, 2H), 5.27 (s, 2H); ESI-MS m/z: 432.2 [M+H]⁺.

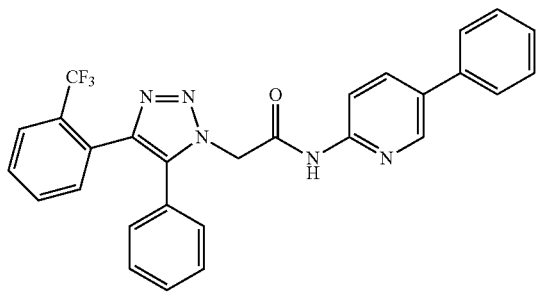 [SMILES: O=C(Cn1nnc(-c2ccccc2C(F)(F)F)c1-c1ccccc1)Nc1ccc(-c2ccccc2)cn1]

2-(5-Phenyl-4-(2-(trifluoromethyl)phenyl)-1H-1,2,3-triazol-1-yl)-N-(5-phenylpyridin-2-yl)acetamide White solid; $^1$H NMR (400 MHz, CDCl$_3$): δ 8.56 (d, J=2.3 Hz, 1H), 8.29 (d, J=8.7 Hz, 1H), 8.08-7.98 (m, 1H), 7.73 (dt, J=6.4, 3.8 Hz, 1H), 7.57-7.52 (m, 2H), 7.50-7.44 (m, 4H), 7.43-7.38 (m, 1H), 7.38-7.31 (m, 4H), 7.29-7.25 (m, 2H), 5.37 (s, 2H); ESI-MS m/z: 500.2 [M+H]$^+$.

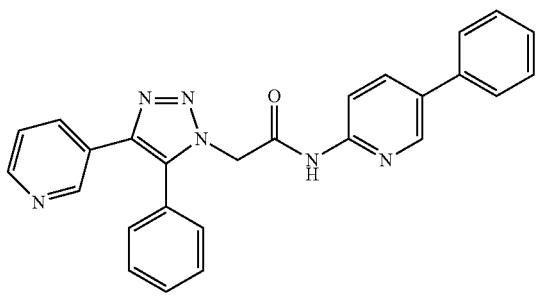

2-(5-Phenyl-4-(pyridin-3-yl)-1H-1,2,3-triazol-1-yl)-N-(5-phenylpyridin-2-yl)acetamide White solid; $^1$H NMR (400 MHz, CDCl$_3$): δ 8.83 (s, 1H), 8.58 (d, J=4.3 Hz, 1H), 8.18 (d, J=8.0 Hz, 2H), 7.93 (dd, J=8.4, 2.3 Hz, 1H), 7.52 (d, J=7.0 Hz, 5H), 7.48-7.37 (m, 6H), 5.25 (s, 2H); ESI-MS m/z: 433.2 [M+H]$^+$.

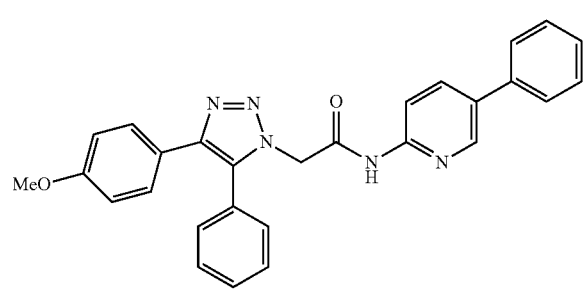 [SMILES: COc1ccc(-c2nnn(CC(=O)Nc3ccc(-c4ccccc4)cn3)c2-c2ccccc2)cc1]

2-(4-(4-Methoxyphenyl)-5-phenyl-1H-1,2,3-triazol-1-yl)-N-(5-phenylpyridin-2-yl)acetamide White solid; $^1$H NMR (400 MHz, CDCl$_3$): δ 8.83 (s, 1H), 8.58 (d, J=4.3 Hz, 1H), 8.18 (d, J=8.0 Hz, 2H), 7.93 (dd, J=8.4, 2.3 Hz, 1H), 7.52 (d, J=7.0 Hz, 5H), 7.48-7.37 (m, 6H), 5.25 (s, 2H); ESI-MS m/z: 462.2 [M+H]$^+$.

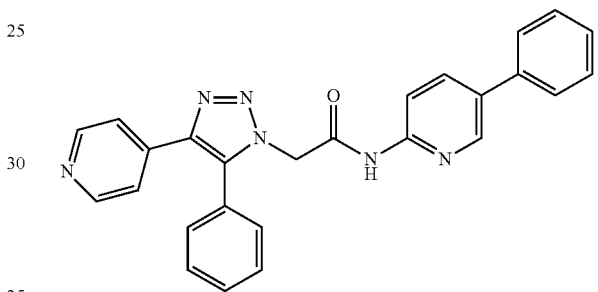

2-(5-Phenyl-4-(pyridin-4-yl)-1H-1,2,3-triazol-1-yl)-N-(5-phenylpyridin-2-yl)acetamide, IWP-O1 (16)

White solid; $^1$H NMR (400 MHz, CDCl$_3$): δ 8.57 (d, J=5.9 Hz, 2H), 8.47 (s, 1H), 8.19 (s, 1H), 8.01-7.80 (m, 3H), 7.68-7.32 (m, 11H), 5.29 (s, 2H); ESI-MS m/z: 433.2 [M+H]$^+$.

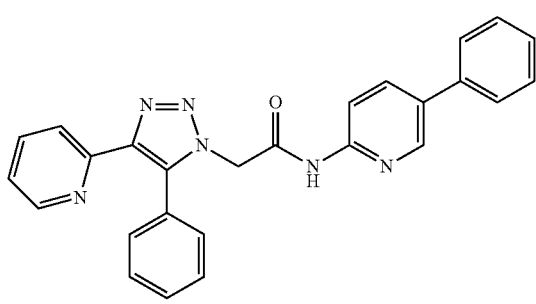 [SMILES: O=C(Cn1nnc(-c2ccccn2)c1-c1ccccc1)Nc1ccc(-c2ccccc2)cn1]

2-(5-Phenyl-4-(pyridin-2-yl)-1H-1,2,3-triazol-1-yl)-N-(5-phenylpyridin-2-yl)acetamide White solid; $^1$H NMR (400 MHz, CDCl$_3$): δ 8.67 (s, 1H), 8.63 (d, J=5.1 Hz, 1H), 8.17 (d, J=8.7 Hz, 1H), 8.02 (d, J=8.8 Hz, 1H), 7.77 (t, J=7.8 Hz, 1H), 7.68 (d, J=8.1 Hz, 1H), 7.58-7.51 (m, 2H), 7.52-7.37 (m, 8H), 7.26 (s, 1H), 5.30 (s, 2H); ESI-MS m/z: 433.2 [M+H]$^+$.

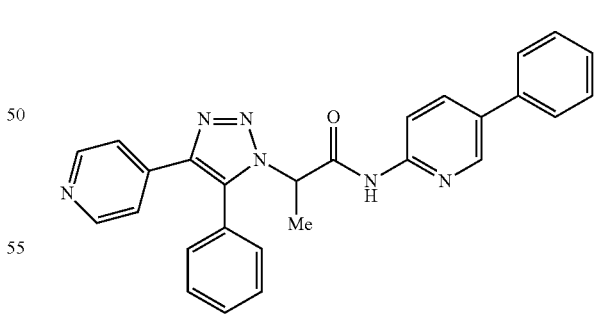

2-(5-Phenyl-4-(pyridin-4-yl)-1H-1,2,3-triazol-1-yl)-N-(5-phenylpyridin-2-yl)propanamide White solid; $^1$H NMR (400 MHz, CDCl$_3$): δ 8.54 (d, J=5.8 Hz, 2H), 8.50 (s, 1H), 8.28 (s, 1H), 7.98 (m, 3H), 7.71-7.62 (m, 3H), 7.60-7.36 (m, 8H), 5.14 (m, 1H), 2.10-2.06 (m, 3H); ESI-MS m/z: 447.2 [M+H]$^+$.

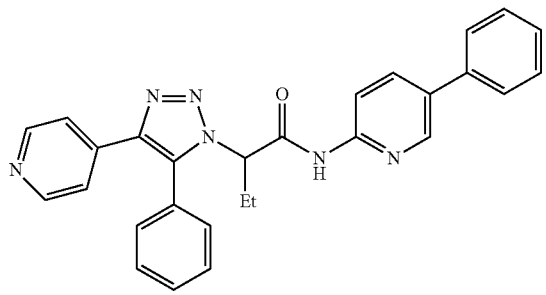 [SMILES: CCC(C(=O)Nc1ccc(-c2ccccc2)cn1)n1nnc(-c2ccncc2)c1-c1ccccc1]

2-(5-Phenyl-4-(pyridin-4-yl)-1H-1,2,3-triazol-1-yl)-N-(5-phenylpyridin-2-yl)butanamide White solid; ¹H NMR (400 MHz, CDCl₃): δ 8.55 (d, J=6.3 Hz, 2H), 8.33 (s, 1H), 8.03 (s, 3H), 7.68 (dt, J=15.0, 7.4 Hz, 3H), 7.60-7.35 (m, 7H), 4.90 (m, 1H), 2.59 (m, 2H), 1.33-1.19 (m, 3H); ESI-MS m/z: 461.2 [M+H]⁺.

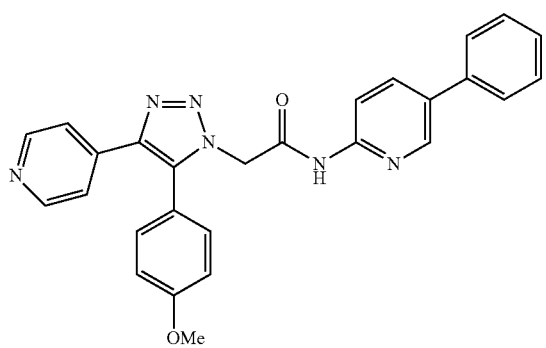 [SMILES: COc1ccc(-c2c(-c3ccncc3)nnn2CC(=O)Nc2ccc(-c3ccccc3)cn2)cc1]

2-(5-(4-Methoxyphenyl)-4-(pyridin-4-yl)-1H-1,2,3-triazol-1-yl)-N-(5-phenylpyridin-2-yl)acetamide White solid; ¹H NMR (400 MHz, CDCl₃): δ 8.57 (brs, 2H), 8.45 (s, 1H), 8.17 (brs, 1H), 7.91 (dd, J=8.8, 2.0 Hz, 1H), 7.76 (brs, 2H), 7.52-7.32 (m, 7H), 7.04 (d, J=8.0 Hz, 2H), 5.24 (s, 2H), 3.86 (s, 3H); ESI-MS m/z: 463.2 [M+H]+

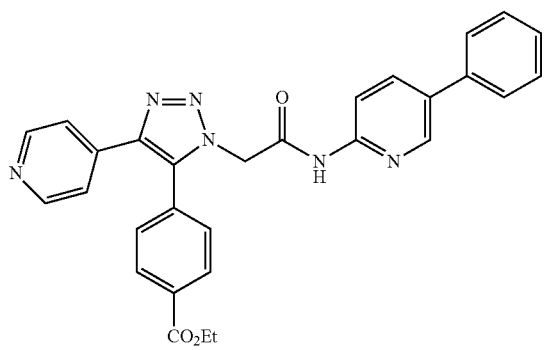 [SMILES: CCOC(=O)c1ccc(-c2c(-c3ccncc3)nnn2CC(=O)Nc2ccc(-c3ccccc3)cn2)cc1]

2-(5-(4-Ethoxycarbonylphenyl)-4-(pyridin-4-yl)-1H-1,2,3-triazol-1-yl)-N-(5-phenylpyridin-2-yl)acetamide White solid; ¹H NMR (400 MHz, CDCl₃): δ 8.56 (brs, 2H), 8.46 (s, 1H), 8.26 (d, J=7.6 Hz, 2H), 8.15 (brs, 1H), 7.91 (dd, J=8.8, 2.0 Hz, 1H), 7.58-7.38 (m, 10H), 5.22 (s, 2H), 4.21 (q, J=7.2 Hz, 2H), 1.40 (t, J=7.2 Hz, 3H); ESI-MS m/z: 505.2 [M+H]⁺.

2-(5-(4-Cyanophenyl)-4-(pyridin-4-yl)-1H-1,2,3-triazol-1-yl)-N-(5-phenylpyridin-2-yl)acetamide White solid; ¹H NMR (400 MHz, CD₃OD): δ 8.63 (brs, 2H), 8.54 (s, 1H), 8.00-7.95 (m, 5H), 7.86 (d, J=5.6 Hz, 2H), 7.74 (d, J=8.0 Hz, 2H), 7.60 (d, J=7.6 Hz, 2H), 7.45 (t, J=7.2 Hz, 2H), 7.37 (t, J=7.2 Hz, 1H), 5.37 (s, 2H); ESI-MS m/z: 458.2 [M+H]⁺.

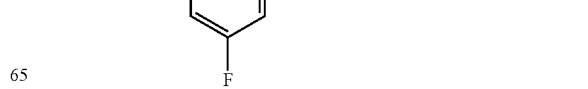

2-(4-(Pyridin-4-yl)-5-(4-Trifluorophenyl)-1H-1,2,3-triazol-1-yl)-N-(5-phenylpyridin-2-yl)acetamide White solid; ¹H NMR (400 MHz, CDCl₃): δ 8.85 (brs, 1H), 8.56 (brs, 2H), 8.51 (s, 1H), 8.17 (brs, 1H), 7.93 (dd, J=8.4, 2.0 Hz, 1H), 7.81 (d, J=8.4 Hz, 2H), 7.61-7.39 (m, 9H), 5.13 (s, 2H); ESI-MS m/z: 501.2 [M+H]⁺.

2-(5-(4-Fluorophenyl)-4-(pyridin-4-yl)-1H-1,2,3-triazol-1-yl)-N-(5-phenylpyridin-2-yl)acetamide White solid; $^1$H NMR (400 MHz, CDCl$_3$): δ 8.61 (s, 2H), 8.43 (s, 1H), 8.14 (brs, 1H), 7.92-7.86 (m, 3H), 7.50-7.38 (m, 8H), 7.24 (t, J=8.0 Hz, 2H), 5.38 (s, 2H). ESI-MS m/z: 451.2 [M+H]$^+$.

2-(5-(2-Methoxyphenyl)-4-(pyridin-4-yl)-1H-1,2,3-triazol-1-yl)-N-(5-phenylpyridin-2-yl)acetamide White solid; $^1$H NMR (400 MHz, CDCl$_3$): δ 8.57 (d, J=5.6 Hz, 2H), 8.49 (s, 1H), 8.19 (d, J=8.8 Hz, 1H), 7.96-7.92 (m, 3H), 7.62-7.37 (m, 6H), 7.28 (d, J=7.6 Hz, 2H), 7.15-7.10 (m, 2H), 5.20 (dd, J=37.6, 16.8 Hz, 2H), 3.72 (s, 3H); ESI-MS m/z: 463.2 [M+H]$^+$.

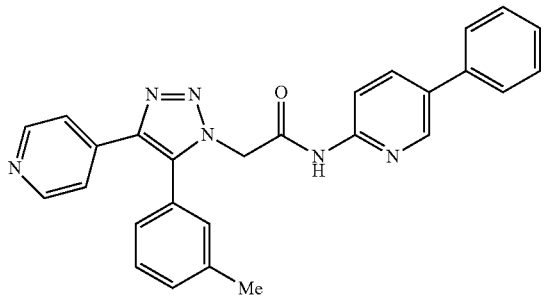 [SMILES: Cc1cccc(-c2c(-c3ccncc3)nnn2CC(=O)Nc2ccc(-c3ccccc3)cn2)c1]

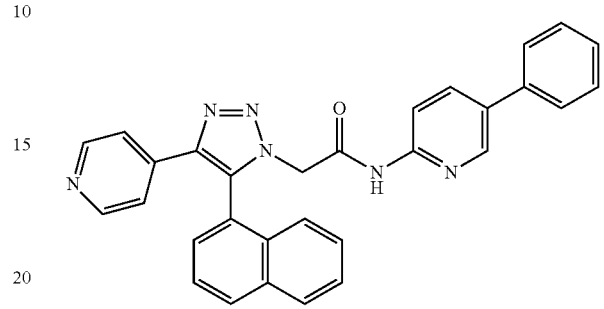

2-(5-(3-Methylphenyl)-4-(pyridin-4-yl)-1H-1,2,3-triazol-1-yl)-N-(5-phenylpyridin-2-yl)acetamide White solid; $^1$H NMR (400 MHz, CDCl$_3$): δ 9.05 (s, 1H), 8.45-8.37 (m, 4H), 8.04 (d, J=5.2 Hz, 2H), 7.59-7.44 (m, 8H), 7.08 (s, 1H), 7.04 (d, J=5.6 Hz, 1H), 5.68 (s, 2H), 2.42 (s, 3H); ESI-MS m/z: 447.2 [M+H]$^+$.

2-(5-(Naphthalen-1-yl)-4-(pyridin-4-yl)-1H-1,2,3-triazol-1-yl)-N-(5-phenylpyridin-2-yl)acetamide White solid; $^1$H NMR (400 MHz, CDCl$_3$): δ 8.44 (s, 2H), 8.42 (s, 1H), 8.09-8.07 (m, 2H), 7.96-7.91 (m, 2H), 7.79 (d, J=5.6 Hz, 2H), 7.61-7.39 (m, 10H), 7.23 (d, J=8.4 Hz, 1H), 5.27 (dd, J=186.4, 17.2 Hz, 2H); ESI-MS m/z: 483.2 [M+H]$^+$.

An alternative substitution pattern of the triazole has also been tested and prepared as described below.

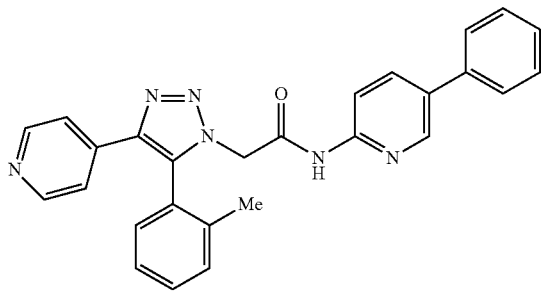 [SMILES: Cc1ccccc1-c1c(-c2ccncc2)nnn1CC(=O)Nc1ccc(-c2ccccc2)cn1]

2-(5-(2-Methylphenyl)-4-(pyridin-4-yl)-1H-1,2,3-triazol-1-yl)-N-(5-phenylpyridin-2-yl)acetamide White solid; $^1$H NMR (400 MHz, CDCl$_3$): δ 8.56 (brs, 2H), 8.43 (s, 1H), 8.12 (brs, 1H), 7.89 (dd, J=8.8, 2.0 Hz, 1H), 7.66 (brs, 2H), 7.51-7.30 (m, 10H), 5.16 (dd, J=85.2, 16.8 Hz, 1H), 2.03 (s, 3H). ESI-MS m/z: 447.2 [M+H]$^+$.

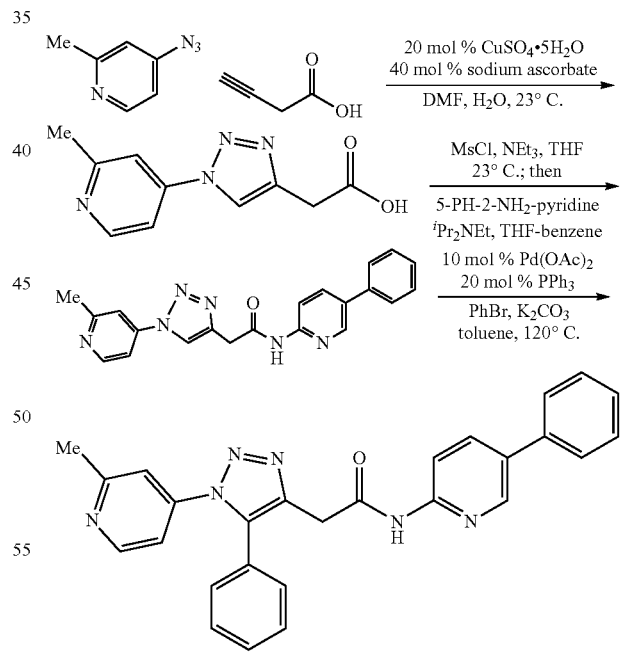

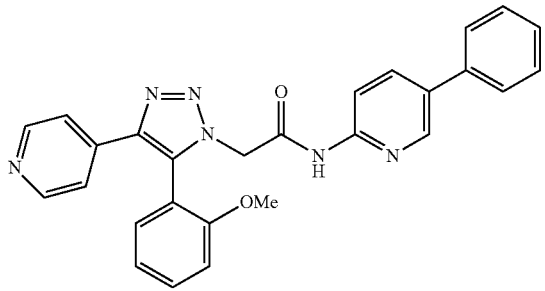 [SMILES: COc1ccccc1-c1c(-c2ccncc2)nnn1CC(=O)Nc1ccc(-c2ccccc2)cn1]

$^1$H NMR (400 MHz, CDCl$_3$) δ 13.01 (s, 1H), 8.78 (d, J=9.0 Hz, 1H), 8.73 (d, J=6.3 Hz, 1H), 8.40 (m, 1H), 7.77 (s, 1H), 7.54 (m, 8H), 7.38 (m, 3H), 4.09 (s, 2H), 2.79 (s, 3H); MS calcd for C$_{27}$H$_{23}$N$_6$O (M+H)$^+$ 447.2, found 447.2; EC$_{50}$ 0.1 nM.

All of the methods and apparatuses disclosed and claimed herein can be made and executed without undue experimentation in light of the present disclosure. While the compositions and methods of this disclosure have been described in terms of preferred embodiments, it will be apparent to those of skill in the art that variations may be applied to the methods and apparatuses and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VIII. REFERENCES

The following references, to the extent that they provide exemplary procedural or other details supplementary to those set forth herein, are specifically incorporated herein by reference.

U.S. Pat. No. 4,843,063
U.S. Pat. No. 5,641,747
U.S. Pat. No. 5,777,193
U.S. Pat. No. 5,806,529
U.S. Pat. No. 6,686,148
U.S. Pat. No. 6,699,873
U.S. Pat. No. 6,833,354
U.S. Pat. No. 6,943,151
U.S. Pat. No. 7,186,683
U.S. Pat. No. 7,241,732
U.S. Pat. RE35,694
PCT Patent Application Publication No. WO 2009/155001
Abrami et al., *Proc. Natl. Acad. Sci. USA*, 105(14):5384-53849, 2008.
Adams *Acta crystallographica. Section D, Biological crystallography*, 58:1948-1954, 2002.
Ailles and Weissman, *Curr. Opin. Biotech.*, 18:460-466, 2007.
Barker and Clevers, *Nat. Rev. Drug Discov.*, 5:997-1014, 2006.
Barker et al., *Nature*, 457(7229):608-611, 2009.
Barton-Davis et al., *Proc. Natl. Acad. Sci. USA*, 95:15603, 1998.
Bastakoty and Young, *FASEB J.*, 2016, Published Online Ahead of Print.
Bilic et al., *Science*, 316:1619-1622, 2007.
Borah et al., *Science*, 347:1006-1010, 2015.
Borror et al., *J. Org. Chem.*, 53:2047-2052.
Brack et al., *Science*, 317:807-810, 2007.
Cadigan and Waterman, *Cold Spring Harbor perspectives in biology*, 4(11), 2012.
Cerone et al., *Cancer Res.*, 71:3328-3340, 2011.
Chang et al., *Genes Dev*, 17:1328-1333, 2003.
Chang et al., *The Biochemical journal*, 391:177-184, 2005.
Chen et al., *Acta crystallographica. Section D, Biological crystallography*, 66:12-21, 2010.
Chen et al., *Nat. Chem. Biol.*, 5:100-107 2009.
Chen et al., *Oncogene*, 27:3483-3488, 2008.
Chen et al., *Nat Chem Biol*, 5:100-107, 2009.
Cheng et al., *ACS Med. Chem. Lett., ASAP*, DOI: 10.1021/acsmedchemlett.1026b00038, 2016
Clevers & Nusse, *Cell*, 149: 1192-1205, 2012.
Clevers, *Cell*, 127:469-480, 2006.
Cole et al., *Genes Dev.*, 22:746-755, 2008.
Cook, *Mol Cell Biol.*, 22:332-342, 2002.
Diala et al., *EMBO reports*, 14:356-363, 2013.
Distler et al., *Annals of the rheumatic diseases*, 72(9):1575-1580, 2013.
Dodge et al., *J Biol. Chem.*, 287, 23246-23254, 2012.
Dong et al., *Bioorg. Med. Chem.*, 23:6855-6868, 2015.
Dorogov et al., *Synthesis*, 18:2999-3004.
Duraiswamy et al., *J. Med. Chem.*, 58, 5889-5899, 2015.
Emsley and Cowtan, *Acta crystallographica. Section D, Biological crystallography*, 60:2126-2132, 2004.
Fearon and Vogelstein, *Cell*, 61(5):759-767, 1990.
Fevr et al., *Mol. Cell Biol.*, 27:7551-7559, 2007.
Ghaedi et al., *J Clin Invest.*, 123:4950-4962, 2013.
Gonzalez et al., *Angew Chem Int Ed Engl.*, 50:11181-11185, 2011.
Gonzalez-Sancho, et al., *Mol Cell Biol.*, 24:4757-4768, 2004.
Greene and Wuts, In: *Protective Groups in Organic Synthesis*, $2^{nd}$ Ed.; Wiley, N Y, 1999.
Gunaydin et al., *PLoS ONE*, 7:e33740, 2012.
Haikarainen, et al., *PLoS ONE*, 8: e65404, 2013.
Handbook of Pharmaceutical Salts: Properties, Selection and Use, 2002.
Henderson et al., *Proc Natl Acad Sci USA*, 107(32):14309-14314, 2010.
Hoffmeyer et al., *Science*, 336:1549-1554, 2012.
Hofmann, *Trends Biochem. Sci.*, 25:111-112, 2000.
Horn et al., *Science*, 339:959-961, 2013.
Huang and He, *Curr. Opin. Cell Biol.*, 20(2):119-125, 2008.
Huang and He, *Current opinion in cell biology*, 2008.
Huang et al., *Nature biotechnology*, 32:84-91, 2014.
Huang et al., *Nature*, 461:614-620, 2009.
Jacob et al., *Science signaling*, 4:ra4, 2011.
Kinzler and Vogelstein, *Cell*, 87:159-170, 1996.
Korinek et al., *Nat. Genet.*, 19:379-383, 1998.
Kurayoshi et al., *Biochem. J.*, 402:515, 2007.
Lee et al., *PLoS Biol.*, 1:E10, 2003; erratum in *PLoS Biol.*, 2:E89 (2004).
Lehtio et al., *Journal of molecular biology*, 379:136-145, 2008.
Lian et al., *Nature protocols*, 8:162-175, 2013.
Lian, et al., *Nature protocols*, 8(1):162-175, 2013.
Liu et al., *Proc. Natl. Acad. Sci.*, 110: 20224-20229, 2013
Liu et al., *Science*, 317:803-806, 2007.
Lu et al., *Bioorg. Med. Chem. Lett.*, Apr. 18, 2009 (Epub ahead of print).
Ludlow, et al., *Nucleic Acids Res.*, 2014.
Lum & Chen, *Curr. Med. Chem.*, 22:4091-4103, 2015.
Lum and Clevers *Science*, 337:922-923, 2012.
Lum et al., *The Journal of biological chemistry*, 273:26236-26247, 1998.
Lynch, *Exp. Opin. Emerging Drugs*, 9:345, 2004.
Madan et al., *Oncogene*, 35:2197-220720160.
March's Advanced Organic Chemistry: Reactions, Mechanisms, and Structure (March's Advanced Organic Chemistry), Smith and March (Eds.), 2001.
McCoy et al., *Journal of applied crystallography*, 40:658-674, 2007.
Muncan et al., *EMBO Rpts.*, 8:966-973, 2007.
Munoz et al., *Mol. Cell Biol.*, 29:1608-1625, 2009.
Nakano et al., *Cell stem cell* 10:771-785, 2012.
Nakano et al., *Cell stem cell*, 10(6):771-785, 2012.
Narwal et al., *Journal of medicinal chemistry*, 55:1360-1367, 2012.
Narytnyk, et al., *Stem cell reviews*, 10(2):316-326, 2014.
Ohki and Ishikawa, *Nucleic Acids Res.*, 32:1627-1637, 2004.
Orsulic et al., *J. Cell Sci.*, 112 (Pt 8):1237-1245, 1999.

Palm and de Lange, *Annual review of genetics*, 42:301-334, 2008.
Polakis, *Curr. Opin. Genet. Develop.*, 17:45-51, 2007.
Poulsen et al., *J. Chem. Inf. Model.*, 55:1435-1448, 2015.
Ramsay et al., *Nat Genet.*, 45:526-530, 2013.
Remington's Pharmaceutical Sciences, 18th Ed. Mack Printing Company, 1289-1329, 1990.
Ren et al., *J Mol Cell Cardiol.* 51:280-287, 2011.
Ren et al., *J Mol Cell Cardiol*, 51(3):280-287, 2011.
Reya and Clevers, *Nature*, 434:843-850, 2005.
Robles-Espinoza et al., *Nat Genet.*, 46:478-481, 2014.
Scholer-Dahirel, et al., *Proc. Natl. Acad. Sci., USA.*, 2011.
Schwarz-Romond et al., *J. Cell Sci.*, 120:2402-2412, 2007.
Seimiya et al., *Cancer Cell*, 7:25-37, 2005.
Shay and Wright *Seminars in cancer biology*, 21:349-353, 2011.
Shepard et al., *Proc. Natl. Acad. Sci. USA*, 102:13194-13199, 2005.
Shi et al., *Nat. Genet.*, 46:482-486, 2014.
Sjoblom et al., *Science*, 314:268-274, 2006.
Smith et al., *Science*, 282:1484-1487, 1998.
Stoick-Cooper et al., *Development*, 134:479-489, 2007.
Takada et al., *Dev. Cell*, 11:791-801, 2006.
Takai et al. *Curr Biol.*, 13:1549-1556, 2003.
The Cancer Genome Atlas Network, *Nature*, 487(7407):330-337, 2012.
Thompson et al., *Clin Cancer Res.*, 19:6578-6584, 2013.
Tian et al., *Oncology reports*, 32:1999-2006, 2014.
Van der Flier et al., *Gastroenterology*, 132:628-632, 2007.
Veeman et al., *Developmental Cell*, 5:367, 2003.
Wahlberg et al., *Nature biotechnology*, 30:283-288, 2012.
Walsh et al., *Nat. Genet.*, 46:731-735, 2014.
Wang et al., *ACS chemical biology*, 6:192-197, 2011.
Wang et al., *J. Med. Chem.*, 562700-2704, 2013.
Wang et al., *American journal of physiology. Cell physiology*, 307(3):C234-244, 2014.
Wang et al., *Science*, 327(5973):1650-1653.
Yang et al., *Hepatology*, 60(3):964-976, 2014.
Zhang et al., *The Journal of biological chemistry*, 287:32494-32511, 2012.
Zimmerman et al., *Cold Spring Harb. Perspect. Biol.*, 4:a008086, 2012.

What is claimed is:

1. A compound of the formula:

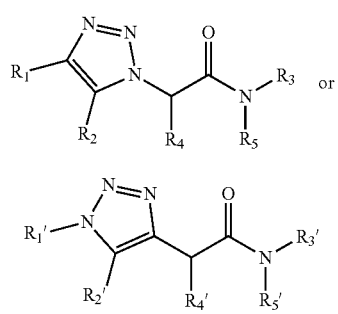

wherein:
$R_1$ and $R_1'$ are each independently aryl$_{(C \leq 18)}$, heteroaryl$_{(C \leq 18)}$, or a substituted version of either group;
$R_2$ is aryl$_{(C \leq 18)}$, substituted aryl$_{(C \leq 18)}$, heteroaryl$_{(C \leq 18)}$, or substituted heteroaryl$_{(C \leq 18)}$;
$R_2'$ is hydrogen, aryl$_{(C \leq 18)}$, substituted aryl$_{(C \leq 18)}$, heteroaryl$_{(C \leq 18)}$, or substituted heteroaryl$_{(C \leq 18)}$;
$R_3$ and $R_3'$ are each independently —X—Y;
wherein:
X is arenediyl$_{(C \leq 18)}$, substituted arenediyl$_{(C \leq 18)}$, heteroarenediyl$_{(C \leq 18)}$, or substituted heteroarenediyl$_{(C \leq 18)}$;
Y is aryl$_{(C \leq 12)}$, heteroaryl$_{(C \leq 12)}$, heterocycloalkyl$_{(C \leq 12)}$, or a substituted version of these three groups;
$R_4$ and $R_4'$ are each independently hydrogen, alkyl$_{(C \leq 12)}$, or substituted alkyl$_{(C \leq 12)}$; and
$R_5$ and $R_5'$ are each independently hydrogen, alkyl$_{(C \leq 12)}$, or substituted alkyl$_{(C \leq 12)}$;
or a pharmaceutically acceptable salt thereof.

2. The compound of claim 1, wherein the compound is a compound of formula Ia.

3. The compound of claim 1, wherein the compound is a compound of formula Ib.

4. The compound of claim 1 further defined as a compound of formula Ib, wherein:
$R_4'$ is hydrogen, alkyl$_{(C \leq 8)}$, or substituted alkyl$_{(C \leq 8)}$; and
$R_5'$ is hydrogen, alkyl$_{(C \leq 8)}$, or substituted alkyl$_{(C \leq 8)}$;
or a pharmaceutically acceptable salt thereof.

5. The compound according to claim 1, wherein $R_1$ or $R_1'$ is heteroaryl$_{(C \leq 12)}$ or substituted heteroaryl$_{(C \leq 12)}$.

6. The compound according to claim 1, wherein $R_1$ or $R_1'$ is aryl$_{(C \leq 12)}$ or substituted aryl$_{(C \leq 12)}$.

7. The compound according to claim 1, wherein $R_2$ or $R_2'$ is aryl$_{(C \leq 12)}$ or substituted aryl$_{(C \leq 12)}$.

8. The compound according to claim 1, wherein X is arenediyl$_{(C \leq 18)}$ or substituted arenediyl$_{(C \leq 18)}$.

9. The compound according to claim 1, wherein X is heteroarenediyl$_{(C \leq 18)}$ or substituted heteroarenediyl$_{(C \leq 18)}$.

10. The compound according to claim 1, wherein Y is aryl$_{(C \leq 12)}$ or substituted aryl$_{(C \leq 12)}$.

11. The compound according to claim 1, wherein Y is heteroaryl$_{(C \leq 12)}$ or substituted heteroaryl$_{(C \leq 12)}$.

12. The compound according to claim 1, wherein Y is heterocycloalkyl$_{(C \leq 12)}$ or substituted heterocycloalkyl$_{(C \leq 12)}$.

13. The compound according to claim 1, wherein the compound is further defined as:

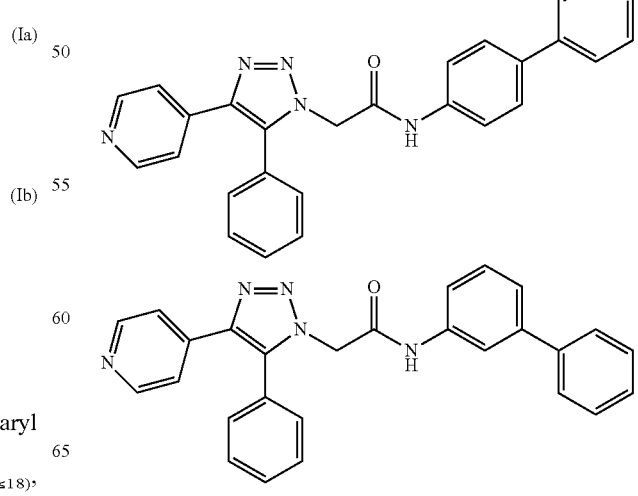

69
-continued
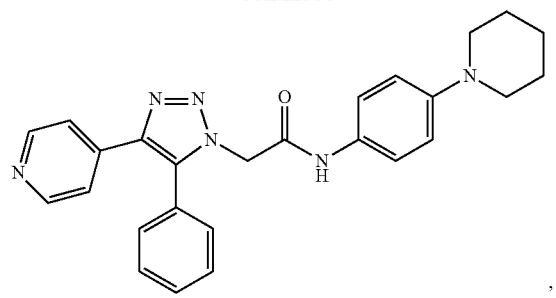
,
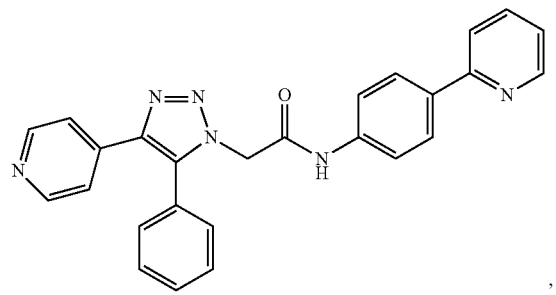
,
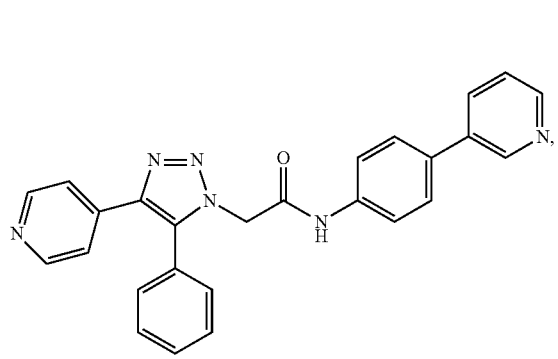
,
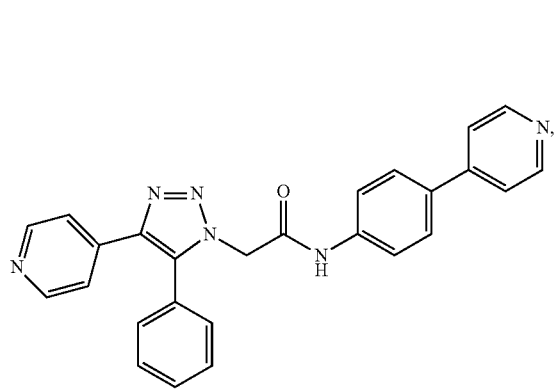
,
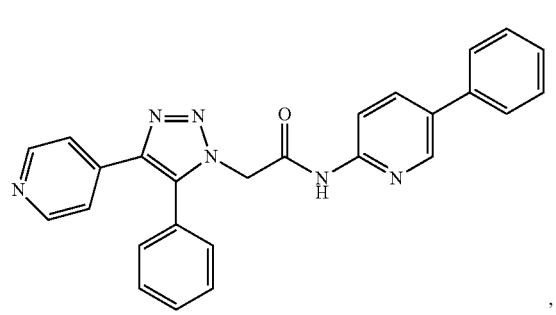
,
70
-continued
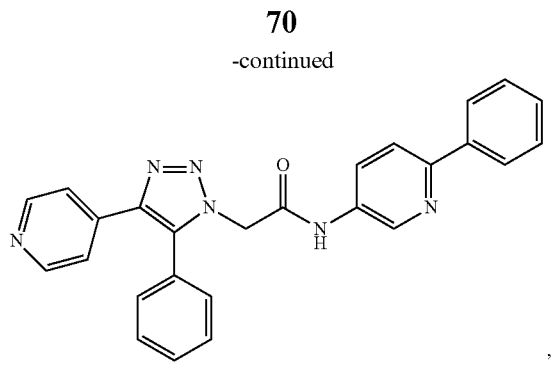
,
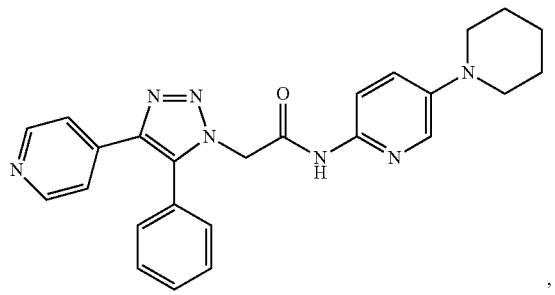
,
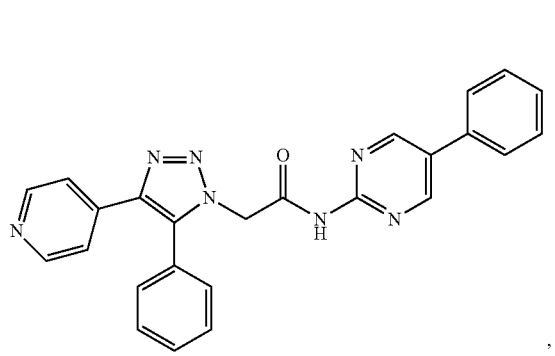
,
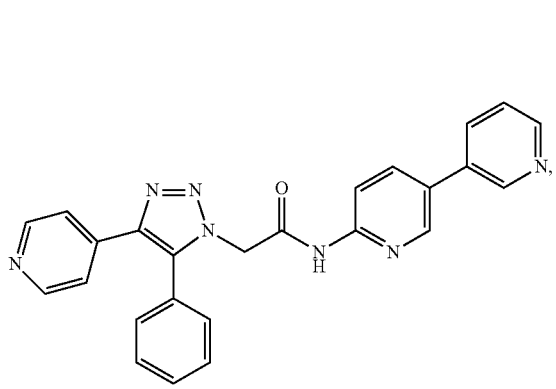
,
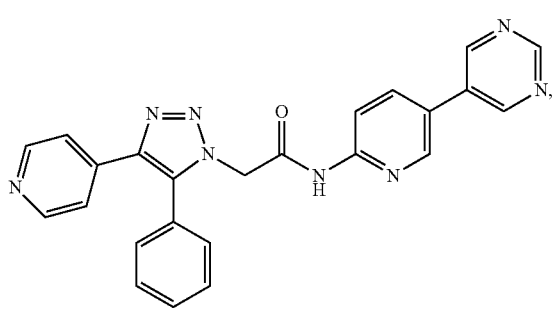
, 71
-continued
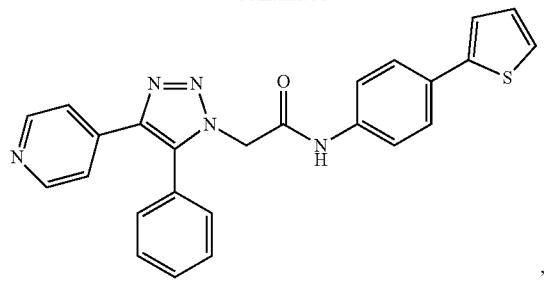
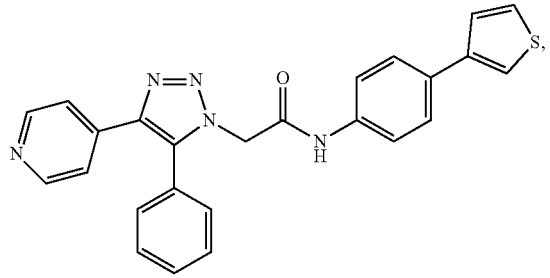
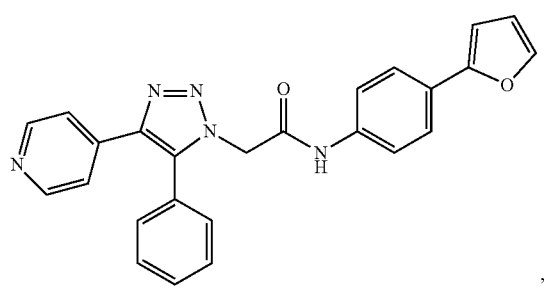
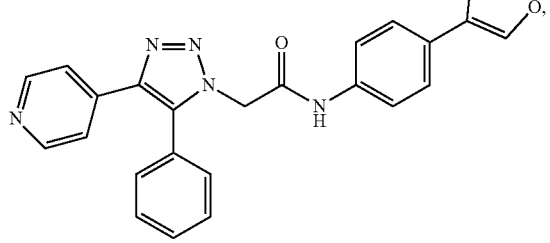
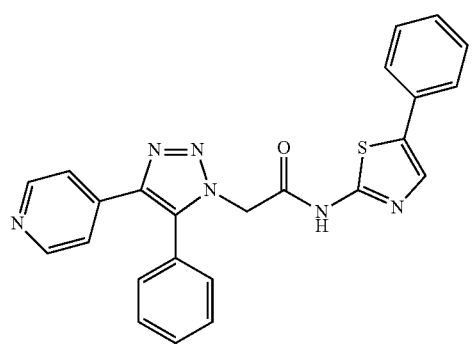
72
-continued
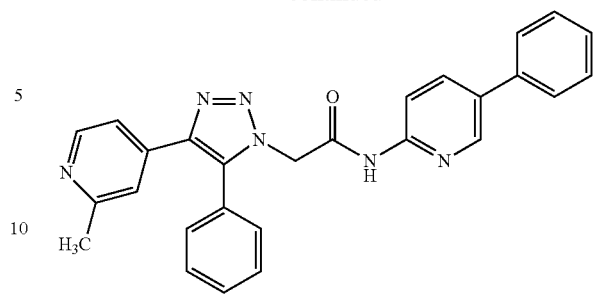
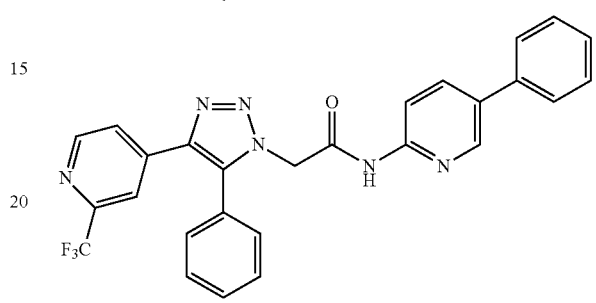
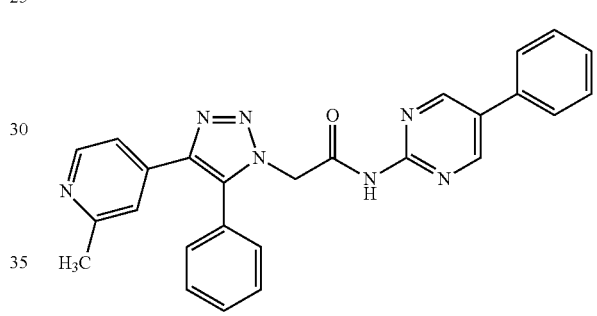
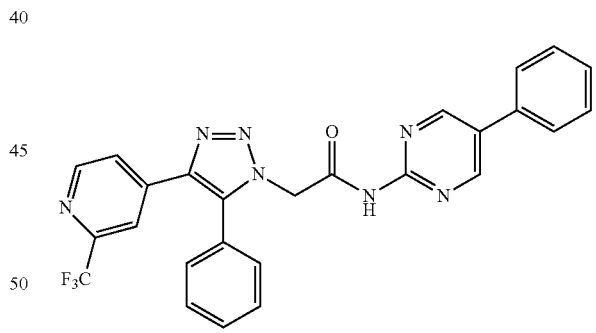
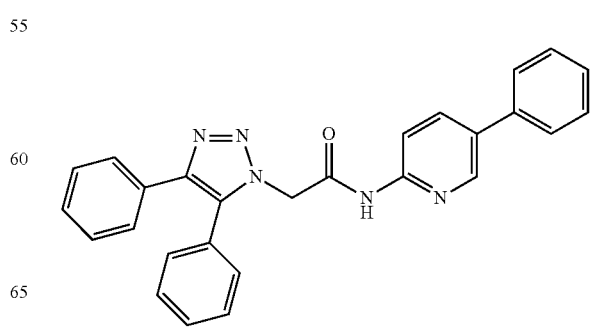

73
-continued
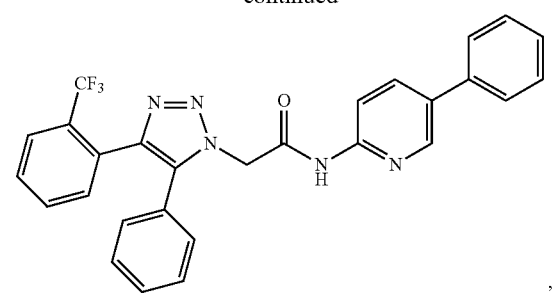
,
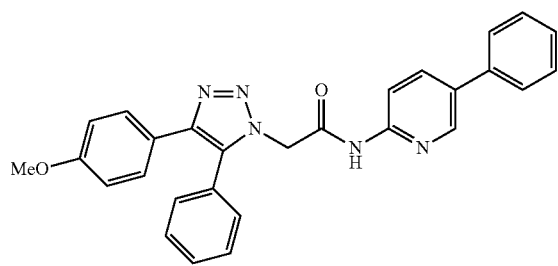
,
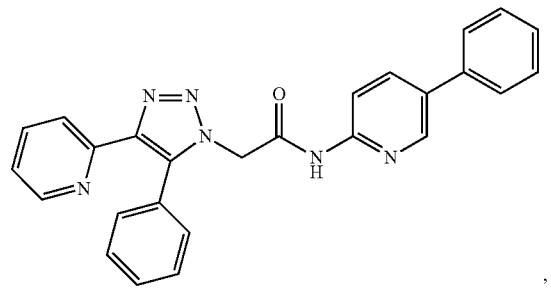
,
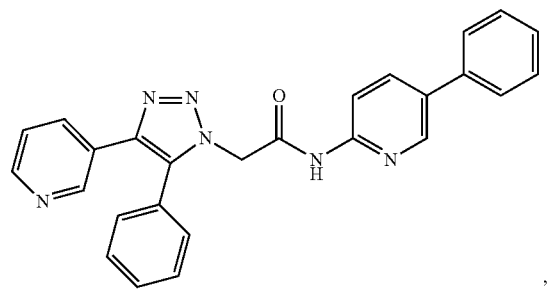
,
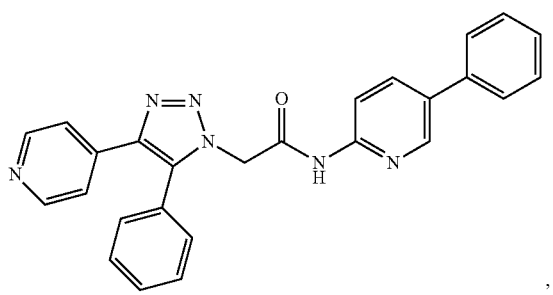 [SMILES: CC(C(=O)Nc1ccc(-c2ccccc2)cn1)n1nnc(-c2ccncc2)c1-c1ccccc1]
,
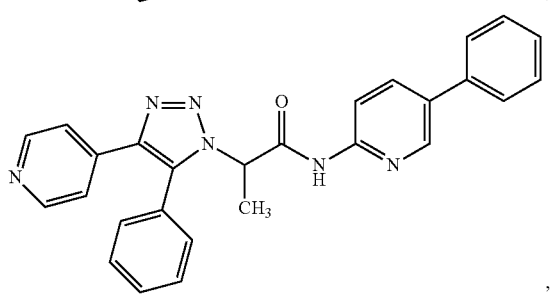
,
74
-continued
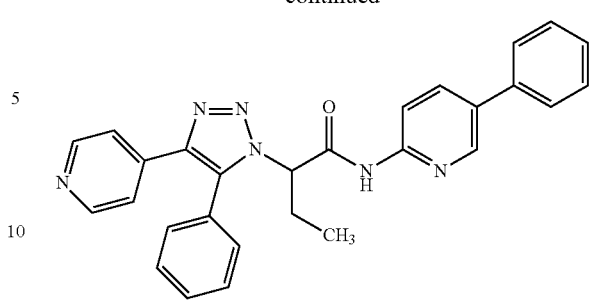
,
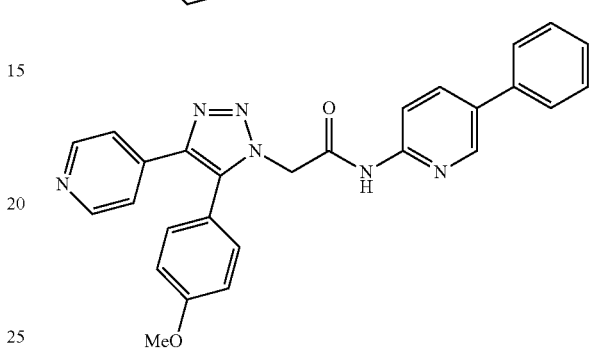
,
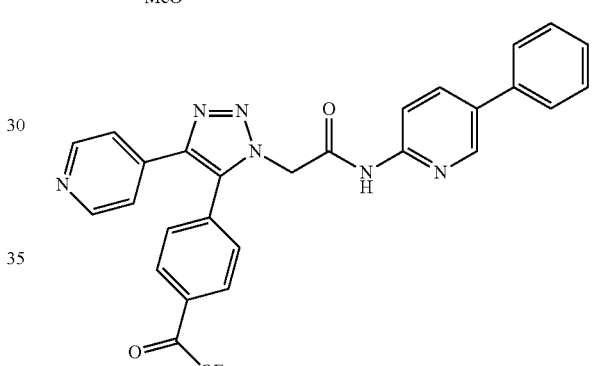
,
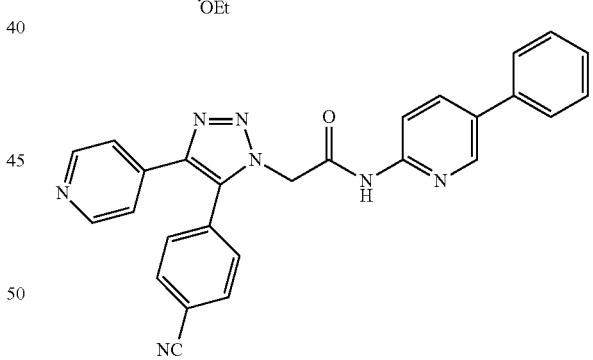
,
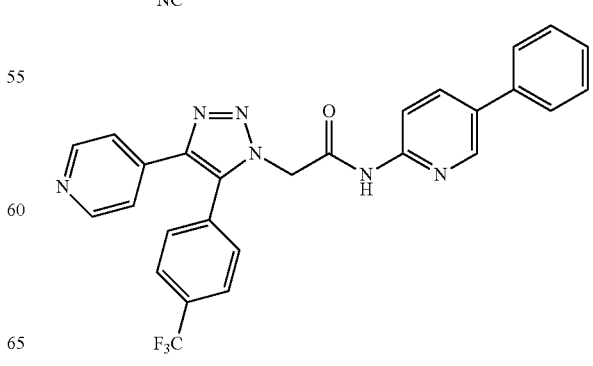
,

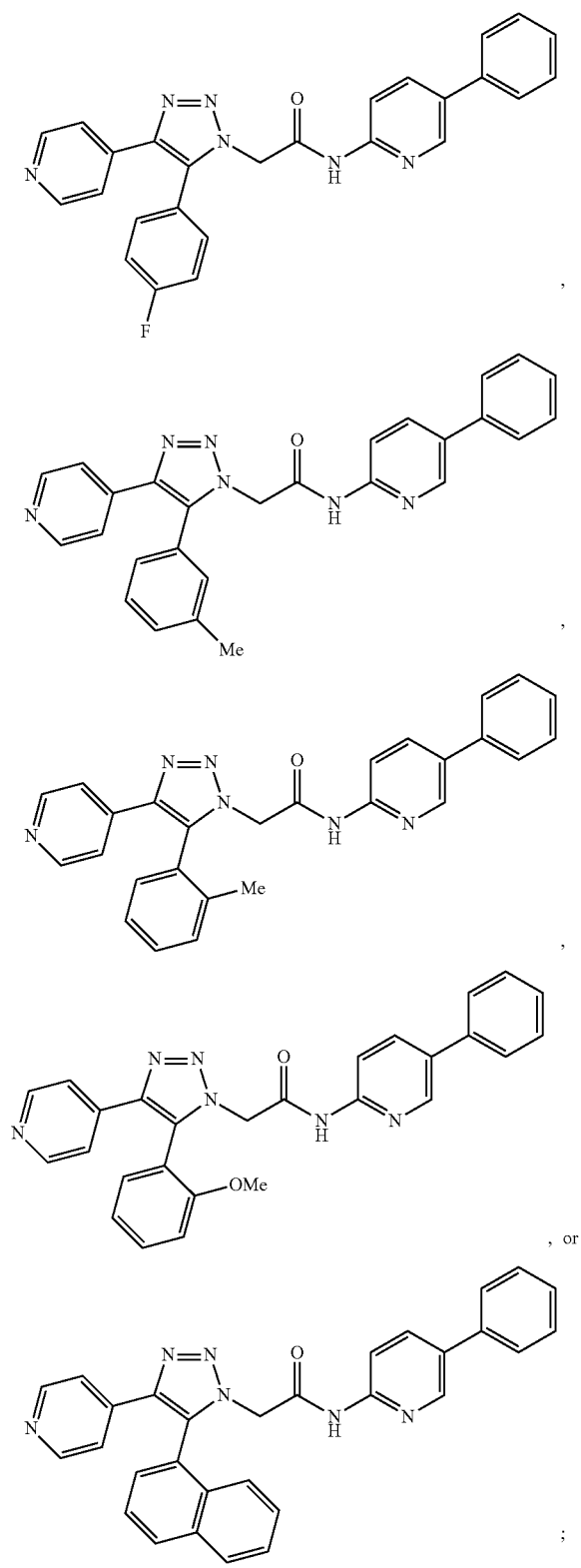 [SMILES: O=C(Cn1nnc(-c2ccncc2)c1-c1ccc(F)cc1)Nc1ccc(-c2ccccc2)cn1 ; Cc1cccc(-c2c(-c3ccncc3)nnn2CC(=O)Nc2ccc(-c3ccccc3)cn2)c1 ; Cc1ccccc1-c1c(-c2ccncc2)nnn1CC(=O)Nc1ccc(-c2ccccc2)cn1 ; COc1ccccc1-c1c(-c2ccncc2)nnn1CC(=O)Nc1ccc(-c2ccccc2)cn1 ; O=C(Cn1nnc(-c2ccncc2)c1-c1cccc2ccccc12)Nc1ccc(-c2ccccc2)cn1]
, or
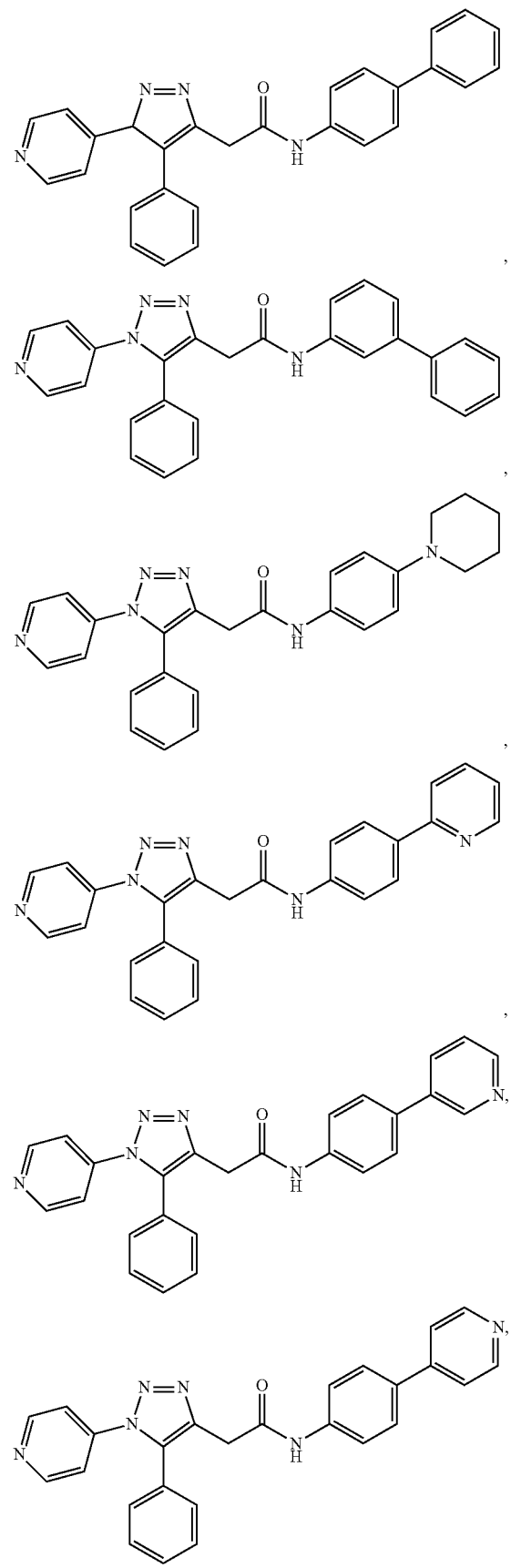
;
or a pharmaceutically acceptable salt thereof.
14. The compound according to claim 1, wherein the compound is further defined as:

77
-continued
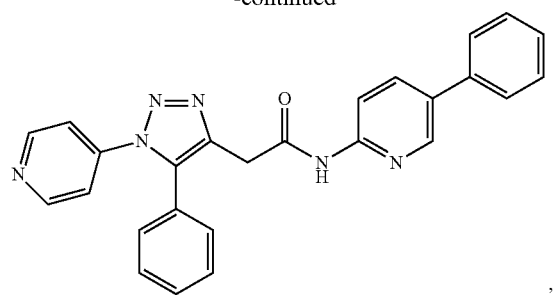
,
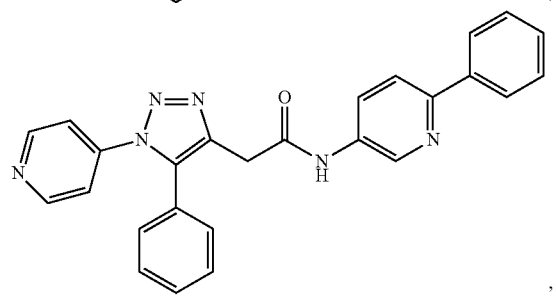
,
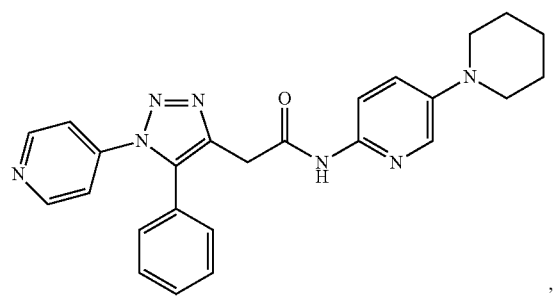
,
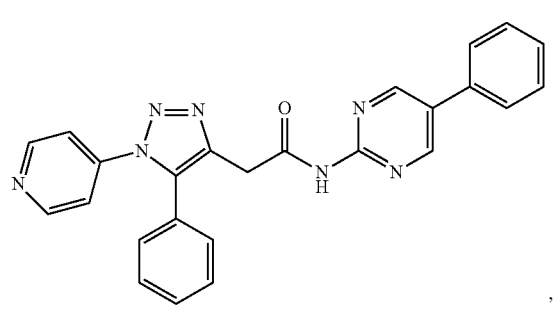
,
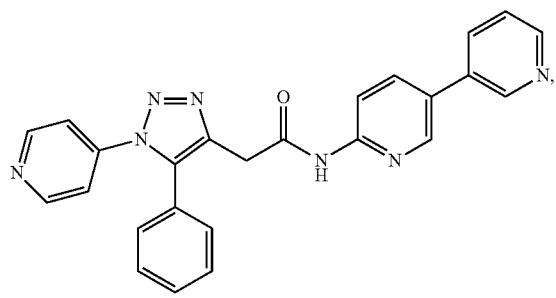
,
78
-continued
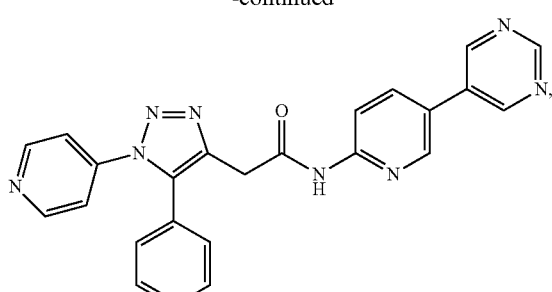
,
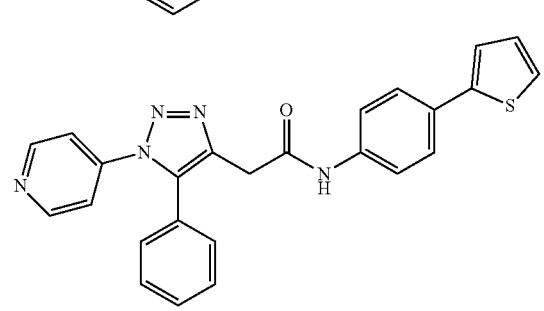
,
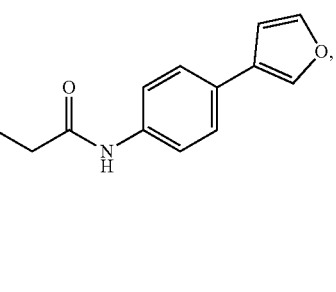
,

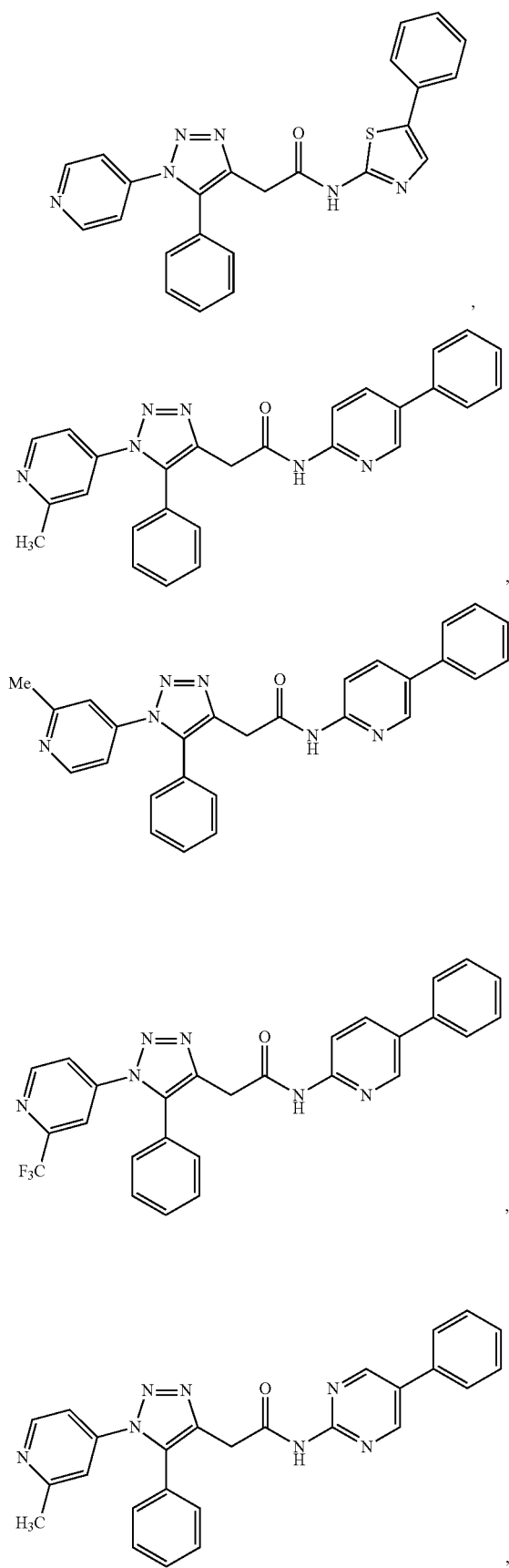
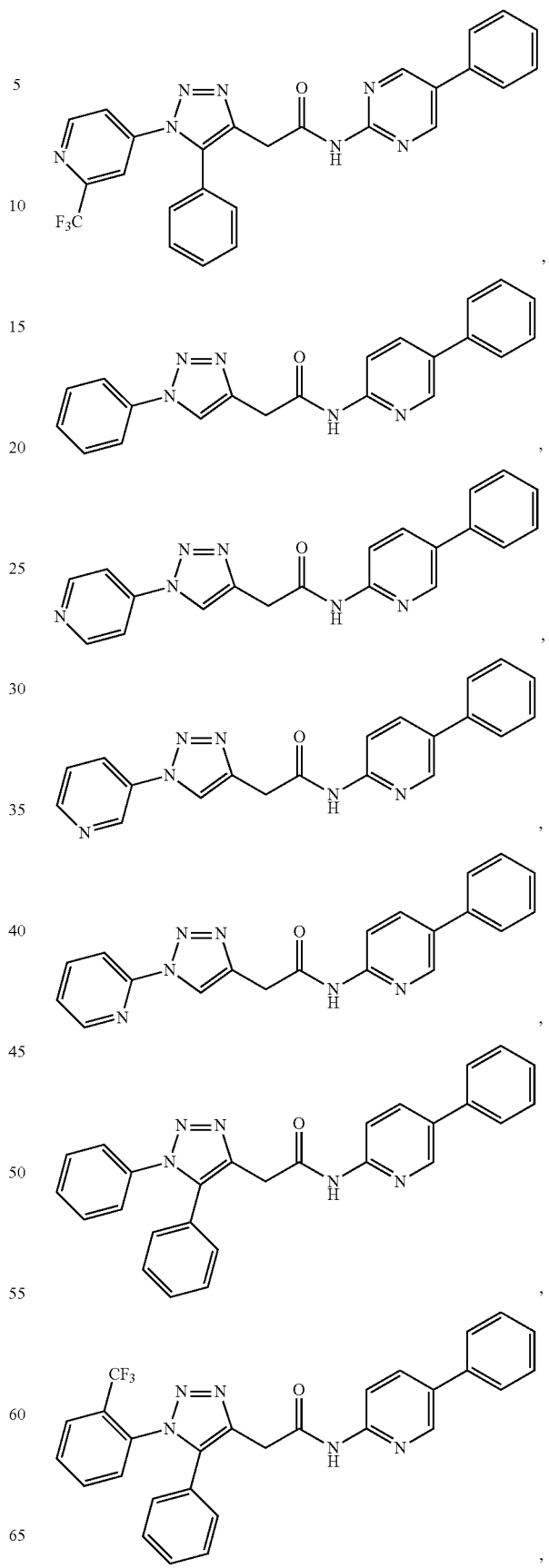

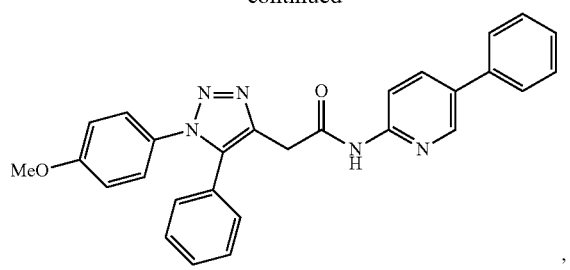,
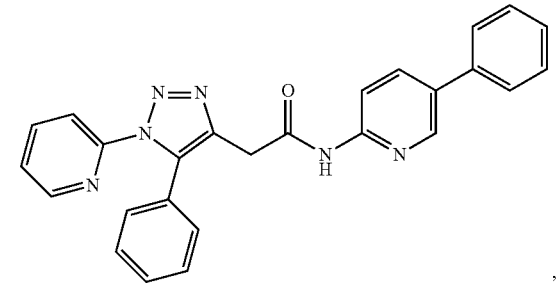,
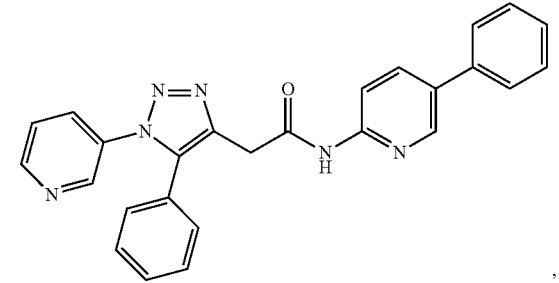,
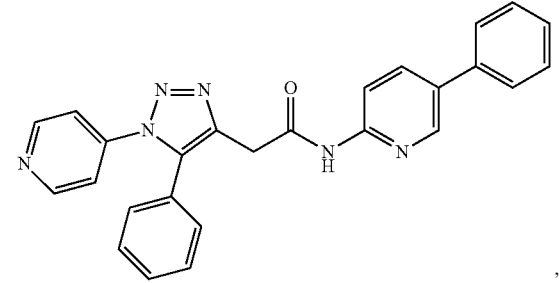,
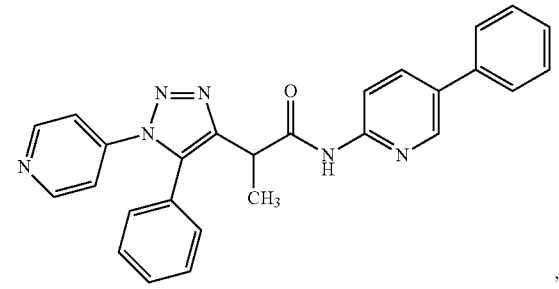 [SMILES: CC(C(=O)Nc1ccc(-c2ccccc2)cn1)c1nnn(-c2ccncc2)c1-c1ccccc1],
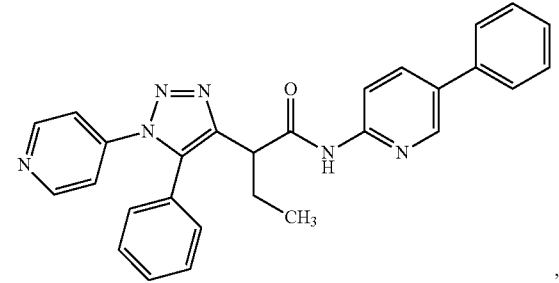,
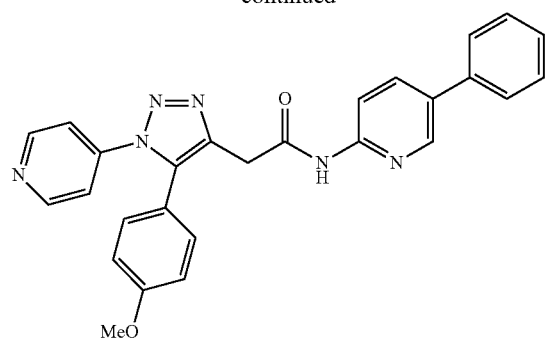,
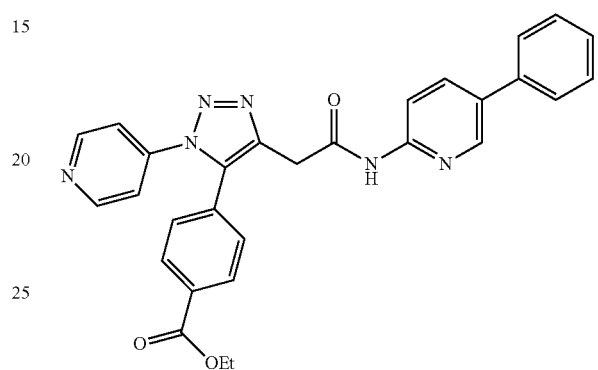,
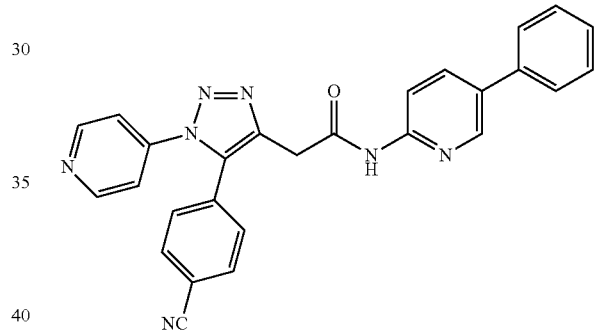,
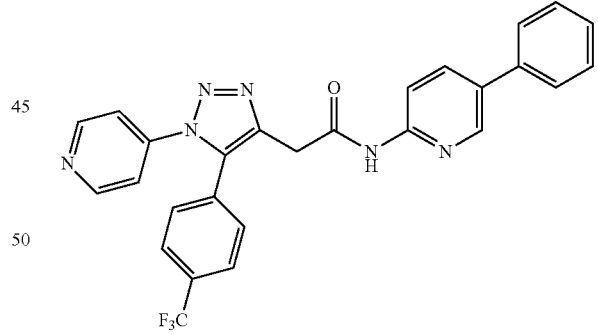,
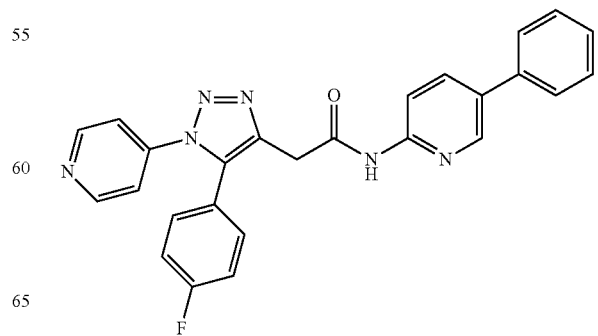,

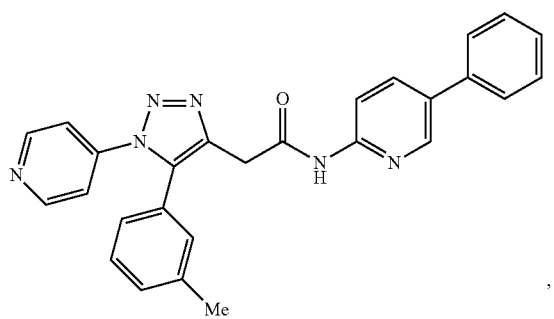

,

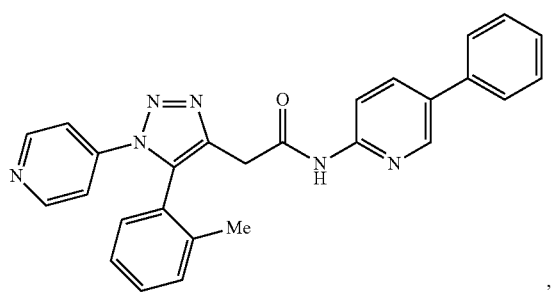

,

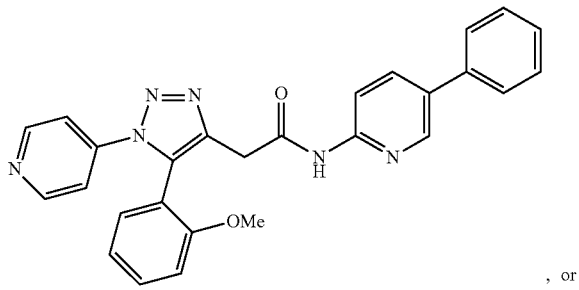

, or

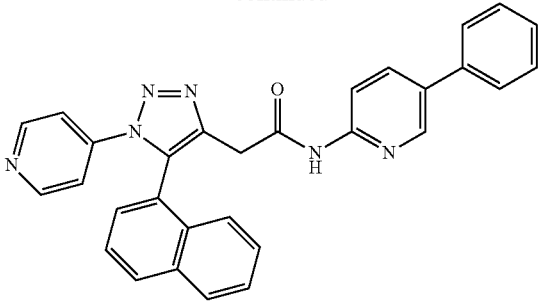

;

or a pharmaceutically acceptable salt thereof.

15. A pharmaceutical composition:
(A) a compound according to claim 1; and
(B) an excipient.

16. The pharmaceutical composition of claim 15, wherein the pharmaceutical composition is formulated for administration: orally, intraadiposally, intraarterially, intraarticularly, intracranially, intradermally, intralesionally, intramuscularly, intracardially, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctivally, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion.

17. A method of treating cancer in a patient comprising administering to the patient in need thereof a therapeutically effective amount of a compound or a pharmaceutically acceptable salt thereof according to claim 1.

18. A method of inducing differentiation of a precursor cell into a mature cell comprising administering to the precursor cell an effective amount of a compound or composition according to claim 1.

19. A method of inhibiting a Wnt protein comprising contacting the Wnt protein with an effective amount of a compound or composition according to claim 1.

* * * * *

UNITED STATES PATENT AND TRADEMARK OFFICE
CERTIFICATE OF CORRECTION

PATENT NO.       : 10,793,544 B2
APPLICATION NO.  : 16/330050
DATED            : October 6, 2020
INVENTOR(S)      : Nageswari Yarravarapu et al.

Page 1 of 1

It is certified that error appears in the above-identified patent and that said Letters Patent is hereby corrected as shown below:

In the Claims

Claim 13, Column 73, Lines 45-55, delete " 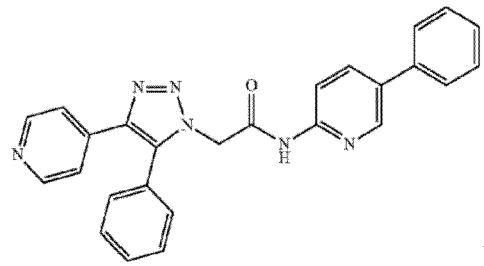 ".

Claim 14, Column 76, Lines 1-13, delete " 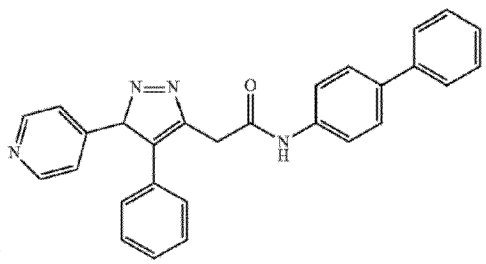 " and insert -- 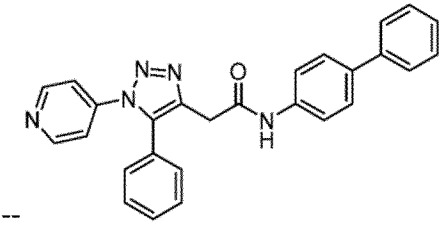 -- therefor.

Signed and Sealed this
Fourth Day of May, 2021

Drew Hirshfeld
*Performing the Functions and Duties of the
Under Secretary of Commerce for Intellectual Property and
Director of the United States Patent and Trademark Office*